United States Patent
Eberlin et al.

(10) Patent No.: US 10,643,832 B2
(45) Date of Patent: May 5, 2020

(54) COLLECTION PROBE AND METHODS FOR THE USE THEREOF

(71) Applicant: BOARD OF REGENTS, THE UNIVERSITY OF TEXAS SYSTEM, Austin, TX (US)

(72) Inventors: Livia Schiavinato Eberlin, Austin, TX (US); Thomas Milner, Austin, TX (US); Jialing Zhang, Austin, TX (US); John Lin, Austin, TX (US); John Rector, Austin, TX (US); Nitesh Katta, Austin, TX (US); Aydin Zahedivash, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/692,167

(22) Filed: Aug. 31, 2017

(65) Prior Publication Data

US 2018/0158661 A1    Jun. 7, 2018

Related U.S. Application Data

(60) Provisional application No. 62/383,234, filed on Sep. 2, 2016, provisional application No. 62/411,321, filed (Continued)

(51) Int. Cl.
  *H01J 49/00* (2006.01)
  *H01J 49/04* (2006.01)
  (Continued)

(52) U.S. Cl.
  CPC ...... *H01J 49/0431* (2013.01); *A61B 10/0045* (2013.01); *B01L 3/502* (2013.01);
  (Continued)

(58) Field of Classification Search
  CPC .. H01J 49/00; H01J 49/02; H01J 49/04; H01J 49/0404; H01J 49/0409; H01J 49/0413;
  (Continued)

(56) References Cited

U.S. PATENT DOCUMENTS 5,152,277 A   10/1992  Honda
5,241,990 A    9/1993  Cook
(Continued)

FOREIGN PATENT DOCUMENTS

WO   WO 2010/114976   10/2010
WO   WO 2015/061597    4/2015
(Continued)

OTHER PUBLICATIONS

Balog, Júlia, et al. "Intraoperative tissue identification using rapid evaporative ionization mass spectrometry." *Science translational medicine* 5.194 (2013): 194ra93-194ra93.
(Continued)

*Primary Examiner* — Jason L McCormack
(74) *Attorney, Agent, or Firm* — Parker Highlander PLLC

(57) ABSTRACT

Method and devices are provided for assessing tissue samples from a plurality of tissue sites in a subject using molecular analysis. In certain aspects, devices of the embodiments allow for the collection of liquid tissue samples and delivery of the samples for mass spectrometry analysis.

26 Claims, 39 Drawing Sheets

Related U.S. Application Data on Oct. 21, 2016, provisional application No. 62/462,524, filed on Feb. 23, 2017.

(51) Int. Cl.

| | |
|---|---|
| *A61B 10/00* | (2006.01) |
| *G01N 33/487* | (2006.01) |
| *B01L 3/00* | (2006.01) |
| *G01N 33/68* | (2006.01) |
| *G01N 1/02* | (2006.01) |
| *G01N 30/72* | (2006.01) |
| *G01N 33/574* | (2006.01) |
| *B01L 3/02* | (2006.01) |
| *G01N 1/40* | (2006.01) |

(52) U.S. Cl.
CPC ............... *G01N 1/02* (2013.01); *G01N 30/72* (2013.01); *G01N 33/487* (2013.01); *G01N 33/574* (2013.01); *G01N 33/6848* (2013.01); *H01J 49/0031* (2013.01); *H01J 49/04* (2013.01); *B01L 3/0293* (2013.01); *B01L 2200/0605* (2013.01); *B01L 2400/0655* (2013.01); *G01N 2001/028* (2013.01); *G01N 2001/4061* (2013.01); *G01N 2560/00* (2013.01)

(58) Field of Classification Search
CPC .. H01J 49/0431; H01J 49/0436; H01J 49/044; H01J 49/0445; H01J 49/045; H01J 49/10; H01J 49/14; H01J 49/145; H01J 49/165; H01J 49/167
USPC ......................................... 250/281, 282, 288
See application file for complete search history.

(56) References Cited

U.S. PATENT DOCUMENTS

| | | | |
|---|---|---|---|
| 5,384,260 | A | 1/1995 | Osborne et al. |
| 5,607,389 | A | 3/1997 | Edwards et al. |
| 5,711,816 | A | 1/1998 | Kirlin et al. |
| 5,746,720 | A | 5/1998 | Stouder, Jr. |
| 6,297,499 | B1 | 10/2001 | Fenn |
| 6,534,765 | B1 | 3/2003 | Robb |
| 6,677,593 | B1 | 1/2004 | Berkel |
| 6,784,439 | B2 | 8/2004 | Berkel |
| 6,803,566 | B2 | 10/2004 | Van Berkel |
| 6,808,510 | B1 | 10/2004 | DiFiore |
| 7,295,026 | B2 | 11/2007 | Van Berkel et al. |
| 7,335,897 | B2 | 2/2008 | Takats et al. |
| 8,084,735 | B2 | 12/2011 | Kertesz et al. |
| 8,207,494 | B2 | 6/2012 | Hieftje et al. |
| 8,314,382 | B2 | 11/2012 | Takats |
| 8,324,570 | B2 | 12/2012 | Wiseman et al. |
| 8,421,005 | B2 | 4/2013 | Musselman |
| 8,604,423 | B2 | 12/2013 | Enke et al. |
| 8,704,167 | B2 | 4/2014 | Cooks et al. |
| 8,710,437 | B2 | 4/2014 | Cooks et al. |
| 8,816,275 | B2 | 8/2014 | Ouyang et al. |
| 8,859,956 | B2 | 10/2014 | Ouyang et al. |
| 8,859,958 | B2 | 10/2014 | Ouyang et al. |
| 8,859,959 | B2 | 10/2014 | Ouyang et al. |
| 8,859,986 | B2 | 10/2014 | Cooks et al. |
| 8,890,063 | B2 | 11/2014 | Ouyang et al. |
| 8,933,398 | B2 | 1/2015 | Ouyang et al. |
| 8,937,288 | B1 | 1/2015 | Cooks et al. |
| 9,024,254 | B2 | 5/2015 | Cooks et al. |
| 9,035,239 | B1 | 5/2015 | Cooks et al. |
| 9,046,448 | B2 | 6/2015 | Takats |
| 9,105,458 | B2 | 8/2015 | Trimpin et al. |
| 9,116,154 | B2 | 8/2015 | Ouyang et al. |
| 9,281,174 | B2 | 3/2016 | Takats |
| 9,297,828 | B2 | 3/2016 | Ovchinnikova et al. |
| 9,305,759 | B2 | 4/2016 | McEwen et al. |
| 9,500,572 | B2 | 11/2016 | Ouyang et al. |
| 9,538,945 | B2 | 1/2017 | Cooks et al. |
| 9,552,973 | B2 | 1/2017 | McEwen et al. |
| 9,632,066 | B2 | 4/2017 | Van Berkel |
| 2003/0193020 | A1* | 10/2003 | Van Berkel ......... H01J 49/0404 250/288 |
| 2004/0059530 | A1 | 3/2004 | Paulse et al. |
| 2005/0061967 | A1 | 3/2005 | Shvartsburg et al. |
| 2005/0256424 | A1 | 11/2005 | Zimmon |
| 2006/0169030 | A1 | 8/2006 | Stewart et al. |
| 2006/0292607 | A1 | 12/2006 | Caprioli et al. |
| 2007/0114375 | A1* | 5/2007 | Pevsner ............ G01N 33/6851 250/282 |
| 2007/0135779 | A1 | 6/2007 | Lalomia et al. |
| 2007/0197954 | A1 | 8/2007 | Keenan |
| 2010/0176287 | A1* | 7/2010 | Ribbing .............. H01J 49/0418 250/282 |
| 2010/0224013 | A1 | 9/2010 | Van Berkel |
| 2010/0317964 | A1 | 12/2010 | Hendriks et al. |
| 2011/0021451 | A1 | 1/2011 | Wenk et al. |
| 2011/0133077 | A1 | 6/2011 | Henion et al. |
| 2011/0284735 | A1* | 11/2011 | Van Berkel .......... G01N 1/4055 250/282 |
| 2012/0053065 | A1* | 3/2012 | Van Berkel ........ H01J 49/0431 506/7 |
| 2012/0080592 | A1 | 4/2012 | Wiseman et al. |
| 2012/0085903 | A1 | 4/2012 | Trimpin |
| 2012/0149009 | A1 | 6/2012 | Levis et al. |
| 2012/0156712 | A1 | 6/2012 | Takats |
| 2012/0295276 | A1 | 11/2012 | Cooks et al. |
| 2013/0109592 | A1 | 5/2013 | Fan et al. |
| 2013/0115618 | A1 | 5/2013 | Swinnen |
| 2013/0273560 | A1 | 10/2013 | Cooks et al. |
| 2014/0179805 | A1 | 6/2014 | Stylli |
| 2014/0216177 | A1* | 8/2014 | Van Berkel ......... H01J 49/0431 73/863.81 |
| 2015/0008314 | A1 | 1/2015 | Sessler |
| 2015/0226745 | A1 | 8/2015 | Skotland et al. |
| 2015/0230738 | A1* | 8/2015 | Cooks ................ A61B 10/0045 600/352 |
| 2015/0275298 | A1 | 10/2015 | Stylli |
| 2015/0299808 | A1 | 10/2015 | Diaz et al. |
| 2015/0338413 | A1 | 11/2015 | Agar |
| 2015/0364306 | A1 | 12/2015 | Yang et al. |
| 2016/0041138 | A1 | 2/2016 | Pycke et al. |
| 2016/0047831 | A1 | 2/2016 | Cooks et al. |
| 2016/0168617 | A1 | 6/2016 | Yang et al. |
| 2016/0178629 | A1 | 6/2016 | Agar |
| 2016/0299041 | A1 | 10/2016 | Kertesz et al. |
| 2016/0314956 | A1* | 10/2016 | Cooks ..................... H01J 49/16 |
| 2016/0341712 | A1 | 11/2016 | Agar |
| 2017/0082604 | A1 | 3/2017 | Ouyang et al. |
| 2017/0097355 | A1 | 4/2017 | Raftery et al. |
| 2017/0248607 | A1 | 8/2017 | Cooks et al. |
| 2018/0158661 | A1 | 6/2018 | Eberlin et al. |
| 2018/0271502 | A1 | 9/2018 | Zarrine-Afsar et al. |
| 2018/0294148 | A1 | 10/2018 | Ouyang et al. |

FOREIGN PATENT DOCUMENTS

| | | |
|---|---|---|
| WO | WO 2016/142689 | 9/2016 |
| WO | WO 2016/142691 | 9/2016 |

OTHER PUBLICATIONS

Calligaris, David, et al. "Mass spectrometry imaging as a tool for surgical decision-making." *Journal of Mass Spectrometry* 48.11 (2013): 1178-1187.

Chiappetta, Gennaro, et al. "The RET/PTC oncogene is frequently activated in oncocytic thyroid tumors (Hurthle cell adenomas and carcinomas), but not in oncocytic hyperplastic lesions." *The Journal of Clinical Endocrinology & Metabolism* 87.1 (2002): 364-369.

Fatou, Benoit, et al. "In vivo Real-Time Mass Spectrometry for Guided Surgery Application." *Scientific reports* 6 (2016).

International Search Report and Written Opinion issued in International Application No. PCT/US17/41696, dated Dec. 28, 2017.

(56) References Cited

OTHER PUBLICATIONS

International Search Report and Written Opinion issued in International Application No. PCT/US17/49689, dated Jan. 4, 2018.
Invitation to Pay Additional Fees issued in International Application No. PCT/US17/49689, dated Oct. 27, 2017.
Jarmusch, Alan K., et al. "Lipid and metabolite profiles of human brain tumors by desorption electrospray ionization-MS." *Proceedings of the National Academy of Sciences* 113.6 (2016): 1486-1491.
Li, Tiegang, et al. "In situ biomarker discovery and label-free molecular histopathological diagnosis of lung cancer by ambient mass spectrometry imagining." *Scientific reports* 5 (2015).
Sapandowski, Anja, et al. "Cardiolipin composition correlates with prostate cancer cell proliferation," *Molecular and cellular biochemistry* 410.1-2 (2015): 175-185.
Schlumberger, Martin, et al. "Radioactive iodine treatment and external radiotherapy for lung and bone metastases from thyroid carcinoma." *The Journal of Nuclear Medicine* 37.4 (1996): 598.
Zhang, Jialing, et al. "Cardiolipins are biomarkers of mitochondria-rich thyroid oncocytic tumors." *Cancer research* 76.22 (2016): 6588-6597.
Zhang, Jialing, et al. "Nondestructive tissue analysis for ex vivo and in vivo cancer diagnosis using a handheld mass spectrometry system." *Science translational medicine* 9.406 (2017): eaan3968.
Feider et al., "Ambient Ionization and FAIMS Mass Spectrometry for Enhanced Imaging of Multiply Charged Molecular Ions in Biological Tissues", *Anal. Chem.*, 88(23):11533-11541, 2016.
International Search Report and Written Opinion issued in corresponding PCT Application No. PCT/US2019/019371, dated May 13, 2019.
Iyer et al., "Rising incidence of second cancers in patients with low-risk (T1N0) thyroid cancer who receive radioactive iodine therapy", *Cancer*, 117(19):4439-4446, 2011.
Tsuchiya et al., "Cluster Composition Distributions of Pure Ethanol: Influence of Water and Ion-Molecule Reactions Revealed by Liquid-Ionization Tandem Mass Spectrometry", *Mass Spectrom.*, 2(2):A0015, 2013.
International Search Report and Written Opinion issued in corresponding PCT Application No. PCT/US2018/062625, dated Mar. 14, 2019.
Invitrogen, "Custom Peptide Storage and Dissolution", [online] Internet <URL: http://tools.thermofisher.com/content/sfs/manuals/custompeptide_man.pdf>, first page, Jun. 6, 2003.
Kauppila et al., "Effect of the solvent flow rate on the ionization efficiency in atmospheric pressure photoionization-mass spectrometry", *J. Am. Soc. Mass Spec.*, 16(8):1399-1407, 2005.
Sigma Aldrich, "Ethanol standards 10% (v/v)", [online] Retrieved from the Internet <URL: https://www.sigmaaldrich.com/catalog/product/sigma/e2385?lang=en&region=US>, first page, Aug. 28, 2017.
Basile et al., "Analysis of lipids from crude lung tissue extracts by desorption electrospray ionization mass spectrometry and pattern recognition", *Anal Biochem.*, 408:289-296, 2011.
Bonora et al., "Defective Oxidative Phosphorylation in Thyroid Oncocytic Carcinoma is Associated with Pathogenic Mitochondrial DNA Mutations Affecting Complexes I and III", *Cancer Res.*, 66:6087-6096, 2006.
Camilleri-Broët et al., "Distinct alterations in mitochondrial mass and function characterize different models of apoptosis", *Exp. Cell. Res.*, 239:277-292, 1998.
Chicco and Sparagna, "Role of cardiolipin alterations in mitochondrial dysfunction and disease ", *Am. J. Physiol. Cell Physiol.*, 292(1) C33-C44, 2007.
De Paepe, "Mitochondrial markers for cancer: relevance to diagnosis, therapy, and prognosis and general understanding of malignant disease mechanisms", *ISRN Pathol.*, 217162:1-15, 2012.
Dobrzynska et al., "Changes in electric charge and phospholipids composition in human colorectal cancer cells", *Mol. Cell. Blochem.*, 276:113-119, 2005.

Eberlin et al,, "Alteration of the lipid profile in lymphomas induced by MYC overexpression"*Proc. Natl. Acad. Sci. USA*, 111:10450-10455, 2014.
Eberlin et al., "Classifying human brain tumors by lipid imaging with mass spectrometry", *Cancer Res.*, 72:645-654, 2012.
Ebertin et al., "Desorption electrospray ionization mass spectrometry for lipid characterization and biological tissue imaging", *Biochim. Biophys. Acta*, 1811:946-960, 2011.
Eberlin et al., "Molecular assessment of surgical-resection margins of gastric cancer by mass-spectmmetric imaging", *Proc. Natl. Acad. Sci. USA*, 111:2436-2441, 2014.
Galluzzi et al., "Mitochondrial gateways to cancer", *Mol. Aspects Med.*, 31:1-20, 2010.
Gasparre et al, "Relevance of mitochondrial genetics and metabolism in cancer development", *Cold Spring Harbor Perspect. Biol.*, 5(a011411):1-19, 2013.
Girod et al., "Desorption electrospray ionization imaging mass spectrometry of lipids in rat spinal cord", *J. Am. Soc. Mass Spectrom.*, 21:1177-1189, 2010.
Gogvadze, "Targeting mitochondria in fighting cancer", Curr. Pharm. Design, 17:4034-4046, 2011.
Guo et al,. "Significantly increased monounsaturated lipids relative to polyunsaturated lipids in six types of cancer microenvironment are observed by mass spectrometry imaging", *Sci. Rep.*, 4(5959):1-9, 2014.
Guo et al., "Tissue imaging and serum lipidomic profiling for screening potential biomarkers of thyroid tumors by matrix-assisted laser desorption/ionization-Fourier transform ion cyclotron resonance mass spectrometry", *Anal. Bioanal. Chem.*, 406:4357-4370, 2014.
Han et al., "Shotgun lipidomics identifies cardiolipin depletion in diabetic myocardium linking altered substrate utilization with mitochondrial dysfunction", Biochemistry, 44:16684-16694, 2005.
Henry-Mowatt et al., "Role mitochondrial membrane permeabilization in apoptosis and cancer", *Oncogene*, 23:2850-2860, 2004.
Ishikawa et al., "Increased expression of phosphatidylcholine (16: 0/18: 1) and (16: 0/18: 2) in thyroid papillary cancer", *PLoS One*, 7(e48873):1-9, 2012.
Kiebish et al., "Cardiolipin and electron transport chain abnormalities in mouse brain tumor mitochondria: lipidomic evidence supporting the Warburg theory of cancer". *J. Lipid Res.*, 49:2545-2556, 2008.
Laskin et al., "Tissue imaging using nanospray desorption electrospray ionization mass spectrometry", *Anal. Chem.*, 84:141-148, 2012.
Maciel et al., "Liquid chromatography/tandem mass spectrometry analysis of long-chain oxidation products of cardiolipin induced by the hydroxyl radical", *Rapid Comm. Mass Spectrom.*, 25:316-326, 2011.
Merchant et al., "Phospholipid profiles of human colon cancer using 31P magnetic resonance spectroscopy", *Int.J. Colorectal Dis.*, 6:121-126, 1991.
Mimezami et al., "Chemical mapping of the colorectal cancer microenvironment via MALDI imaging spectrometry (MALDI-MSI) reveals novel cancer—associated field effects", *Mol. Oncol.*, 8:39-49, 2014.
Murke et al.. "The mitochondrial phospholipid cardiolipin is involved in the regulation of T-cell proliferation", *Biochim. Blophys. Acta*, 1861:748-754, 2016.
Nicolson "Lipid replacement therapy: A nutraceutical approach for reducing cancer-associated fatigue and the adverse effects of cancer therapy while restoring mitochondrial function", *Cancer Metastasis Rev.*, 29:543-552, 2010.
Nicolson, "Mitochondrial Dysfunction and Disease: Loss of Mitochondrial Function in Chronic Diseases and its Reversal with Lipid Replacement Therapy", *Public Health Alert*, pp. 1-8, 2012.
Novais, "Cardiolipin Content in P19 Embryonal Carcinoma Cells", Thesis presented at the University of Coimbra, 112 pages, 2014.
Nygyen et al, "Bioimaging TOF-SIMS: High resolution 3D imaging of single cells", *Microscopy Res. Tech.*, 70(11):969-974, 2007.
Office Communication issued in U.S. Appl. No. 15/648,276, dated Sep. 13, 2019.

(56) References Cited

OTHER PUBLICATIONS

Pathak et al., "Tafazzin protein expression is associated with tumorigenesis and radiation response in rectal cancer: a study of Swedish clinical trial on preoperative radiotherapy", *PloS One*, 9(e98317):1-8, 2014.

Sapandowski et at., "Cardiolipin composition correlates with prostate cancer cell proliferation", *Mol. Cell. Biochem.*, 410(1-2):175-185, 2015.

Schild et al., "Composition of molecular cardiolipin species correlates with proliferation of lymphocytes", *Exp. Biol. Med.*, 237:372-379, 2012.

Schlame et al., "Microanalysis of cardiolipin in small biopsies including skeletal muscle from patients with mitochondrial disease", *J. Lipid Res.*, 40:1585-1592, 1999.

Scott et al., "Mass spectrometry imaging enriches biomarker discovery approaches with candidate mapping", *Health Phys.*, 106:120-128, 2014.

Shimma et al., "MALDI-based imaging mass spectrometry revealed abnormal distribution of phospholipids in colon cancer liver metastasis", *J. Chromatogr. B*, 855:98-103, 2007.

Shroff et al, "MYC oncogene overexpression drives renal cell carcinoma in a mouse model through glutamine metabolism", Proc. Natl. Acad. Sci. USA, 112:6539-6544, 2015.

Smith and Murphy "Animal and human studies with the mitochondria-targeted antioxidant MitoQ", *Ann. N.Y. Acad. Sci.*, 1201:96-103, 2010.

Sotgia et al., "Mitochondrial oxidative stress drives tumor progression and metastasis: should we use antioxidants as a key component of cancer treatment and prevention?", *BMC Med.*, 9(62):1-5, 2011.

Watrous et al., "Metabolic profiling directly from the Petri dish using nanospray desorption electrospray ionization imaging mass spectrometry", *Anal. Chem.*, 85:10385-10391, 2013.

Yang et al., "Mitochondrial dysregulation and protection in cisplatin nephrotoxicity", *Arch. Toxicol.*, 88:1249-1256, 2014.

Yin and Zhu, "Free radical oxidation of cardiolipin: chemical mechanisms, detection and implication in apoptosis, mitochondrial dysfunction and human diseases", *Free Rad. Res.*, 46:959-974, 2012.

Zimmermann et al., "Lack of complex I is associated with oncocytic thyroid tumours", *Br. J .Cancer*, 100:1434-1437, 2009.

Extended European Search Report Issued in corresponding European Application No. 17847571.1, dated Mar. 4, 2020.

Ifa, Demian R., and Livia S. Eberlin "Ambient ionization mass spectrometry for cancer diagnosis and surgical margin evaluation." *Clinical chemistry* 62.1 (2016): 111-123.

\* cited by examiner

Figure 1L - Negative ion mode mass spectra from a mouse brain tissue section using the MasSpec Pen connected to a Venturi-ESI source (design similar to slide 8)

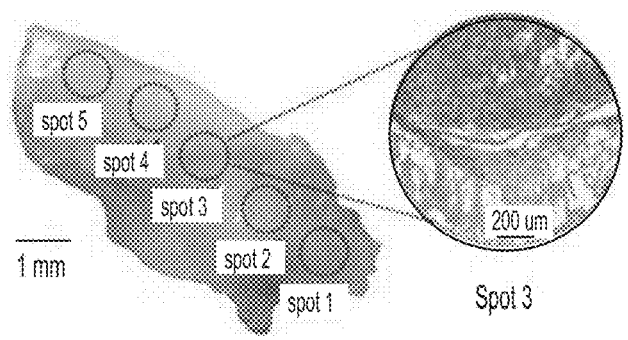
FIG. 14A
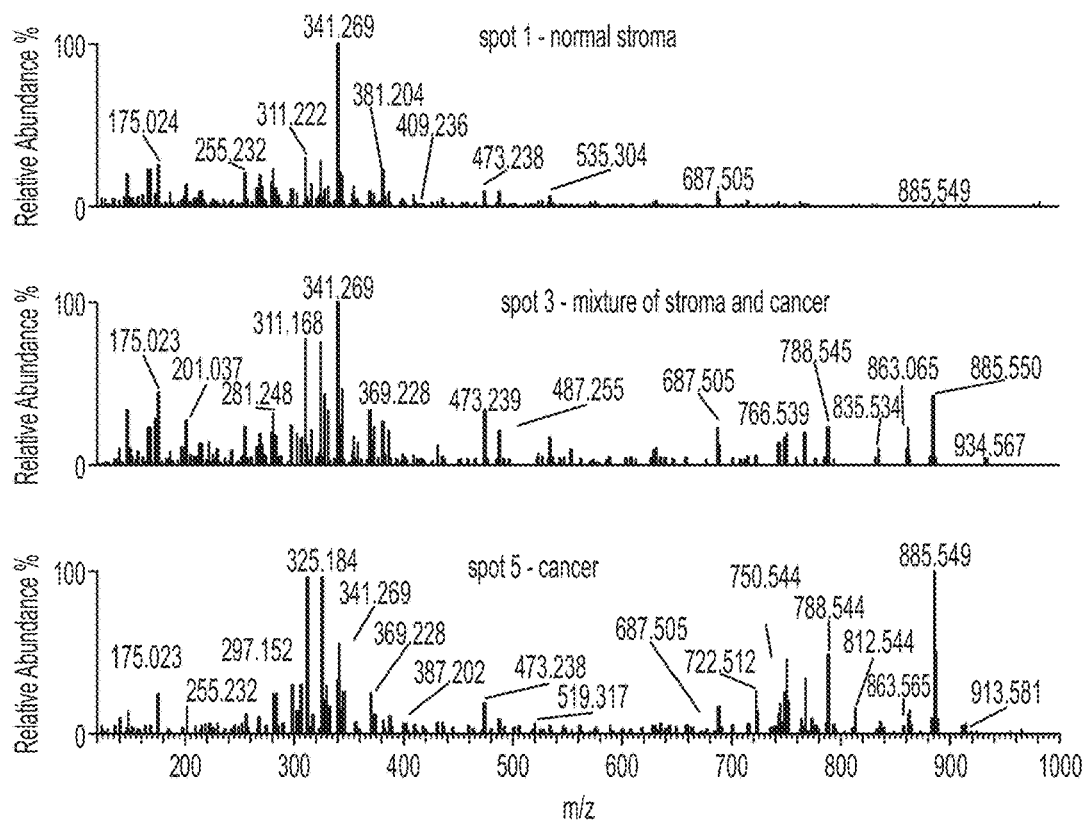
FIG. 14B
| Spot | Pathologic Diagnosis | Lasso Prediction |
|---|---|---|
| 1 | normal stroma | normal |
| 2 | normal stroma | normal |
| 3 | stroma (~50%) and cancer (~50%) | cancer |
| 4 | Ovarian cancer | cancer |
| 5 | Ovarian cancer | cancer |
FIG. 14C

COLLECTION PROBE AND METHODS FOR THE USE THEREOF

This application claims the benefit of U.S. Provisional Patent Application Nos. 62/383,234, filed Sep. 2, 2016; 62/411,321, filed Oct. 21, 2016; and 62/462,524, filed Feb. 23, 2017, each of which is incorporated herein by reference in its entirety.

This invention was made with government support under Grant No. R00 CA190783 awarded by the National Institutes of Health. The government has certain rights in the invention.

BACKGROUND OF THE INVENTION

1. Field of the Invention

The present invention relates generally to the field of medicine, molecular biology and biochemistry. More particularly, it concerns methods and devices for assessment of tissue samples using mass spectrometry.

2. Description of Related Art

Clinical diagnosis is commonly performed through the evaluation of tissue samples pre-operatively, intra-operative, and post-operatively, at several other stages of the patient's treatment process. Tissue evaluation is very critical in the diagnosis and management of cancer patients. Intra-operative pathologic assessment of excised tissues, for example, is routinely performed for diagnosis and surgical margin evaluation in a variety of cancer surgeries. The resected tissue specimens are sent to a nearby room, often called the "frozen room", for tissue preparation, staining, and evaluation. The tissue specimen is frozen, sectioned, stained, and interrogated using light microscopy by an expert pathologist who carefully evaluates if the surgical margins contain cancer cells (positive margin) or not (negative margin). While intraoperative frozen section analysis has been performed in clinical practice for decades, it presents many challenges. Freezing artifacts occur during tissue processing and interfere with tissue structure and cell morphology, thus complicating pathologic interpretation. Moreover, certain tumor cells are very difficult to recognize due to their atypical pattern of growth and shape. Molecular approaches could provide highly accurate and potentially real-time assessments of tissue samples. However, to date adequate devices or methodologies have not been developed that provide effective molecular assessment of tissue samples.

SUMMARY OF THE INVENTION

In a first embodiment there is provided a method for obtaining a mass spectrometry profile comprising using a probe to apply a fixed or discrete volume of a solvent to an assay site (e.g., a tissue site); using the probe to collect the applied solvent to obtain a liquid sample; and subjecting the liquid sample to mass spectrometry analysis. In further embodiment a method is provided for assessing tissue samples comprising obtaining a plurality of liquid samples from a plurality of tissue sites in a subject and subjecting the plurality of liquid samples to mass spectrometry.

Still a further embodiment provides an apparatus for obtaining samples (e.g., from tissues) for mass spectrometry analysis, the apparatus comprising: a chamber comprising a solvent; a pressurized gas supply; a mass spectrometer; a probe comprising a reservoir, a first conduit, a second conduit and a third conduit, wherein: the reservoir is in fluid communication with the first conduit, the second conduit and the third conduit; the first (solvent) conduit is in fluid communication with the chamber; the second (gas) conduit is in fluid communication with pressurized gas supply; and the third (collection) conduit is in fluid communication with the mass spectrometer. In further aspects, the mass spectrometer in communication with a computer that provides a sample analysis. In certain aspects, the results of each sample analysis are provided by a visual or auditory output from the computer. For example, the results of each sample analysis by the computer can be indicated by a differently colored light that is illuminated or by a different frequency of sound produced. In some aspects, the mass spectrometer is a mobile the mass spectrometer. In further aspects, the mass spectrometer can comprise an uninterruptable power supply (e.g., a battery power supply). In still further aspects, the mass spectrometer comprises an inlet that may be closed to keep instrument vacuum. In yet further aspects, the mass spectrometer is separated from the probe by a mesh filter (e.g., to block contamination).

In some aspects, the reservoir is configured to form a droplet of the solvent. In certain aspects, the pressurized gas supply provides a gas to the probe at a pressure between 0.1 psig and 5.0 psig. In further aspects, the pressurized gas supply provides a gas to the probe at a pressure between 0.5 psig and 2.5 psig. In several aspects, the pressurized gas supply provides air to the probe. In other aspects, the pressurized gas supply provides an inert gas such as nitrogen or carbon dioxide to the probe.

In additional aspects, the apparatus further comprises a pump configured to transfer the solvent from the chamber to the first conduit. In further aspects, the apparatus may comprise a first valve configured to control a flow from the third conduit to the mass spectrometer. In some aspects, the third conduit is under a vacuum when the first valve is in the open position. In other aspects, the apparatus may comprise a second valve configured to control a flow of pressurized gas through the second conduit.

In certain aspects, the solvent may comprise water and/or ethanol. In several aspects, the probe is formed from polydimethylsiloxane (PDMS) and/or polytetrafluoroethylene (PTFE). In some aspects, the probe is disposable. In particular aspects, the probe may include a collection tip that is ejectable (e.g. capable of being ejected from the probe). In further aspects, the probe comprises a tracking device configured to track a location of the probe. In some aspects, the reservoir has a volume between 1 microliter and 500 microliters, between about 1 microliter and 100 microliters or between about 2 microliters and 50 microliters. In additional aspects, the reservoir has a volume between 5.0 microliters and 20 microliters.

In still further aspects, the apparatus may additionally comprise a control system configured to control: a solvent flow (e.g., flow of a fixed or discrete volume of solvent) from the chamber through the first conduit to the reservoir; a pressurized gas flow from the pressurized gas supply through the second conduit to the reservoir; and a sample flow from the reservoir through the third conduit to the mass spectrometer. In some aspects, the control system is configured to: control the solvent flow at a flow rate between 100 and 5000 microliters per minute (e.g., between 200 and 400 microliters per minute) for a period of time between 1 and 3 seconds; control the pressurized gas flow at a flow rate between 1 and 10 psig for a period of time between 10 and 15 seconds; and control the sample flow for a period of time between 10 and 15 seconds. For example, in some aspects, the control system comprises a trigger or button to initiate solvent flow. In further aspects, the control system comprises a pedal (i.e., that can be operated by foot action) to initiate solvent flow. A skilled artisan will recognize that the lengths of the first and/or second conduit may be adjusted to fit the particular use of the system. In yet further aspects, the control system is configured to control: a solvent flow (e.g., flow rate for a fixed period of time) from the chamber through the first conduit to the reservoir. In further aspects, an apparatus of the embodiments does not include a device for producing ultrasonic or vibrational energy (e.g., in sufficient amounts to disrupt tissues).

A further embodiment provided a method for assessing tissue samples from a subject comprising applying a solvent to a tissue site on the subject, collecting the applied solvent to obtain a liquid sample, and subjecting the sample to mass spectrometry analysis. In certain aspects, the solvent may be sterile. In some aspects, the solvent is pharmaceutically acceptable formulation. In specific aspects, the solvent is an aqueous solution. For example, the solvent may be sterile water or consist essentially of water. In other aspects, the solvent may comprise from about 1% to 5%, 10%, 15%, 20%, 25% or 30% of an alcohol. In some aspects, the solvent comprises 0.1% to 20% of an alcohol, 1% to 10% of an alcohol or 1% to 5% 1% to 10% of an alcohol (e.g., ethanol). In some cases, the alcohol may be ethanol.

In some aspects, applying the solvent to the tissue comprises applying a discrete volume of solvent to the tissue site. In some aspect, the solvent is applied in a single droplet. In a further aspect, the solvent is applied in a discrete number of droplets from 1 to 10. In some embodiments, the solvent is applied to the sample from the reservoir via a channel independent of the pressurized gas. In further embodiments, the solvent is applied to the sample under low pressure. For example, in some aspects, the solvent is applied by a mechanical pump such that solvent is applied to the tissue site (e.g., moved into a reservoir where it is in contact with the tissue site) with minimal force thereby exerting minimal pressure (and producing minimal damage) at a tissue site. The low pressure may be less than 100 psig, less than 90 psig, less than 80 psig, less than 70 psig, less than 60 psig, less than 50 psig, or less than 25 psig. In some embodiments, the low pressure is from about 0.1 psig to about 100 psig, from about 0.5 psig to about 50 psig, from about 0.5 psig to about 25 psig, or from about 0.1 psig to about 10 psig. In particular aspects, the discrete volume of solvent is between about 0.1 and 100 µL or between about 1 and 50 µL. In further aspects, collecting the applied solvent is between 0.1 and 30 seconds after the applying step. In a specific aspect, collecting the applied solvent is between 1 and 10 seconds after the applying step (e.g., at least 1, 2, 4, 5, 6, 7, 8 or 9 seconds). In further aspects, a method of the embodiments does not involve application of ultrasonic or vibrational energy to a sample or tissue. In some aspects, the tissue site in an internal tissue site that is being surgically assessed.

In a further aspect, a method of the embodiments comprises applying a fixed or discrete volume of a solvent (e.g., using mechanical pump) to a tissue site through a solvent conduit. In some aspects, the fixed or discrete volume of a solvent is moved through a solvent conduit into a reservoir where it is in direct contact with a tissue site (e.g., for 0.5-5.0 seconds). In further aspects, collecting the applied solvent comprises applying a negative pressure to pull the sample into a collection conduit and/or applying a gas pressure to push the sample into a collection conduit. In some aspects, the solvent is applied through a solvent conduit that is separate from the collection conduit. In further aspects, wherein a gas pressure is applied to push the sample into the collection conduit the gas pressure is applied through a gas conduit that is separate from the solvent conduit and the collection conduit. In certain aspects, wherein a gas pressure is applied to push the sample into the collection conduit, the applied gas pressure of less than 100 psig. For example, the gas pressure is preferably less than 10 psig, such as 0.1 to 5 psig. In still further aspects, a method of the embodiments is defined as producing no detectable physical damage to the tissue being assessed.

In still further aspects, the method may additionally comprise collecting a plurality liquid samples from a plurality of tissue sites. In some cases, the device (e.g., the probe) used to collect the samples is washed between each sample collection. In other aspects, a device used to collect the samples includes a disposable collection tip (probe) that can be changed between each sample collection. In particular aspects, the collection tip may be ejectable (e.g. capable of being ejected from the device). In certain aspects, the plurality of tissue sites comprise 2, 3, 4, 5, 6, 7, 8, 9, 10 or more tissues sites in vivo. In another aspect, the plurality of tissue sites surround a section of tissue that has been surgically resected (e.g., ex vivo). In a specific aspect, the resected tissue is a tumor. In some aspects, the method may be defined as an intraoperative method.

A further embodiment provides a method of identifying a sampled tissue site and a method to communicate location of the site to the device (probe) operator. Identification of a sampled tissue site allows the operator to access the molecular information recorded at sampled tissue site at a time after sampling molecules collected from the tissue. At least three types of identification approaches are recognized. In the first approach, an exogenous material is attached to the sampled tissue site that identifies the sampled molecular information. In a second approach, the device (probe) is equipped with a tracking sensor/emitter that allows recording the location of the probe (device) and communication to an imaging device when the molecular information is sampled. In a third approach, the tissue region is modified so that the site may be easily identified after harvesting tissue molecules. In the first approach, materials that may be attached to the sampled tissue site include, for example, a suture, a surgical clip, a biocompatible polymer that adheres to the tissue, or an RFID chip that is attached to a magnetic bead that allows easy reading and removal. In the second approach type, the probe may contain an RF emitter that is part of a RF surgical tracking system, an ultrasound emitter or reflector that is part of an intra-operative US imaging system. In this second approach, when the operator initiates collection of tissue molecules, the tracking system records location of the probe in the associated imaging system (e.g., RF, US, CT, MRI) that may be in communication with the device. The operator may then identify any of the sampled tissue sites at a later time by referring to the recorded image(s) that can indicate the location of sampled sites to the operator. In the third approach, the tissue is modified. In this third approach, a laser source in communication with the probe may be used to ablate or coagulate a pattern into the tissue that identifies the sampled site. Any of these three approaches may be combined. For example, approach 1, 2 and 3 could be combined wherein an exogenous material is attached to the tissue site after harvesting tissue molecules and a laser patterns the exogenous tissue while an RF sensor records location of the harvest location and communicates to the imaging device.

In yet still further aspects, the mass spectrometry comprises ambient ionization MS. In several aspects, subjecting the sample to mass spectrometry analysis may comprise determining a profile corresponding to the tissue site. In another aspect, the method may additionally comprise comparing the profile to a reference profile to identify tissue sites that include diseased tissue. In other aspects, the method also comprises resecting tissue sites that are identified to include diseased tissue. In some aspects, the method is performed using an apparatus in accordance with any of the embodiments and aspects described above.

In a further embodiment, the invention provides an ex vivo method for assessing tissue samples comprising obtaining a plurality of liquid samples from a plurality of tissue sites in a subject, subjecting the plurality of liquid samples to mass spectrometry to obtain a plurality of profiles corresponding to the tissue sites, and comparing the plurality of profiles to reference profiles to identify tissue sites that include diseased tissue. In certain aspects, the liquid samples are comprised in a solvent. In further aspects, the diseased tissues comprise cancer cells.

In some aspects of the embodiments, the diseased tissue sites for assessment by methods and devices of the embodiments comprise (or are suspected of comprising) cancer cells. Cancer cells that may be assessed according to the embodiments include but are not limited to cells or tumor tissues from a thyroid, lymph node, bladder, blood, bone, bone marrow, brain, breast, colon, esophagus, gastrointestine, gum, head, kidney, liver, lung, nasopharynx, neck, ovary, prostate, skin, stomach, testis, tongue, or uterus (or tissues surrounding such tumors). In some aspects, the cancer may be a neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous hi stiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; or paragranuloma. In further aspects the cancer is a thyroid cancer, brain cancer (e.g., a glioma), a prostate cancer, a breast cancer (e.g., a triple negative breast cancer), a pancreatic cancer (e.g., a pancreatic ductal adenocarcinoma), acute myeloid leukemia (AML), melanoma, renal cell cancer or a cancer that has metastasized to a lymph node.

As used herein, "sample" or "liquid samples" can refer to extracts from tissues or other biological specimens (e.g., extracts comprising proteins and metabolites) obtained by contacting tissue or biological specimen with a solvent according to the embodiments. In some aspects, a sample can be an extract from a non-biological specimen, such as the surface on an object (e.g., a forensic sample).

As used herein, "essentially free," in terms of a specified component, is used herein to mean that none of the specified components has been purposefully formulated into a composition and/or is present only as a contaminant or in trace amounts. The total amount of the specified component resulting from any unintended contamination of a composition is therefore well below 0.01%. Most preferred is a composition in which no amount of the specified component can be detected with standard analytical methods.

As used herein in the specification and claims, "a" or "an" may mean one or more. As used herein in the specification and claims, when used in conjunction with the word "comprising", the words "a" or "an" may mean one or more than one. As used herein, in the specification and claim, "another" or "a further" may mean at least a second or more.

As used herein in the specification and claims, the terms "conduit" and "tube" are used interchangeably and refer to a structure that can be used to direct flow of a gas or liquid.

As used herein in the specification and claims, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 14A-14C: MasSpec Pen analysis of a HGSC tissue sample with mixed histologic composition. A) Optical image shows the tissue sample which was analyzed at the demarcated spots (1-5) using a 1.5 mm diameter MasSpec Pen. After MasSpec Pen analysis, the tissue sample was frozen, sectioned and H&E stained. An optical image of H&E stained tissue section obtained at spot 3 is shown, presenting mixed histologic composition including cancer and adjacent normal stroma tissue. B) The MasSpec Pen negative ion mode mass spectra is shown for spot 1 (normal stroma), spot 3 (mixture of normal stroma and cancer), and spot 5 (cancer). C) Pathologic diagnosis of the five spots analyzed and Lasso prediction results for this independent set of data are shown.

DESCRIPTION OF ILLUSTRATIVE EMBODIMENTS

I. The Present Embodiments

In certain aspects, the instant application provides methods and devices for molecular assessment of samples, such as tissue samples. In particular, aspects the methods can be used to assess multiple tissue sites during an operation (or biopsy) of the tissue. This feature allows for accurate identification of diseased tissues (e.g., tissue sites retaining cancer cells) in "real-time" allowing surgeons to more accurately address only the diseased tissue relative to surrounding normal tissues. In particular aspects, the methods disclosed here can involve delivery of a fixed or discrete volume of solvent to a tissue site, followed by collection of a liquid sample from the site and analysis of the liquid sample by mass spectrometry. Importantly, rather than being applied in a high pressure spray, solvent is applied as discreet droplets and at low pressure. These methods allow for accurate collection of samples from a distinct tissue site while avoiding damage to the tissue being assessed. The resulting mass spectrometry profile from collected samples allows for differentiation of diseased versus normal tissue sites. The method can be repeated at multiple sites of interest to very accurately map molecular changes (e.g., in a tissue). Importantly, the profiles of samples could be differentiated even with-out the use an ionization source. Thus, while methods of the embodiments could be used in conjunction with an ionization source, the use of such a source is not required. These methodologies can allow assessment of plurality of tissue sites over a short range of time, thereby allowing for very accurate assessment of the boundaries of diseased versus normal tissues.

In some aspects, the methods detailed herein can be used to collect and analyze samples from a wide range of sources. For example, the methods can be used to assess forensic, agriculture, drug of abuse, pharmaceutical, and/or oil/petroleum samples.

In some aspects, the materials (PDMS and PTFE) and solvent (e.g., water only solvents) used in the devices of the embodiments are biologically compatible, such that they can be used in surgery in for real-time analysis. Furthermore, because the devices can be very compact, it can be hand-held or integrated to a robotic surgical system, such as the Da Vinci surgical system (e.g., in an automated system). Thus, many regions of the human body cavity can be quickly sampled during surgery, and analyzed (e.g., by using a database of molecular signatures and machine learning algorithms). Therefore, the diagnostic results may be provided in real time for each sampled region. Exemplary devices for use in these methods are detailed below.

Figure 1B:
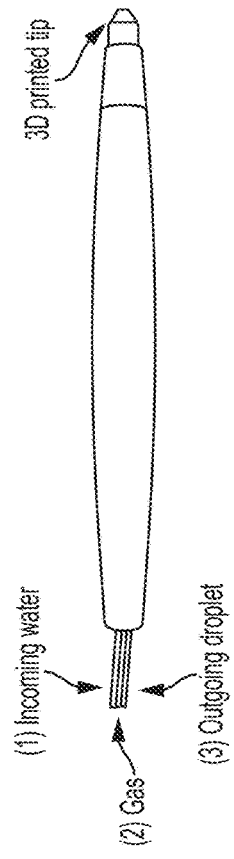
FIG. 1A-Q: Schematic representation of the MasSpec Pen system and operational steps. A) The pen-sized handheld device is directly integrated into lab-built mass spectrometer interface through PTFE tubing (or another highly hydrophobic material). The interface houses the pinch valves, microcontroller, and tubing to connect the system to the mass spectrometer inlet. The system is automatically triggered by the user through a foot pedal. B) The MasSpec Pen is designed with a PDMS 3D-printed tip and three PTFE conduits, which provide incoming water to the tip, gas, and an outgoing conduit for the water droplet. C) The tip contacts the tissue for analysis, and it designed with 3 conduits and a solvent reservoir. When the system is triggered (t=0 sec) by the use through the pedal, the syringe pump delivers a controlled volume of water to the reservoir. The discrete water droplet interacts with the tissue to extract molecules. After, in this case, 3 seconds of extraction, the vacuum and the gas conduits are concommintantly opened to transport the droplet from the MasSpec Pen to the mass spectrometer through the tubing system for molecular analysis. D) Show a schematic of the exemplary functional element of a MasSpec Pen device. E-F) Show enlarged views of the tip of an exemplary MasSpec Pen. G-Q) Show alternative configurations of a system of the embodiments.
Figure 1C:
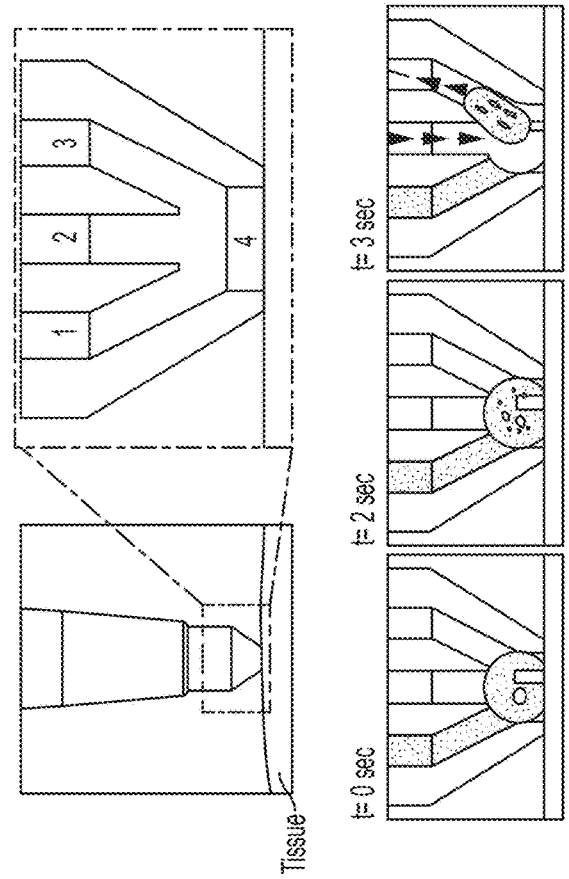
Figure 1A:
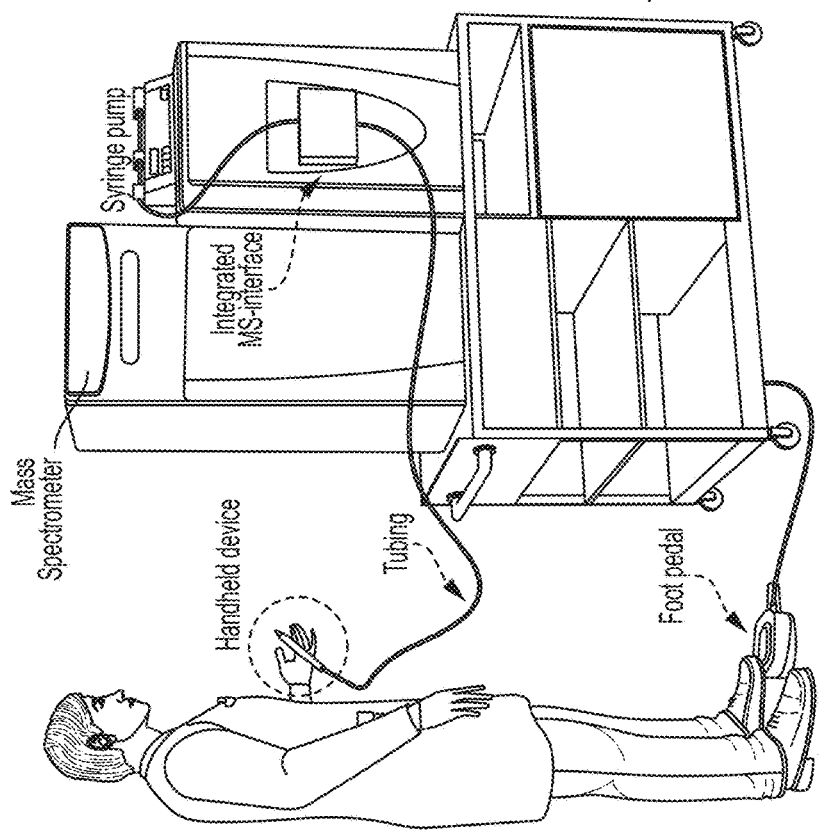
Figure 1D:
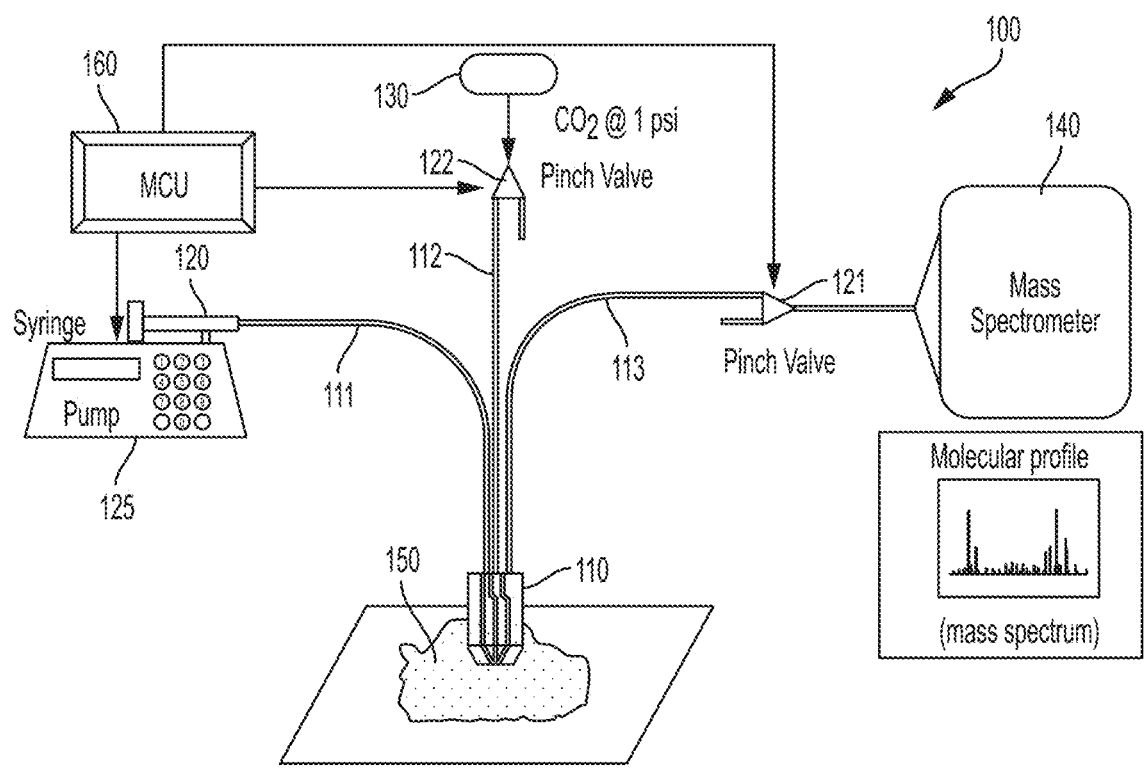

Referring initially to FIG. 1D, an apparatus 100 is shown for sampling tissue for mass spectrometry analysis. In this embodiment, apparatus 100 comprises a probe 110, a chamber 120 with solvent, a pressurized gas supply 130 and a mass spectrometer 140. In some aspects, the probe is comprised in housing (e.g., to provide a grip in the case of a hand-held device). In further aspects, the housing can comprise clicker feature (e.g., a trigger, button or pedal) that can be used to control fluid and/or gas flow through the probe. In some aspects, the probe is composed of a material comprising PDMS and/or PTFE. In some aspects, the probe is produced by a 3D printing process.

Figure 1E:
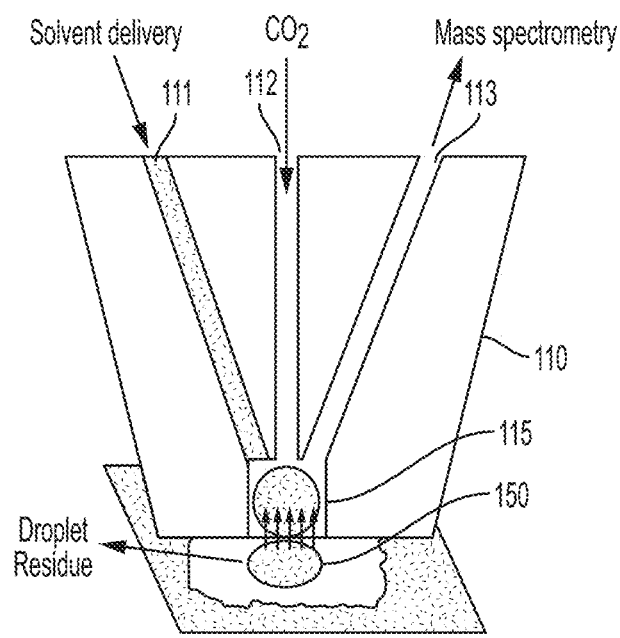
Figure 1F:
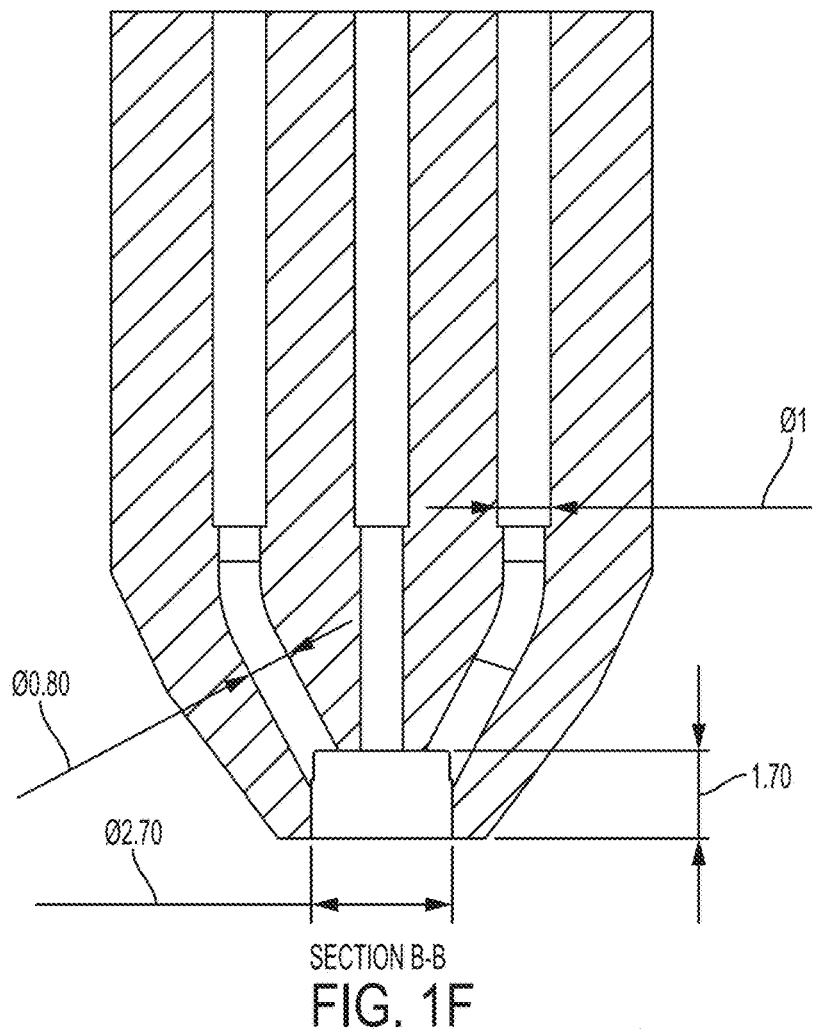

FIG. 1E provides a more detailed cross-section view of probe 110 and illustrates probe 110 comprises a first conduit 111, a second conduit 112, a third conduit 113 and a reservoir 115. In the illustrated embodiment, first conduit 111 is in fluid communication with chamber 120, second conduit 112 is in fluid communication with pressurized gas supply 130, and third conduit 113 is in fluid communication with mass spectrometer 140. FIG. 1F provides an additional cross-section view of a probe with dimensions for a particular embodiment.

It is understood that in certain embodiments, each of conduits 111, 112 and 113 (which can be of any desired length) may comprise separate components. For example, the portion of each of the conduits within probe 110 may be formed as integral channels during the manufacturing of probe 110. In addition, the portions of each of the conduits between probe 110 and chamber 120, pressurized gas supply 130 and mass spectrometer 140 may be tubing or other components suitable for providing fluid flow.

In this embodiment, apparatus 100 may comprise a pump 125 configured to transfer the solvent from chamber 120 to the first conduit 111 and reservoir 115. In the embodiment shown, apparatus 100 can also comprise a first valve 121 configured to control a sample flow from reservoir 115 through third conduit 113 to mass spectrometer 140. Apparatus 100 can also comprise a second valve 122 configured to control a flow of pressurized gas through second conduit 112 to reservoir 115.

A control system 160 can be configured to control operating parameters of apparatus 100. For example, control system 160 can be configured to control a flow of solvent from chamber 120 through first conduit 111 to reservoir 115 by controlling the operation of pump 125. In addition, control system 160 can be configured to control the sample flow from reservoir 115 to mass spectrometer 140 by controlling the opening and closing of first valve 121. Control system 160 can further be configured to control the pressurized gas flow from pressurized gas container 130 to reservoir 115 by controlling the opening and closing of second valve 122.

During operation of apparatus 100, a user can position probe 110 so that reservoir 115 is placed on sample site 150. Control system 160 can operate pump 125 for specific periods of time to transfer a desired volume of the solvent from chamber 120 to reservoir 115 via first conduit 111. In exemplary embodiments, the solvent in chamber 120 can assist in the efficient extraction of molecules from a tissue sample site 150 for analysis.

In addition, control system 160 can allow a particular period of time between the operation of pump 125 and the opening of first valve 121. This can allow a vacuum from mass spectrometer 140 (or a separate, auxiliary vacuum system) to draw sample materials (e.g. molecules from tissue sample site 150) from reservoir 115 to mass spectrometer 140 via third conduit 113.

When first valve 121 is opened, control system 160 can also open second valve 122 to allow an inert gas (e.g. $N_2$ or $CO_2$) to be transferred from pressurized gas supply 130 to reservoir 115 via second conduit 112. The inert gas can assist in sample tissue drying prior to analysis, as well as prevent a solvent gap in first conduit 111 (e.g. as a result of a vacuum pulled by mass spectrometer 140 when reservoir 115 contacts sample site 150). The inert gas can also assist in solvent transport from sample site 150 to mass spectrometer 140 through third conduit 113.

Control system 160 may comprise software and hardware suitable for operating the various components of apparatus 100. Particular embodiments of the various components shown in the schematic of FIG. 1 are provided in the examples discussed below, including the section entitled Example 1.

Figure 1G:
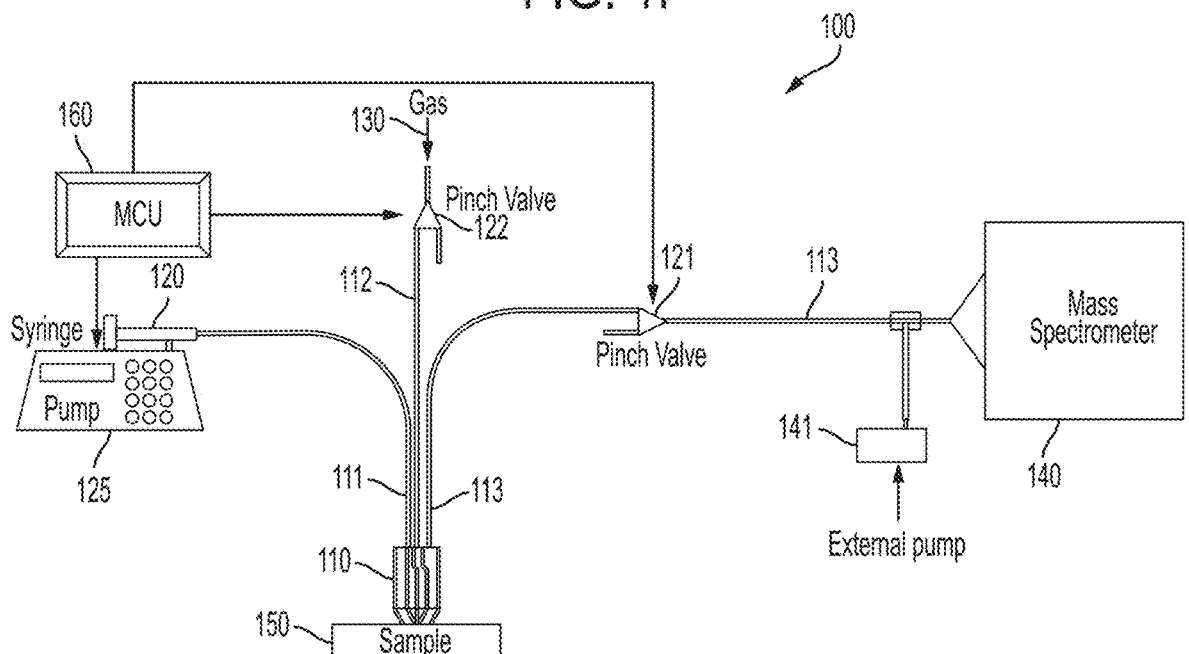
Figure 1H:
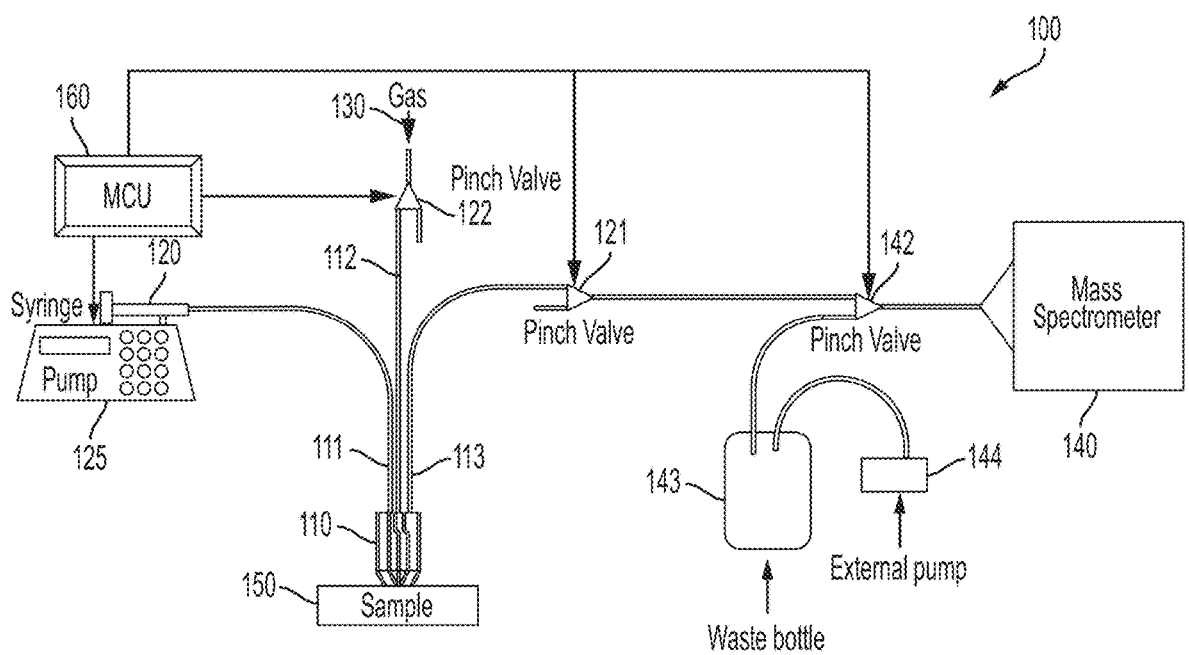

FIG. 1G illustrates an embodiment of apparatus 100 that is similar to the embodiment shown in the previous FIG. 1D. In the embodiment of FIG. 1G, however, apparatus 100 further comprises a pump 141 in fluid communication with conduit 113. In certain embodiments, pump 141 may be an external vacuum pump that can be operated to increase the velocity of the sample portion through conduit 113 to the mass spectrometer. It is understood that the components of apparatus 100 described in previous embodiments operate in an equivalent manner in this embodiment (and subsequently described embodiments). For purposes of clarity, not all components are labeled with reference numbers in each of the figures. In addition, the operational aspects of components that are equivalent to components in previously-described embodiments will not be repeated in the discussion of this or subsequent embodiments.

Figure 1I:
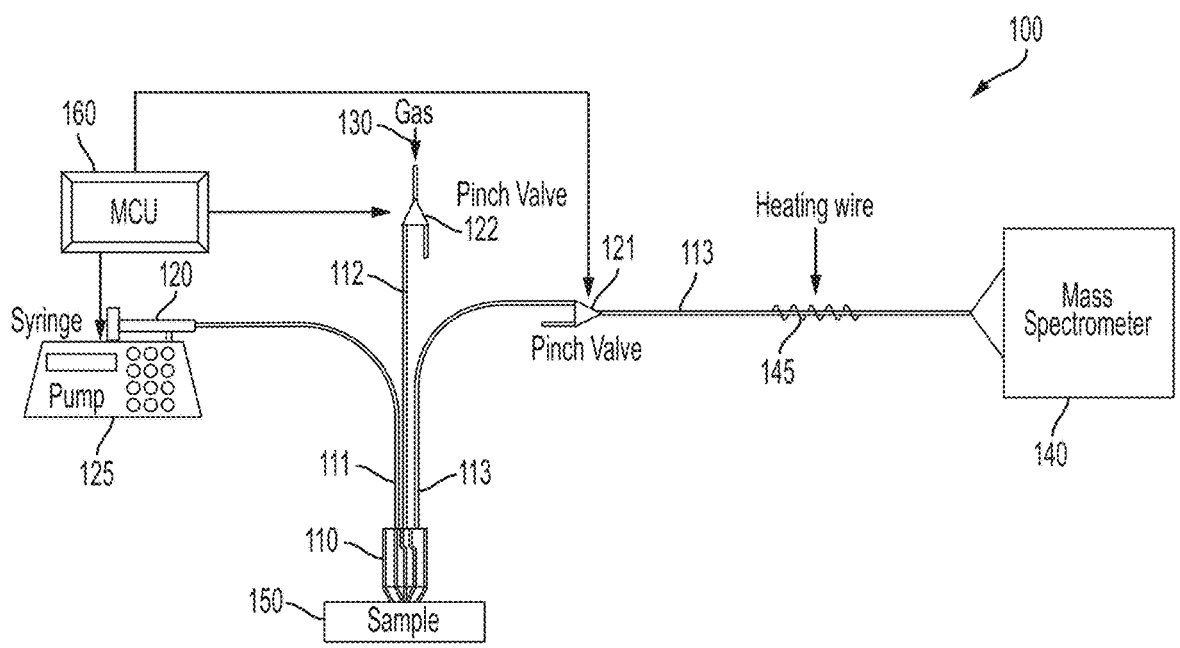

FIG. 1I1 illustrates another embodiment of apparatus 100 that is similar to the previously-described embodiments but also comprises a valve 142, a waste container 143 and a pump 144 in fluid communication with conduit 113. In certain embodiments, valve 142 may be used to diverge a solvent or other cleaning solution from conduit 113 to waste container 143 during cleaning steps. Waste container 143 can be emptied via operation of pump 144. In exemplary embodiments, cleaning or washing steps using water, ethanol, mixtures of water and ethanol at any ratio, as well as other solvent may be used at any stage of sample analysis to decrease carry over effects. In certain embodiments, probe 110 may also be switched between each use. Further, probe 110 may be inserted into a vial containing solvent for washing step using gas (bubbling) to assist with cleaning before or after the automatic wash step. Other cleaning methods including wiping with a sterile solution may also be used. For example, certain embodiments may use a cleaning protocol of: 1. Replace probe; 2. Wash with solution of 50/50 ethanol/water; 3. Wash with 100% ethanol.

FIG. 1I illustrates another embodiment of apparatus 100 that is similar to the previously-described embodiments but also comprises a heating element 145 on conduit 113. In certain embodiments, heating element 145 is configured as a heating wire that may be wrapped around conduit 113. In other embodiments may comprise different heating element configurations, including for example, ceramic heaters. Conduit 113 may be heated to improve water or solvent transport to mass spectrometer 140, as well as to assist in ionization, in any of the exemplary embodiments described herein. Heating can be implemented through the entire conduit system or at specific locations.

Figure 1J:
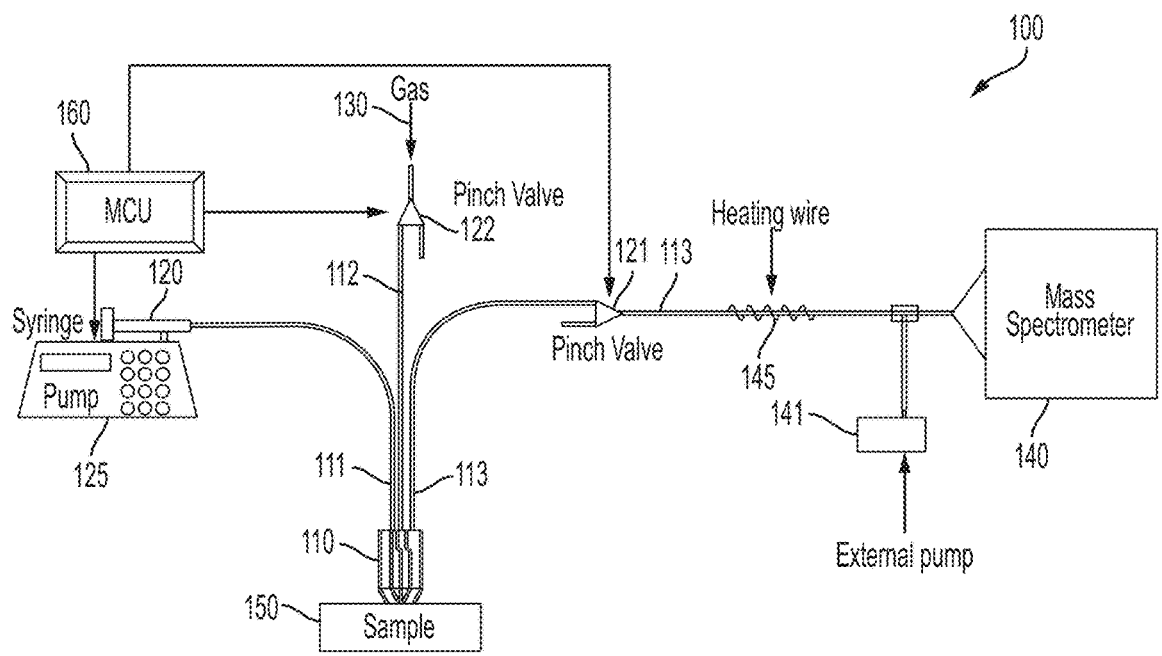

FIG. 1J illustrates an embodiment of apparatus 100 that combines features of previously-described embodiments. In particular, the embodiment shown in this figure includes heating element 145 on conduit 113 and pump 141. The operational aspects of heating element 145 and pump 141 have been previously discussed in the description of FIGS. 1I and 1G, respectively, and will not be repeated here for the sake of brevity.

Figure 1K:
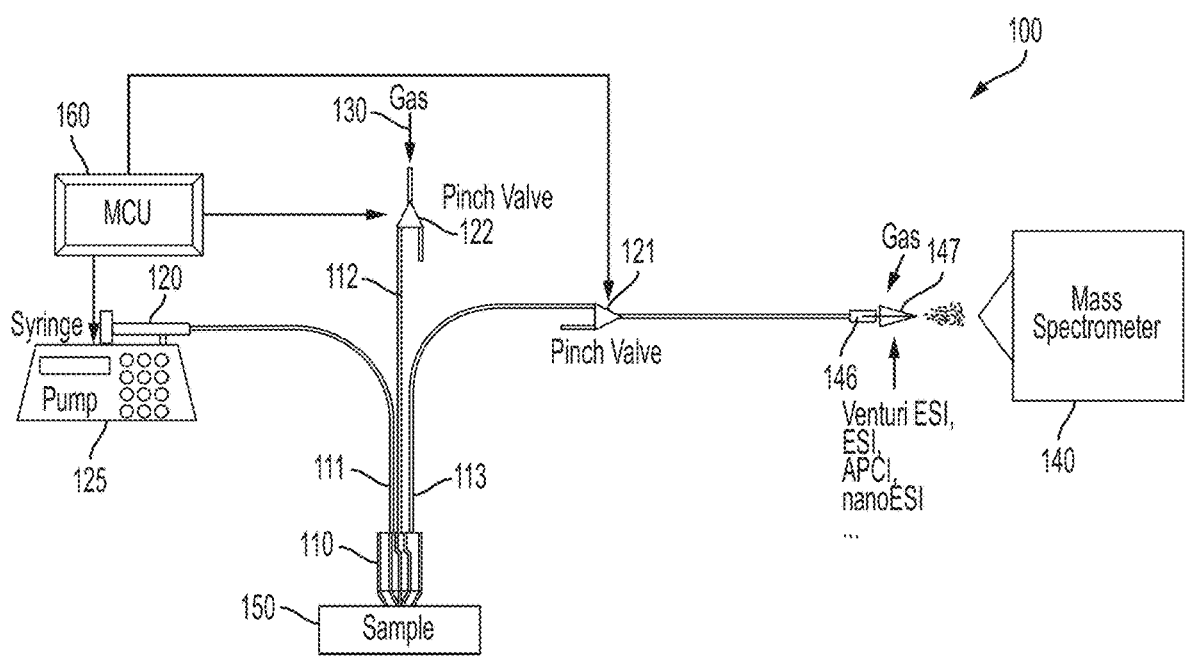
Figure 1L:
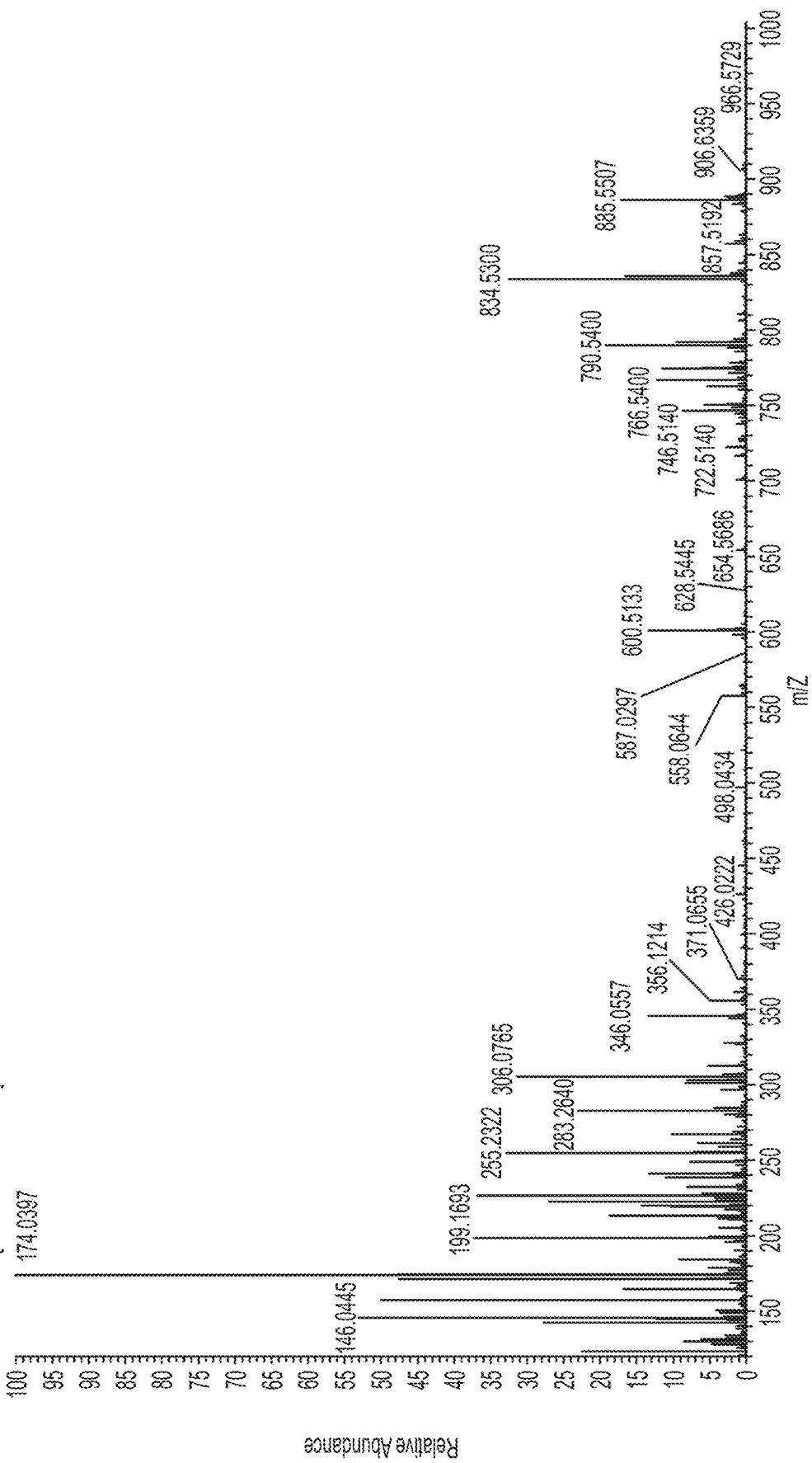

FIG. 1K illustrates an embodiment of apparatus 100 that is similar to the previously-described embodiments but also comprises an ionization device 146 to form a spray in proximal to an inlet for mass spectrometer 140. In certain embodiments, ionization device 146 may be, for example, an electrospray ionization (ESI) device, a nano ESI device, or an atmospheric pressure chemical ionization (APCI) device. In particular embodiments, conduit 113 is not directly connected to mass spectrometer 140 and a venturi device 147 can be used to transport a droplet of sample 150 to ionization device 146 and the interface of mass spectrometer 140. A mass spectrometry profile is shown in FIG. 1L of an embodiment of apparatus 100 including a venturi device. As shown in FIG. 1L, the profile obtained is similar to embodiments directly coupling conduit 113 to the inlet of mass spectrometer 140.

Figure 1M:
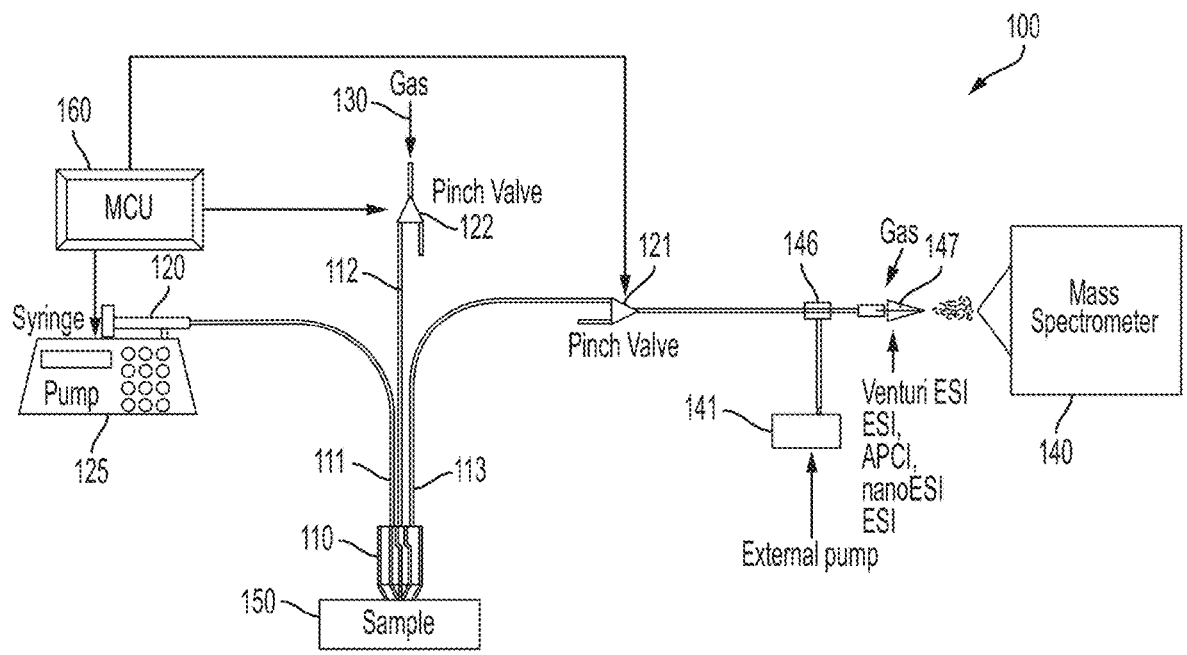

Referring now to FIG. 1M, an embodiment of apparatus 100 includes external pump 141 (as previously shown and described in FIG. 1G) and ionization device 146 and venturi device 147 as shown (as previously shown and described in FIG. 1K).

Figure 1N:
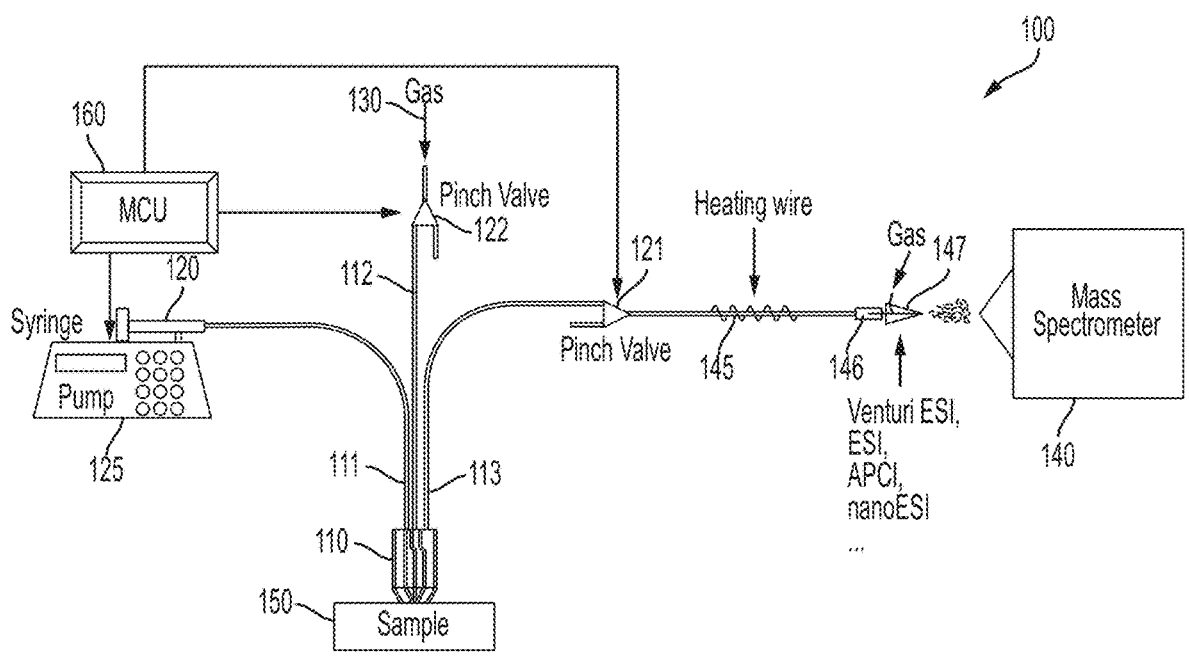

As shown in the embodiment of FIG. 1N, an embodiment of apparatus 100 includes heating element 145 (as previously shown and described in FIG. 1I) and ionization device 146 and venturi device 147 as shown (as previously shown and described in FIG. 1K).

Figure 1O:
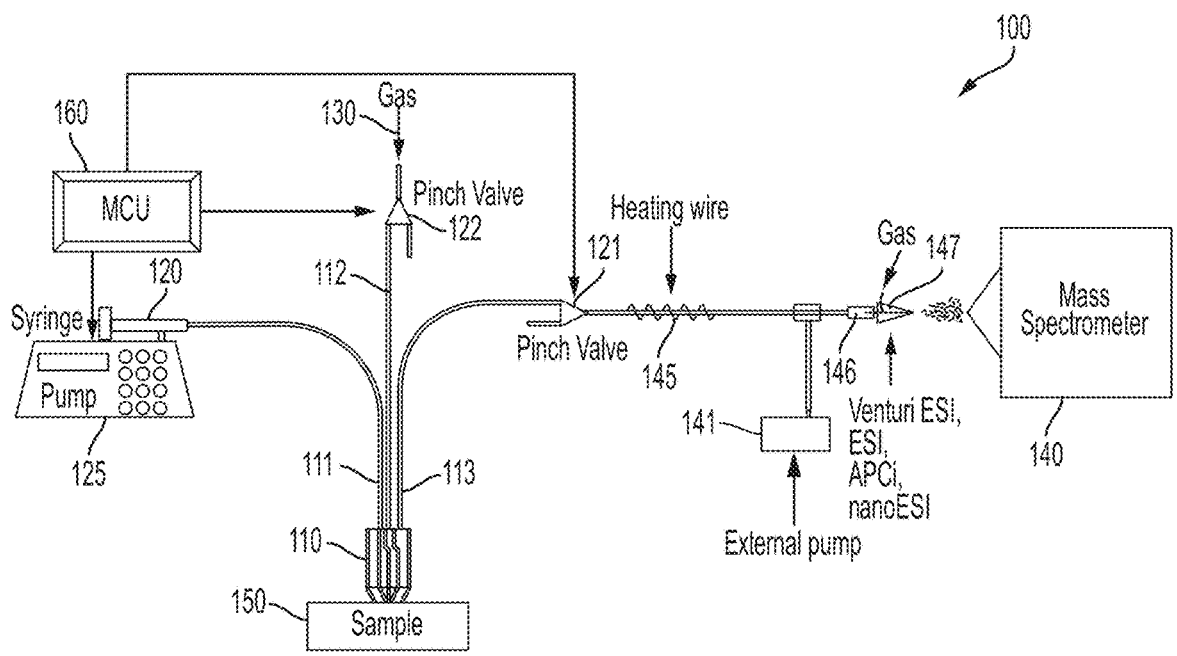

As shown in the embodiment of FIG. 1O, an embodiment of apparatus 100 includes heating element 145 (as previously shown and described in FIG. 1I) and ionization device 146 and venturi device 147 as shown (as previously shown and described in FIG. 1K). In addition, this embodiment also includes external pump 141 (as previously shown and described in FIG. 1G).

Figure 1P:
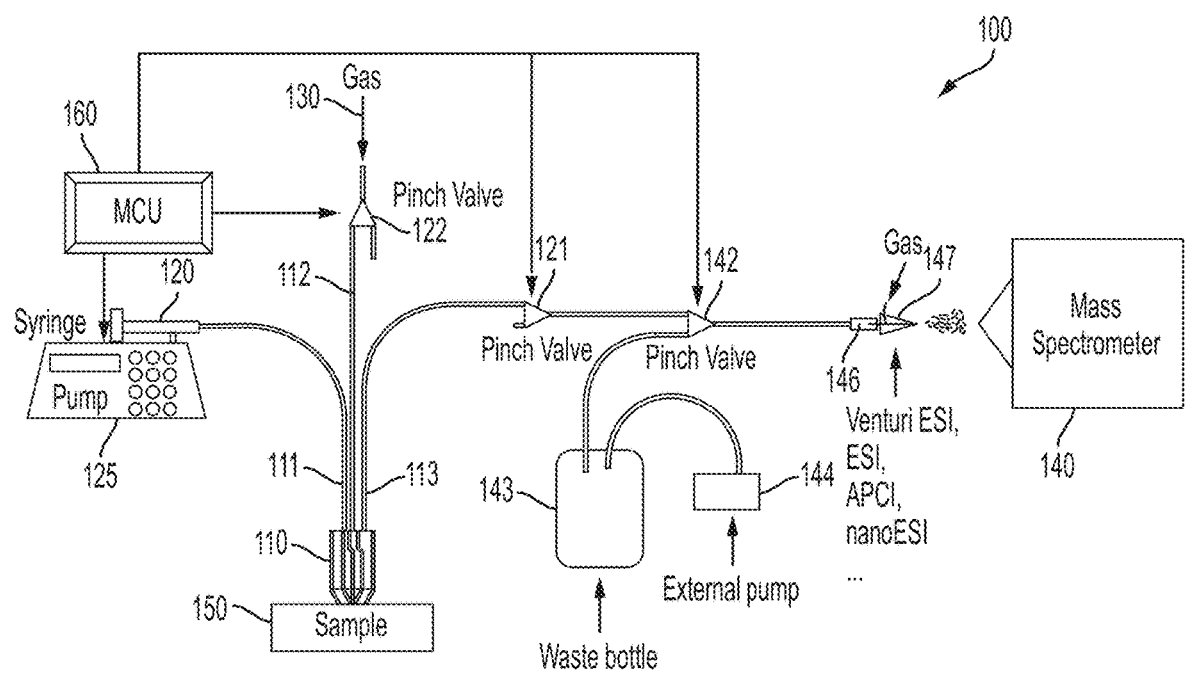

As shown in the embodiment of FIG. 1P, an embodiment of apparatus 100 includes valve 142, waste container 143 and pump 144 (as previously shown and described in FIG. 1I1). In addition, this embodiment also includes ionization device 146 and venturi device 147 as shown (as previously shown and described in FIG. 1K).

Figure 1Q:
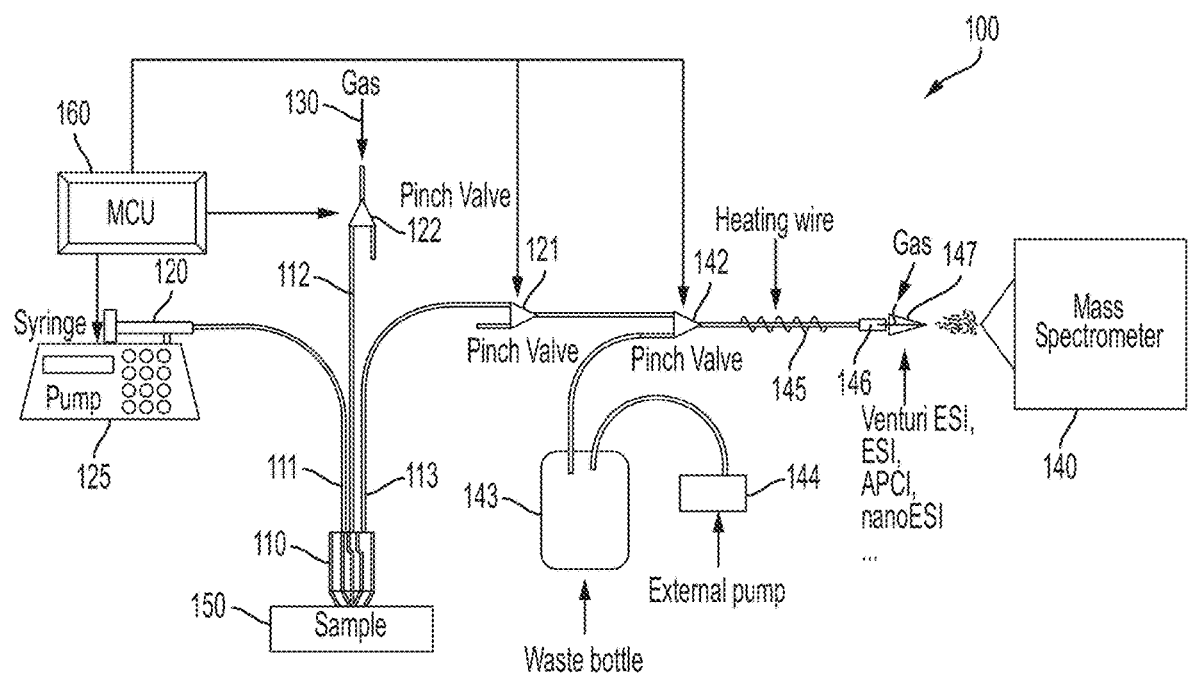

As shown in the embodiment of FIG. 1Q, an embodiment of apparatus 100 includes valve 142, waste container 143 and pump 144 (as previously shown and described in FIG. 1I1). In addition, this embodiment also includes ionization device 146 and venturi device 147 as shown (as previously shown and described in FIG. 1K). This embodiment further includes heating element 145 (as previously shown and described in FIG. 1I).

II. Assay Methodologies

In some aspects, the present disclosure provides methods of determining the presence of diseased tissue (e.g., tumor tissue) or detecting a molecular signature of a biological specimen by identifying specific patterns of a mass spectrometry profile. Biological specimens for analysis can be from animals, plants or any material (living or non-living) that has been in contact with biological molecules or organisms. A biological specimen can be samples in vivo (e.g. during surgery) or ex vivo.

A profile obtained by the methods of the embodiments can correspond to, for example, proteins, metabolites, or lipids from analyzed biological specimens or tissue sites. These patterns may be determined by measuring the presence of specific ions using mass spectrometry. Some non-limiting examples of ionizations methods that can be coupled to this device include chemical ionization, laser ionization, atmospheric-pressure chemical ionization, electron ionization, fast atom bombardment, electrospray ionization, thermal ionization. Additional ionization methods include inductively coupled plasma sources, photoionization, glow discharge, field desorption, thermospray, desorption/ionization on silicon, direct analysis in real time, secondary ion mass spectroscopy, spark ionization, and thermal ionization.

In particular, the present methods may be applied or coupled to an ambient ionization source or method for obtaining the mass spectral data such as extraction ambient ionization source. Extraction ambient ionization sources are methods with, in this case, liquid extraction processes dynamically followed by ionization. Some non-limiting examples of extraction ambient ionization sources include air flow-assisted desorption electrospray ionization (AFADESI), direct analysis in real time (DART), desorption electrospray ionization (DESI), desorption ionization by charge exchange (DICE), electrode-assisted desorption electrospray ionization (EADESI), electrospray laser desorption ionization (ELDI), electrostatic spray ionization (ESTASI), Jet desorption electrospray ionization (JeDI), laser assisted desorption electrospray ionization (LADESI), laser desorption electrospray ionization (LDESI), matrix-assisted laser desorption electrospray ionization (MALDESI), nanospray desorption electrospray ionization (nano-DESI), or transmission mode desorption electrospray ionization (TM-DESI).

As with many mass spectrometry methods, ionization efficiency can be optimized by modifying the collection or solvent conditions such as the solvent components, the pH, the gas flow rates, the applied voltage, and other aspects which affect ionization of the sample solution. In particular, the present methods contemplate the use of a solvent or solution which is compatible with human issue. Some non-limiting examples of solvent which may be used as the ionization solvent include water, ethanol, methanol, acetonitrile, dimethylformamide, an acid, or a mixture thereof. In some embodiments, the method contemplates a mixture of acetonitrile and dimethylformamide. The amounts of acetonitrile and dimethylformamide may be varied to enhance the extraction of the analytes from the sample as well as increase the ionization and volatility of the sample. In some embodiments, the composition contains from about 5:1 (v/v) dimethylformamide:acetonitrile to about 1:5 (v/v) dimethylformamide:acetonitrile such as 1:1 (v/v) dimethylformamide:acetonitrile. However, in preferred embodiment the solvent for use according to the embodiments is a pharmaceutically acceptable solvent, such as sterile water or a buffered aqueous solution.

III. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Smart MasSpec Pen Design

The MasSpec Pen (FIG. 1A) was developed as an automated and biocompatible handheld sampling probe that allows gentle, time- and volume-controlled extraction of molecules from a tissue sample using a discrete water droplet. Several prototypes of the system were engineered with the goal of minimizing tissue damage, maximizing tissue-analyte extraction, and maximizing solvent transfer to the mass spectrometer.

The system developed consists of three main parts: 1) a syringe pump that is programmed to deliver a discrete solvent volume using a controlled flow rate; 2) tubing systems integrated to two-way pinch valves for controlled solvent transport; 3) a probe tip which is used for direct sampling of biological tissues. Several iterations of the system were explored and optimized with the ultimate goal of minimizing tissue damage, maximizing tissue-analyte extraction, and maximizing solvent transmission to the mass spectrometer. FIG. 1A shows a schematic figure of one example of an apparatus comprising a Diagnostic Pen (MasSpec Pen) device for analyzing biological tissue.

The optimized system contains three primary components: 1) a syringe pump that is programmed to deliver a defined water volume (4-10 µL) to the sampling probe; 2) small diameter (ID 800 µm) polytetrafluoroethylene (PTFE) tubing conduits which are integrated to a fast (8 ms) two-way pinch valves for controlled solvent transport from pump to tissue, and from the tissue to the mass spectrometer; 3) a handheld pen-sized probe for direct sampling of biological tissues.

Figure 22:
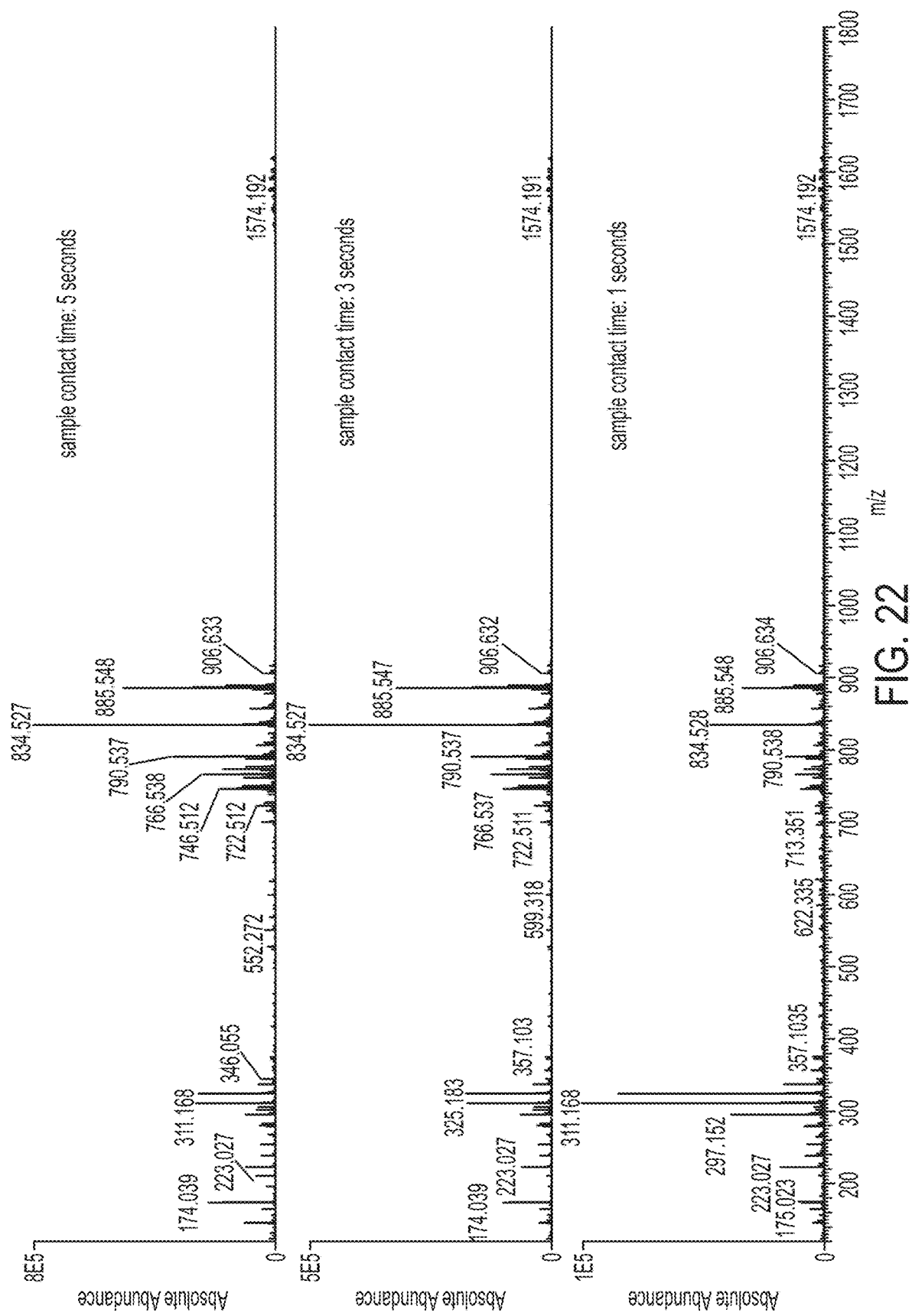
FIG. 22: Representative negative ion mode mass spectra obtained from a mouse brain tissue sections with different extraction times, 5 s, 3 s, and 1 s.

The main component of the handheld pen-sized probe is a 3D-printed polydimethylsiloxane (PDMS) tip (FIG. 1B) in which the solvent is retained during interaction with the tissue. The tip was manufactured using 3D-printing and is made of biologically compatible polydimethylsiloxane (PDMS). The tip is designed with three main ports: one for the incoming (solvent) conduit system (tube 111 or conduit 1), a central port for gas (N2, CO2 or air) delivery (tube 112 or conduit 2), and an outgoing port to transport molecular constituents in the water droplet from tissue to the mass spectrometer (tube 113 or conduit 3). At the probe tip, all ports combine into a small reservoir where the single droplet is retained and exposed to the tissue sample for a controlled amount of time (3 s), allowing efficient analyte extraction. The diameter of the reservoir determines the volume of solvent exposed to the tissue as well as the spatial resolution of the device. Using current tooling, MasSpec Pen tips were designed with sampling sizes ranging from 1.5 mm to 5.0 mm, which is determined by the reservoir diameter. At a 2.77 mm reservoir diameter, a solvent volume of 10 µL is retained in the reservoir and contacted to the tissue sample for a defined time period, while 4.4 µL are retained in a reservoir with a 1.5 mm diameter. After the 3 s extraction period, the MasSpec Pen is removed from the tissue. Concomitantly, conduit 3 is opened allowing vacuum extraction of the droplet to the mass spectrometer, a positive pressure from a low-pressure gas delivery (<10 psi) is provided through conduit 2, followed by a flush step to clean the system. Note that contact times of 1 second, 3 seconds and 5 seconds between the droplet and the tissue sample were evaluated (FIG. 22). The 3 seconds contact time was selected for all the experiments as it allowed ease of operation by the user and yielded mass spectra with sufficient total ion intensity. The gas provided by the second tube does not participate in the extraction process, but is used instead to prevent collapse of the system due to the vacuum employed and to assist solvent transport from tissue to the mass spectrometer. Similarly, the flush step is not used for extraction of biomolecules from tissues as there is no contact with tissue during this period. Conduit 3 is directly connected to the transfer tube of a high mass-resolution Orbitrap mass spectrometer so that the negative pressure of the mass spectrometer vacuum system drives movement of the droplet from the reservoir to the mass spectrometer for ionization and mass analysis. This set up simplifies the operational steps and precludes the use of ionization sources, although various connection and ionization methods could be coupled to our system. A tube length of 1.5 meters was employed for all the conduits to allow free handheld use of the device by an operator without geometrical or spatial constraints.

The three conduit tubes used are made of polytetrafluoroethylene (PTFE), which is also biologically compatible. Tube 111 is used to deliver solvent from syringe pump to the probe tip. Tube 112 is used, in some cases, to deliver an inert gas ($N_2$ or $CO_2$) to the probe tip. The gas serves three main purposes: 1) tissue drying prior to analysis; 2) prevent solvent gap in tube 111 due to the mass spectrometer's vacuum when the reservoir is closed by contacting the tissue specimen; 2) assist solvent transport from tissue to the mass spectrometer through tube 113. However, in some circumstances there is no need for use of a gas. Tube 113 is directly connected to the inlet of the mass spectrometer so that the positive pressure of the mass spectrometer vacuum system is used to drive the droplet from the reservoir to the mass spectrometer inlet for ionization.

The time events involved in the device operation are automated and precisely controlled by software that communicates with an Arduino system and two two-way pinch valves. All pinch valves are closed until the process is initiated when: 1. under 300 µL/min, a pulse is sent to the pump to infuse the solvent for two seconds and stop, generating a 10 µL droplet filling in the MasSpec Pen reservoir; 2. Tubes 112 and 113 are closed, allowing the solvent in the reservoir to interact with the tissue for three seconds to extract the molecules; 3. The pinch valves controlling tubes 112 and 113 are opened simultaneously, allowing the droplet to transfer to the mass spectrometer for ionization and molecular analysis. 4. A pulse is sent to the pump to infuse the solvent for another 12 seconds and stop, to completely drive all the extracted molecules into the mass spectrometer. 5. Leave tube 112 and 113 open for another 20 seconds to allow all the solvent in tube 113 to go into the mass spectrometry. The total analyzing time is 37 seconds.

The tip design using three conduit tubes and high speed actuated pinch valves allowed precise control of droplet motion and showed excellent performance and robustness. The entire process from sampling to mass spectral acquisition is completed in 10 s or less and is fully automated using an Arduino microcontroller, so that each acquisition and analysis is individually triggered through a one-step click using a foot pedal. System automation ensures that each solvent droplet is delivered separately to the inlet, yielding several mass spectra that are averaged for a final molecular profile of the sample. Further, controlled droplet delivery allowed the mass spectrometer to operate without any evident performance degradation. After each use, the MasSpec Pen can be cleaned if residues are observed through a rapid and automated cleaning flush, or by replacing the disposable tip.

EXAMPLE 2

Molecular Profiles and Analysis

Figure 3A:
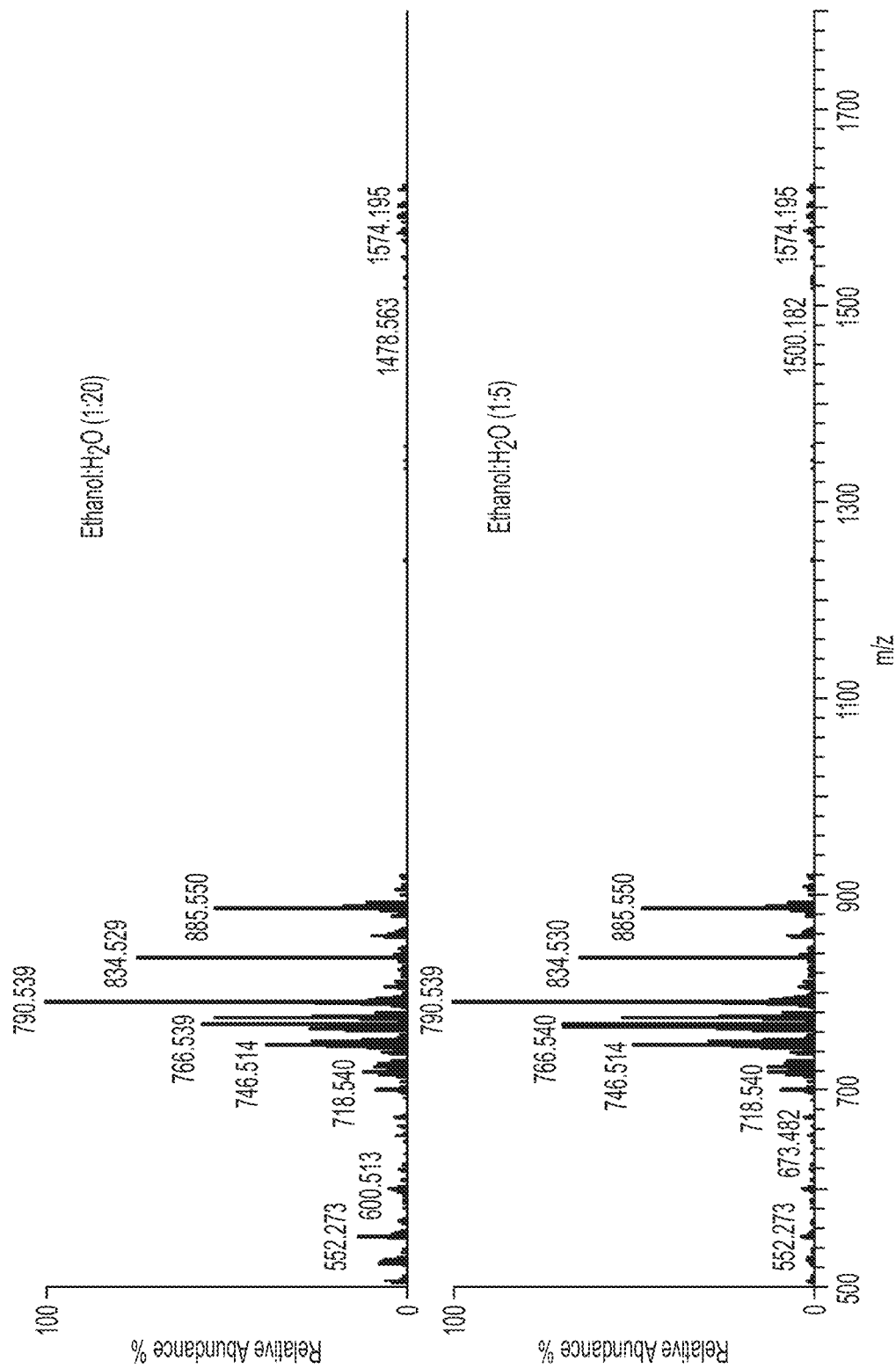
FIGS. 3A-3B: A) Shows a comparison of mass spectra of biological samples that was obtained using a solvent composed of ethanol:$H_2O$ (1:20) or ethanol:$H_2O$ (1:5). B) Representative negative ion mode MasSpec Pen mass spectra obtained from mouse brain tissue sections using mixtures of water and ethanol at various ratios.

The system described herein operates by directly connecting the collection conduit to the mass spectrometer inlet for transporting the analyte-containing solvents to the mass spectrometer for molecular analysis. This set up greatly simplifies operational details and precludes the use of ionization sources. After the probe interacts with the tissue, the solvent is then transported to the mass spectrometer and directly infused without the need of an additional ionization source. Since the system is fully automated so that each 10 µL solvent droplet is delivered separately to the inlet, the mass spectrometer operates without any impact on its performance. Rich molecular information is obtained in this manner, similar to what is observed from other solvent-extraction ambient ionization techniques such as desorption electrospray ionization. The ionization mechanism may be similar to inlet ionization. For inlet ionization methods, the ionization occurs in the inlet pressure drop region between atmosphere and vacuum. Several solvent systems can be used in the device. In this example, to assure full biological compatibility of the device, water was used as the only solvent, although mixtures of ethanol and water in different ratios were also explored and yielded similar results. To demonstrate these samples were analyzed after extraction with a solvent composed of 5:1 and 20:1 ($H_2O$:EtOH) and found out EtOH will help extract more PE lipids, like PE (40:6) (m/z 790.539) and PE (38:4) (m/z 766.540) (see results in FIG. 3).

Figure 2A:
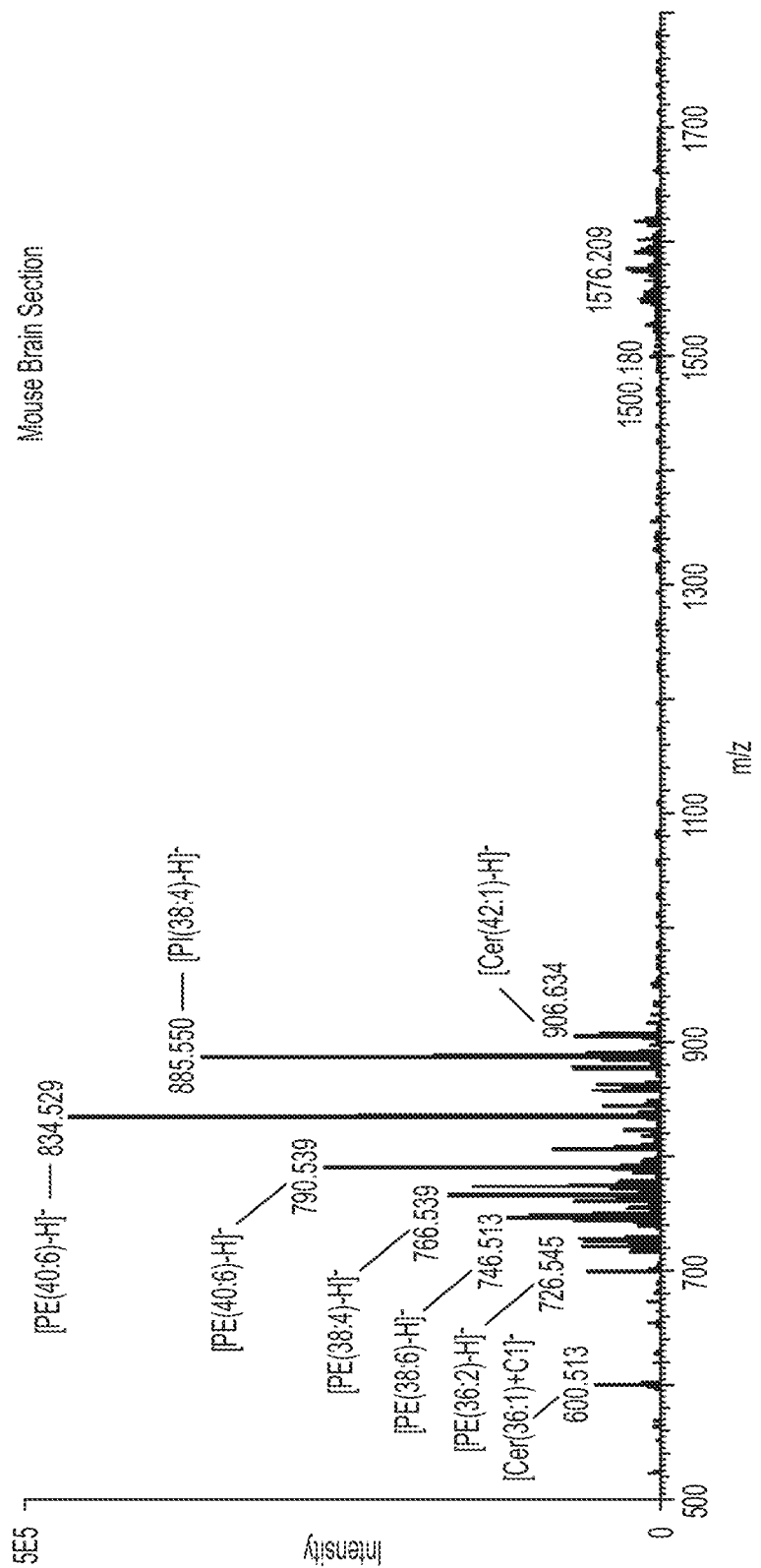
FIGS. 2A-2B: Mass spectra of mouse brain tissue section from MasSpec Pen using Q Exactive Orbitrap Mass Spectrometer. A) Mass spectrum of mouse brain section, B) Total ion chromatography, the inset spectrum is from the clean glass slide background (the intensity scale of the background and mouse brain tissue were set to be the same).
Figure 17:
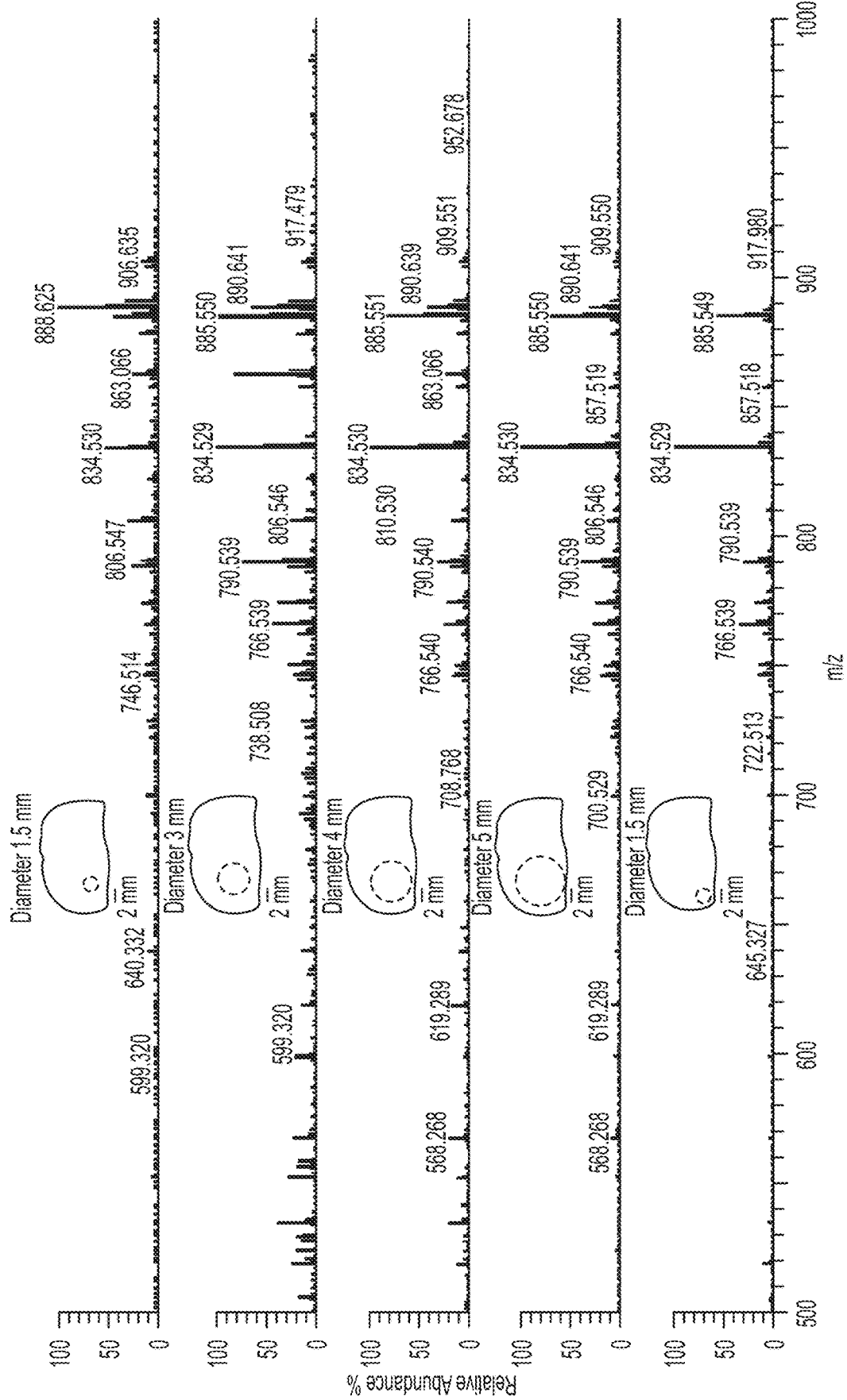
FIG. 17: Representative negative ion mode MasSpec Pen mass spectra obtained using various sampling diameters of the MasSpec Pen.

The effectiveness of the MasSpec Pen in obtaining molecular information was tested by analyzing thin tissue sections and pieces of tissue samples. First, 16 µm thick tissue sections were analyzed on standard histologic glass slides following the automated operational steps described above for the MasSpec Pen, using pure water as the solvent. Several probe tips with different reservoir diameters of the MasSpec Pen were tested, yielding mass spectra presenting lipids species characteristic of mouse brain tissue grey matter, white matter, or mixed composition for larger sampling sizes. FIG. 2 shows a representative mass spectra obtained in the negative ion mode using a 2.7 mm pen tip from the grey matter region of a mouse brain tissue section, and a representative background mass spectra obtained from a region of glass slide (no sample). Several diameters of the MasSpec Pen were tested, yielding similar mass spectra profiles with increasing total ion count observed for larger pen tip diameters (FIG. 17).

Figure 2B:
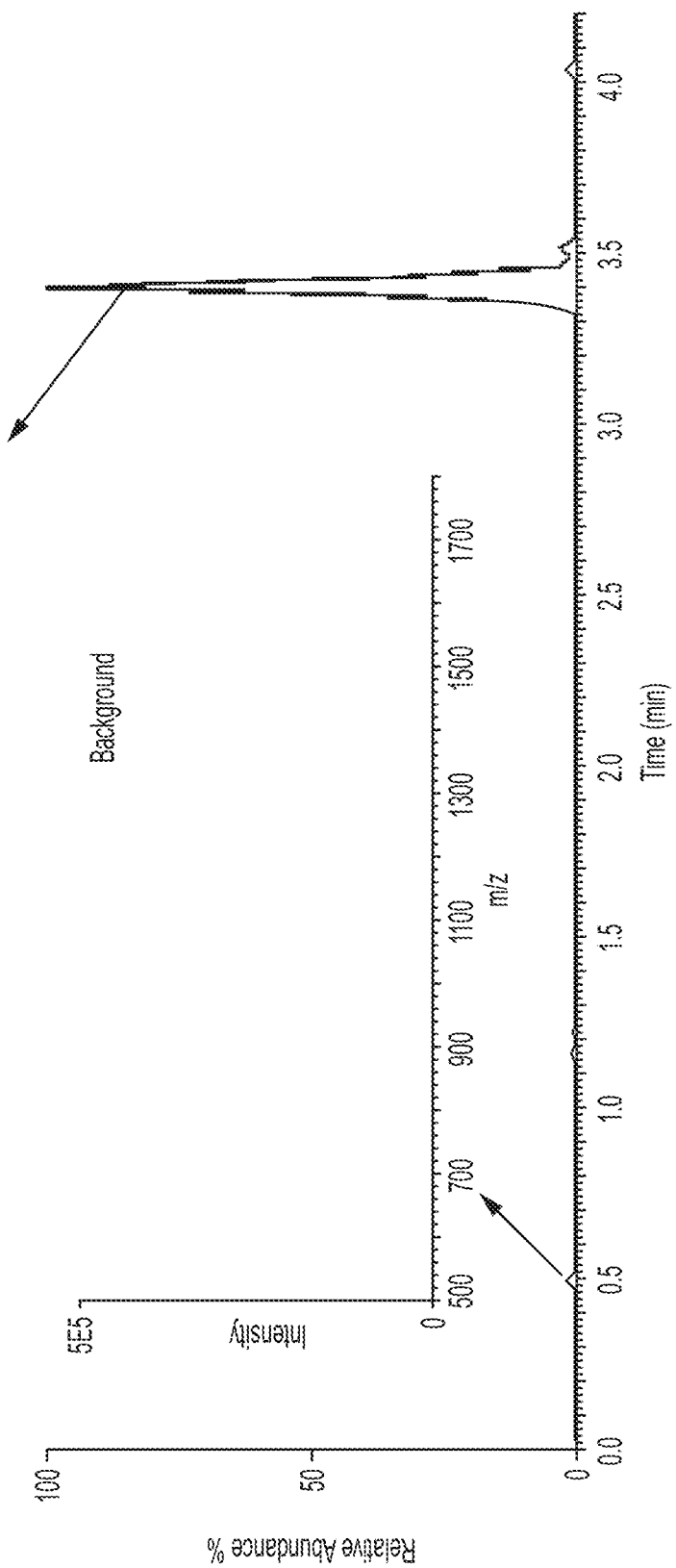

FIG. 2B shows the total ion chromatogram obtained during the total analysis period. At 0.5 min (see inset in FIG. 2B), the background mass spectrum was acquired by contacting pure glass. As seen in the mass spectrum, a remarkably clean background signal was obtained at this mass range. At 3.4 min (FIG. 2A), the MasSpec Pen was applied to a mouse brain tissue section following the same procedures discussed above. Remarkably, rich molecular profiles were observed. Lipid signals commonly detected using ambient ionization mass spectrometry of biological tissues were observed at high relative intensities in the negative ion mode mass spectrum, including fatty acids (FA), ceramides (Cer), glycerophosphoinositols (PI), glycerophosphoethanolamines (PE), glycerophosphoserines (PS) and sterol lipids (ST). Primary and secondary endogenous metabolites were also observed in the mass spectra. In the positive ion mode, diradylglycerols (DG), glycerophosphocholine (PC) and phosphosphingolipids (SM) were also detected. High resolving powder mass analyzer (resolving power was set as 140,000) were utilized to identify most of the lipids in the spectrum.

Figure 18:
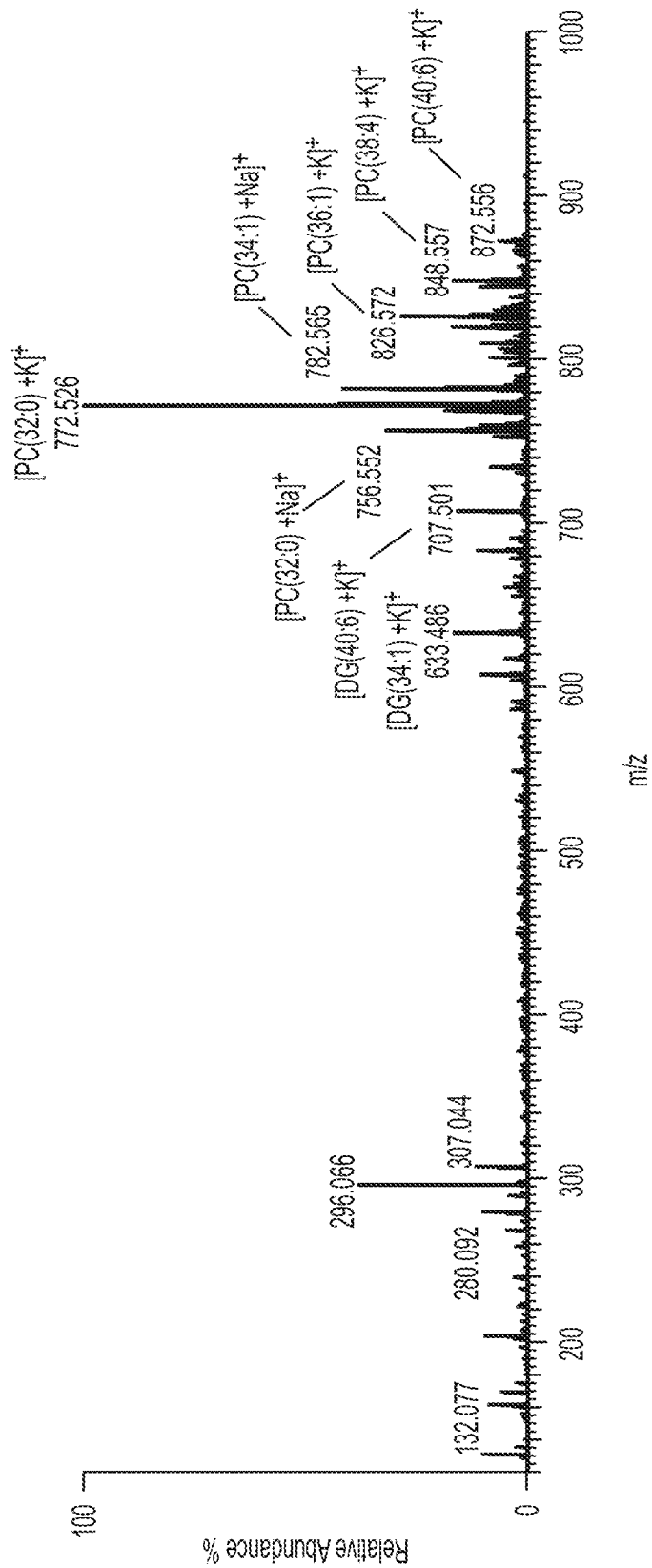
FIG. 18: Representative positive ion mode mass spectra from mouse brain tissue. Ions observed at high relative abundances were identified using tandem mass spectrometry as potassium (K+) and sodium (Na+) adducts of glycerophosphocholines and diacylglycerides lipids, as annotated in the mass spectra.

The negative ion mode mass spectra obtained from the grey matter region of the mouse brain tissue section presented rich molecular information including a variety of ions corresponding to deprotonated or chloride adducts of lipid species commonly detected from biological tissues using solvent-based ambient ionization MS techniques. Peaks at high relative abundancies were identified as fatty acids (FA) from m/z 120-350, sphingolipids such as sulfatides from m/z 700-1100 and chloride adducts of ceramides (Cer) from m/z 500-700, and glycerophospholipids (GL) such as glycerophosphoinositols (PI), glycerophosphoethanolamines (PE), glycerophosphoserines (PS) and doubly charged cardiolipins (CL) from m/z 700-1100. In the higher mass range from m/z 1100-1800, GL dimers and singly charged CL were observed. A variety of peaks tentatively identified as small metabolites including glutamine at m/z 145.061, glutamate at m/z 146.045, N-acetylaspartic acid at m/z 174.041 and chloride adduct of hexose at m/z 215.033 were detected in lower mass range from m/z 120-250, based on high mass accuracy measurements and tandem mass spectrometry data (Table 1). Importantly, the negative ion mode mass spectra obtained from the grey matter from different tissue sections of the same mouse brain were reproducible (RSD=9.3%, n=9), comparable to what reported using the same method for DESI-MSI (RSD=8.0%, n=5) In the positive ion mode, the mass spectra obtained presented high relative abundances of commonly observed molecular species identified as diacylglycerols (DG), PE, and glycerophosphocholine (PC) (FIG. 18). Tentative assignments were performed using high mass accuracy measurements, as well as tandem MS analysis when adequate intensity of fragment ions was achieved for structural interpretation. Mass errors and the m/z of fragment ions obtained by tandem MS experiments are described for all the species identified throughout the manuscript in Tables 1, 2, 3, 4 and 5. Note that isomerism of the double bonds in the FA chains of complex lipids complicates precise structural assignment, which is why FA chains are tentatively assigned for lipid species (Dill et al., *Analytical and Bioanalytical Chemistry*, 12, 2011).

Figure 6A:
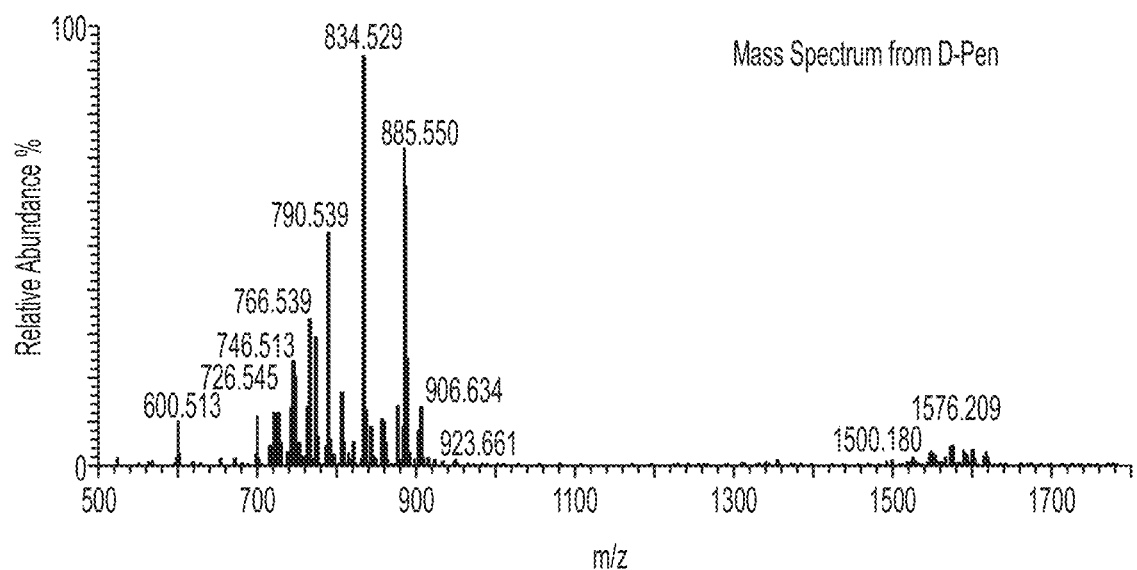
FIGS. 6A-6C: Comparison of mass spectra collected from A) MasSpec Pen and B) DESI. C) Comparison between MasSpec Pen and DESI negative ion mode mass spectra obtained from a mouse brain tissue section.
Figure 6B:
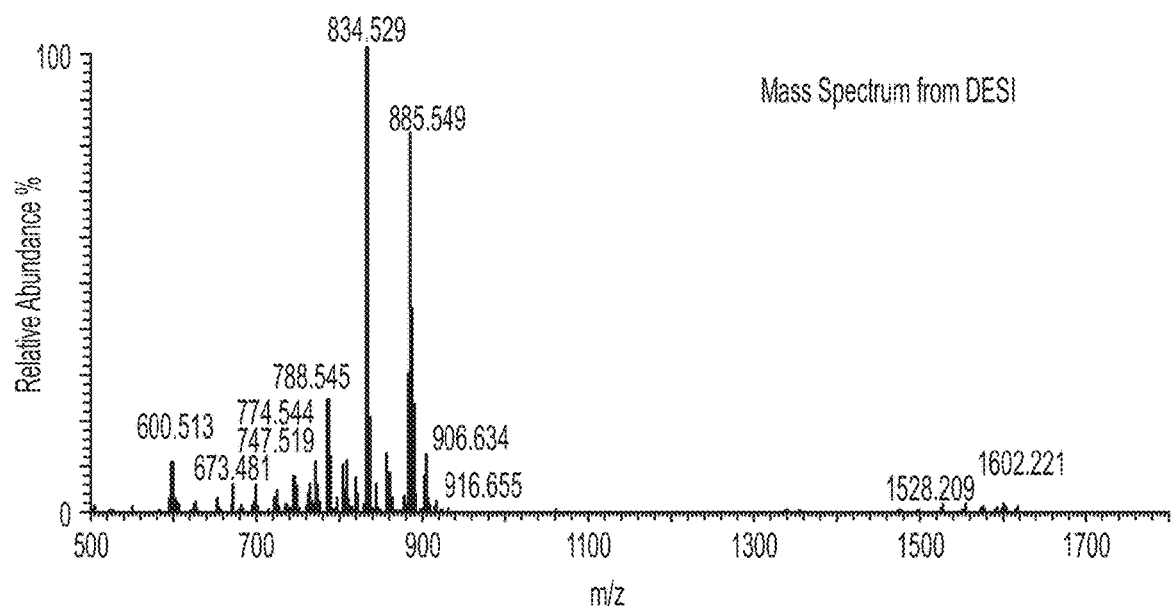

The MasSpec Pen spectrum was compared with the DESI spectrum which was acquired under similar MS parameters but using the commonly applied acetonitrile and dimethylformamide solvent system due to its high efficiency for extracting lipids from biological tissue. Interestingly, in the negative ion mode, the spectrum from MasSpec Pen using water as the extraction solvent shared large amount of molecular species from m/z 500 to m/z 1800 with the spectrum from DESI using ACN and DMF, with slightly higher ratios of PE lipids, such as PE (40:6) (m/z 790.539) and PE (38:4) (m/z 766.539). FIGS. 6A-B shows that PI (38:4) (m/z 885.550) and PS (38:6) (m/z 834.529) were the dominant peaks in both the spectra from MasSpec Pen and DESI. Moreover, in the spectra, a group of ions with higher m/z were witnessed in the mass range from m/z 1500 to m/z 1600, which were tentatively assigned to be singly charged cardiolipins (CL) and/or glycerophospholipid dimers.

Figure 3B:
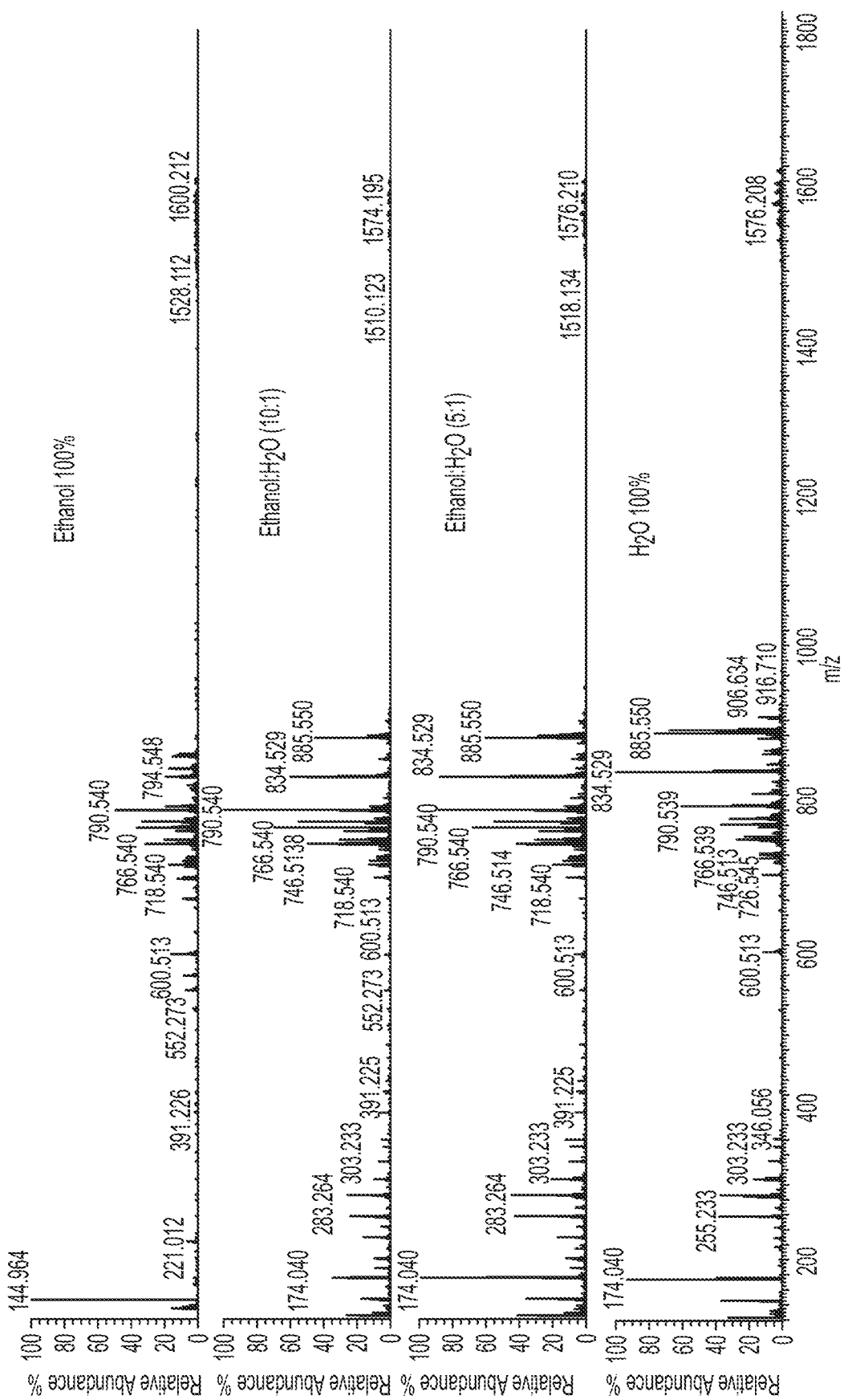
Figure 6C:
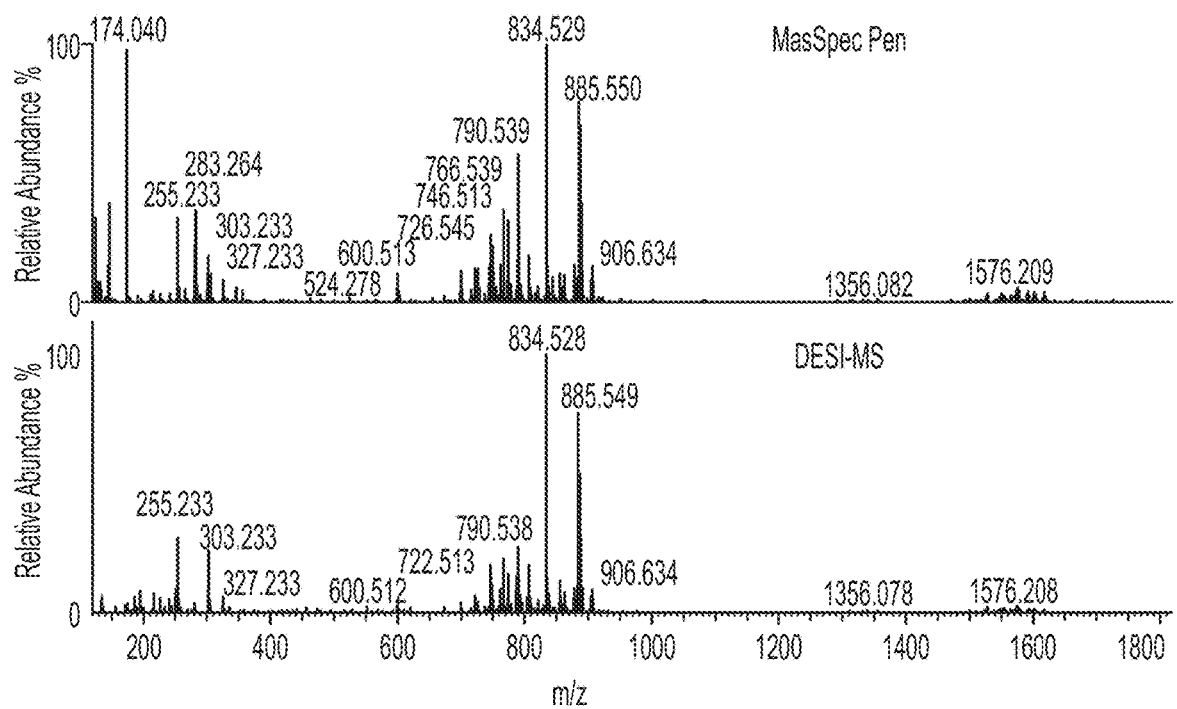

Further analysis compared the molecular species detected in the negative ion mode with those observed in a DESI mass spectrum acquired from a serial tissue section of the same mouse brain using water as the solvent and analogous experimental conditions. The mass spectra obtained using the MasSpec Pen and DESI were similar with a calculated cosine similarity of 0.9, sharing a large number of molecular species at comparable relative abundances and signal-to-noise (SN) ratios (FIG. 6C). Other solvent systems including mixtures of water with ethanol at various ratios were also explored as solvent systems for the MasSpec Pen. The mass spectra obtained presented similar lipid species to those observed in the mass spectra obtained using pure water, with variations in their relative abundances (FIG. 3B). Thus, to ensure full biocompatibility of the device, water was selected as the solvent for all the following MasSpec Pen experiments performed.

To evaluate the system performance, consecutive analysis was conducted on the same tissue section and different tissue sections and demonstrated that the system is highly reproducible within samples and across different samples.

Figure 7:
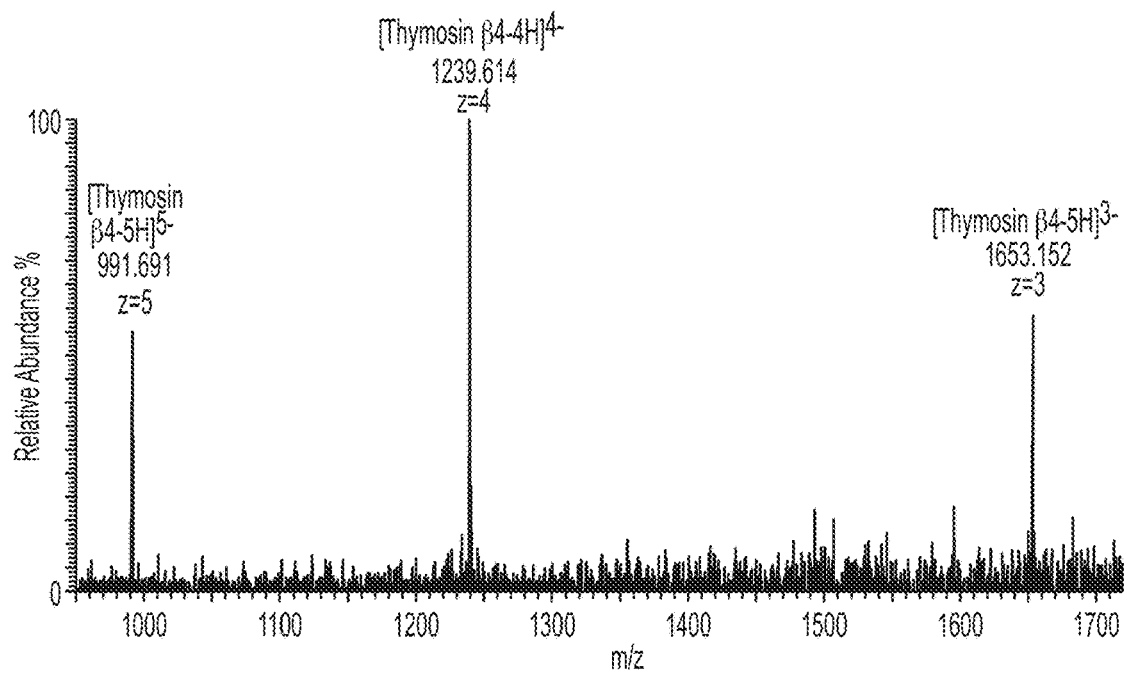
FIG. 7: The spectrum of thymosin β-4 which detected in human tissues under negative ion mode.

Molecular Analysis of Human Cancer and Normal tissues sections. Ambient ionization mass spectrometry has been extensively investigated for molecular diagnosis of human cancerous tissues. To test the capability of MasSpec Pen system described herein for differentiating the normal and tumorous samples, 62 human tissue samples of five different tissue types including breast, kidney, lymph node, thyroid and ovary, were analyzed. The mass spectra obtained in the negative ion mode using water as solvent system for each tissue type showed molecular ions commonly observed by DESI-MS, with high relative abundances of metabolites and lipids. Principal component analysis (PCA) was employed to statistically evaluate the performance of MasSpec Pen in interspecific and intraspecific analyses of human specimen. It should be noted that the first three components, which all encompassed more than 85% of the total variance, are used in the present work. As can be seen in FIGS. 9A-B, normal thyroid and kidney tissues were well discriminated from the tumorous ones. Surprisingly, during the analysis of human tissue sections under negative ion mode, a series of multiply charged species were detected and were identified as thymosin β-4 by high mass accuracy measurements and tandem mass spectrometry analysis (FIG. 7). The representative spectra of each specimen are shown in FIG. 5. Remarkably, the molecular profiles obtained from human normal thyroid and cancerous tissue shows distinct molecular patterns that are diagnostic of disease state. Similar results were obtained for all the other cancerous tissues analyzed.

Figure 8A:
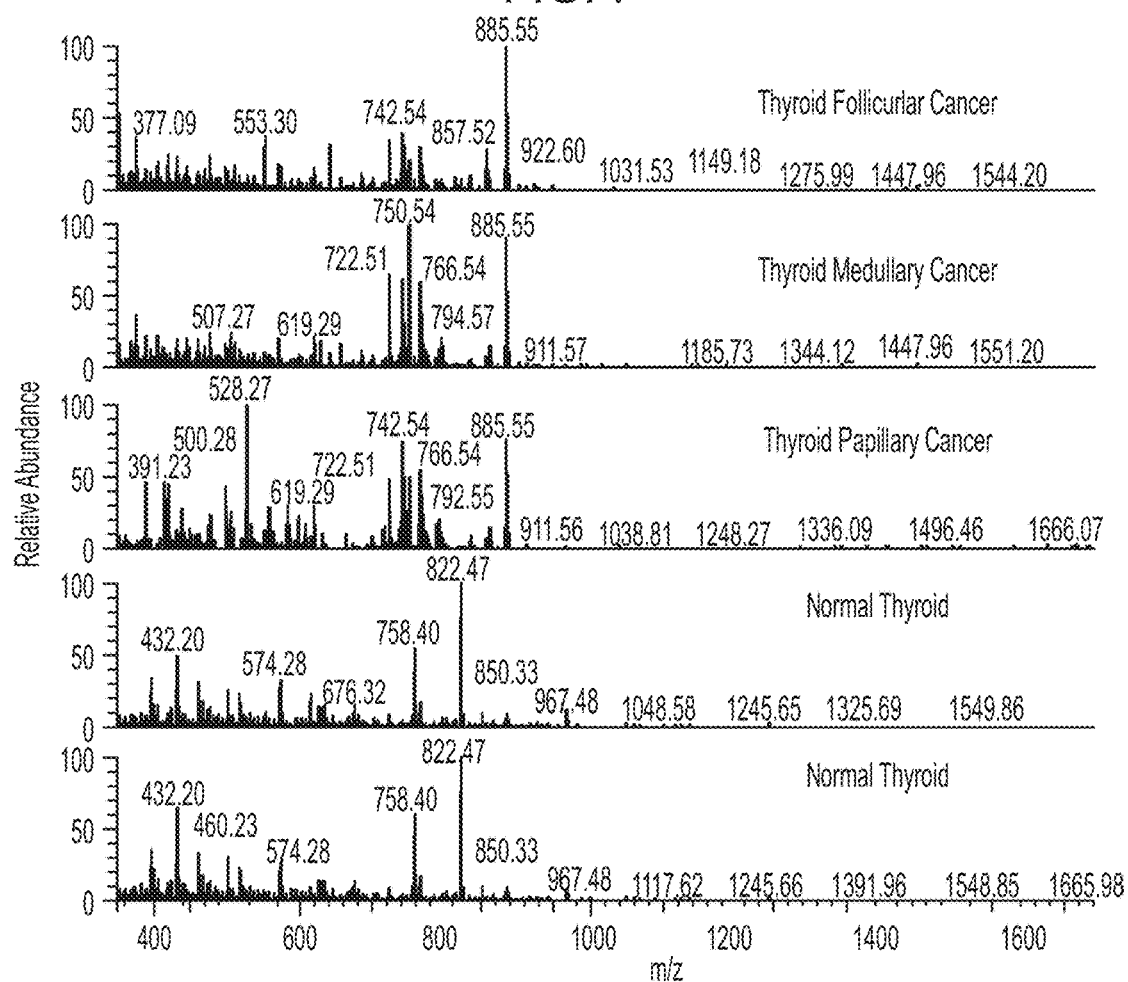
FIGS. 8A-8B: A) Comparison of spectra which were obtained from fresh thyroid normal and cancer specimens. B) MasSpec Pen analysis of papillary thyroid carcinoma and normal tissue sections. (top) A representative negative ion mode MasSpec Pen mass spectra obtained from a normal thyroid tissue section, and (bottom) a papillary thyroid carcinoma tissue section are shown. Identification of the most abundant molecular ions are provided. Insets shows an optical image of the H&E stained tissue section evaluated by histopathology.
Figure 8B:
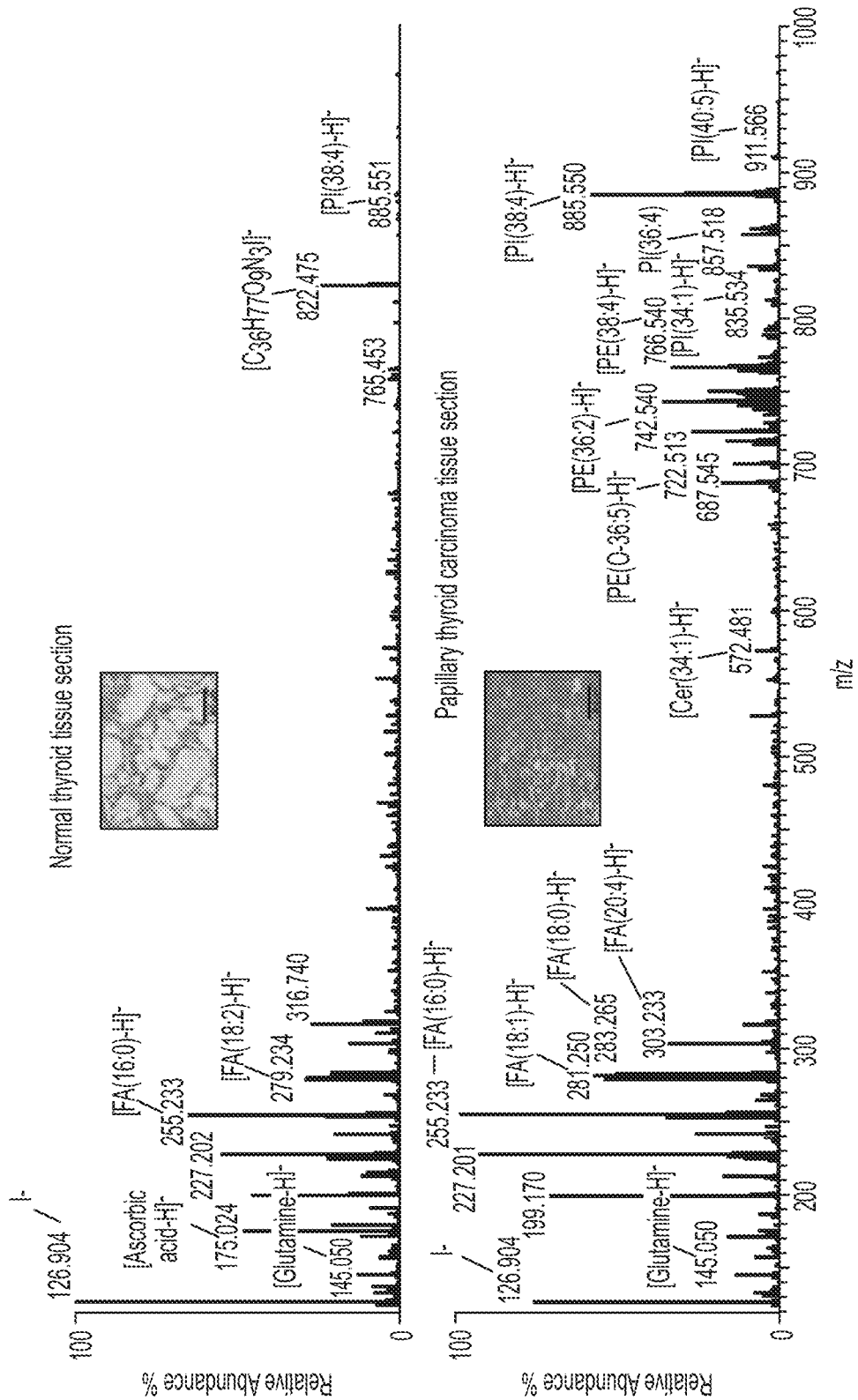
Figure 9:
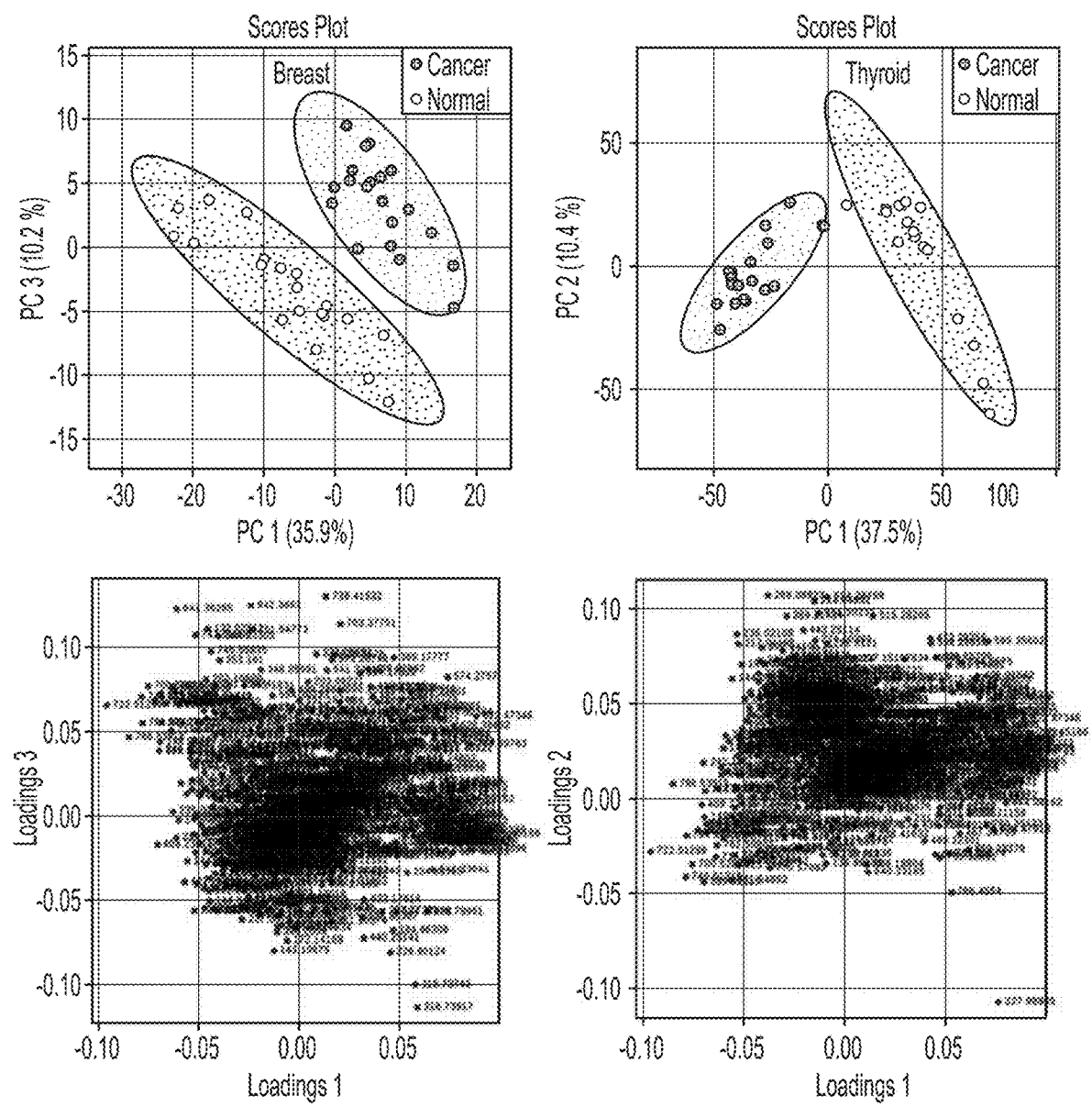
FIG. 9: PCA of the data obtained for the human tissue sections including normal and tumor thyroid and breast tissue sections. As observed in the scores plots, PC1 and PC3 explain 46.1% of the total variance of the breast tissue dataset, while PC1 and PC2 explain 47.9% of the total variance of the thyroid tissue dataset. Loading plots are also included for each tissue type analyzed.

The capability of the MasSpec Pen was tested to analyze 20 thin tissue sections of normal and tumor human breast (n=5 normal breast, n=5 breast ductal carcinoma) and thyroid (n=5 normal thyroid, n=4 papillary thyroid carcinoma, and n=1 follicular thyroid adenoma) tissues. The mass spectra obtained in the negative ion mode for each tissue type presented a rich variety of molecular ions commonly observed from human tissues by DESI-MSI, with high relative abundances of metabolites, fatty acids, and complex lipids. For example, the mass spectra obtained for papillary thyroid carcinoma tissue sections presented lipid species previously identified as diagnostic markers by DESI-MSI (Zhang et al., *Cancer Research*, 76, 2016), including a variety of doubly-charged CL, and other glycerophospholipids such as PI (38:4) (m/z 885.550), PI (36:4) (m/z 857.518), PE (38:4) (m/z 766.539), and PE (36:2) (m/z 742.539) (Table 2). A distinct mass spectral profile was obtained for normal thyroid tissue section, presenting high relative abundances of m/z 126.904, identified as iodine, m/z 145.050, identified as glutamine, m/z 175.024, identified as ascorbic acid, m/z 822.472, tentatively assigned to $C_{36}H_{78}O_9N_3I$, and m/z 885.551, identified as PI (38:4) (FIG. 8B). Interestingly, a series of multiply charged molecular ions at different charge states (z) including m/z 991.091 (z=−5), m/z 1239.113 (z=−4), and m/z 1652.484 (z=−3) was detected in the mass spectra obtained from all tissue sections analyzed. These ions were tentatively identified as different charge states of the protein thymosin β-4 based on high mass accuracy measurements (FIG. 7 and Table 1). Notably, principal component analysis (PCA) performed on the data obtained from the human tissue sections analyzed showed separation between tumor and normal tissues (FIG. 9).

Figure 4A:
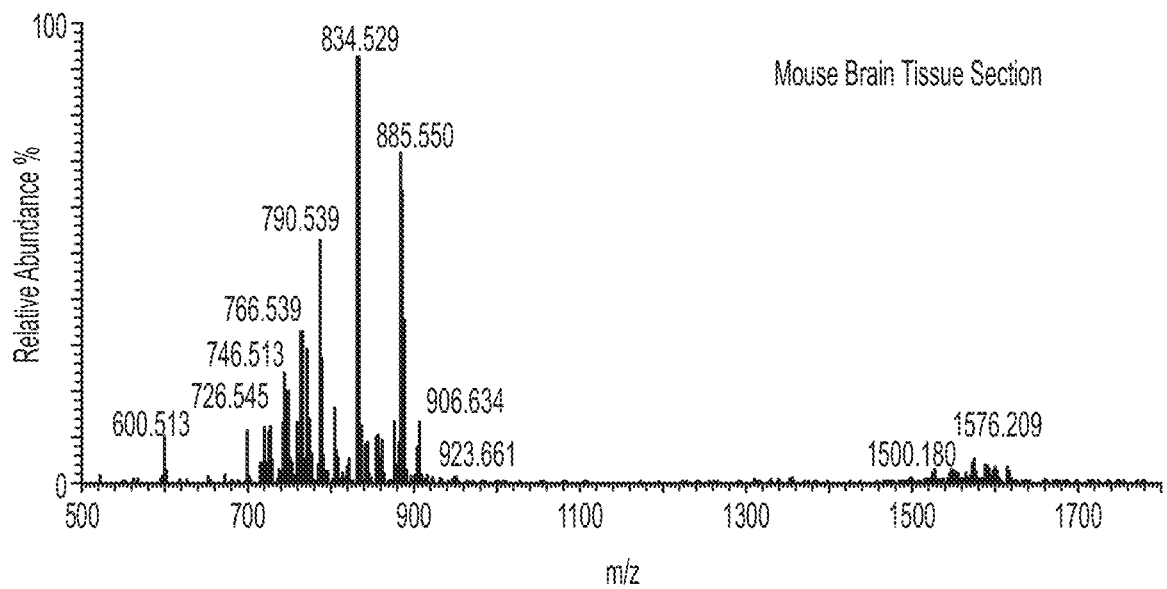
FIGS. 4A-4B: Comparison of mass spectra using MasSpec Pen collected from a) mouse brain sections and b) mouse brain fresh tissue.
Figure 4B:
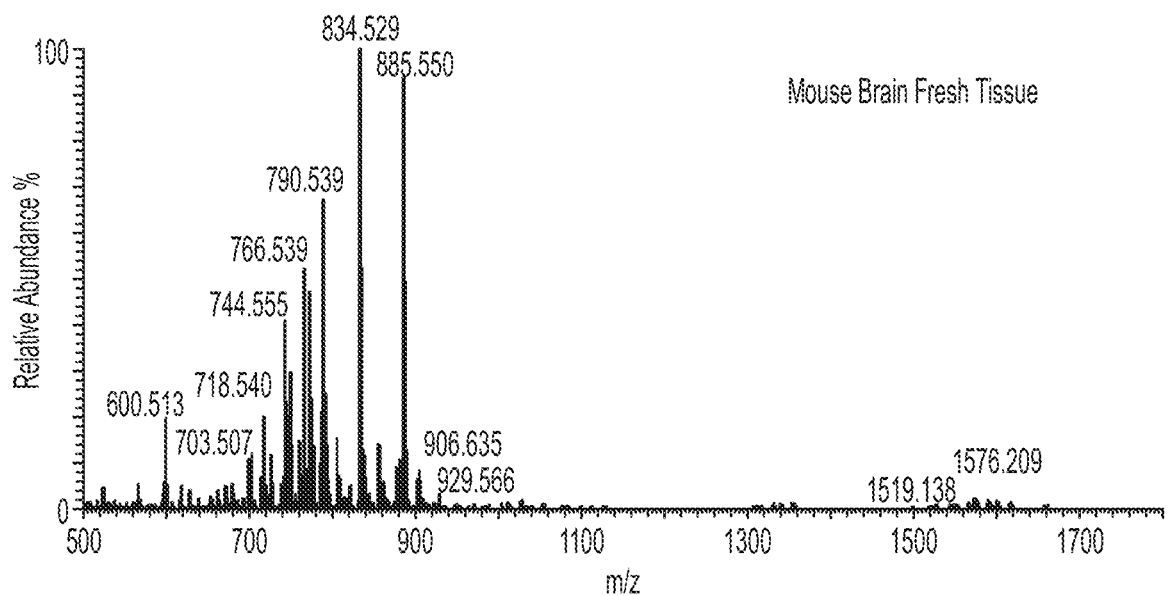
Figure 5A:
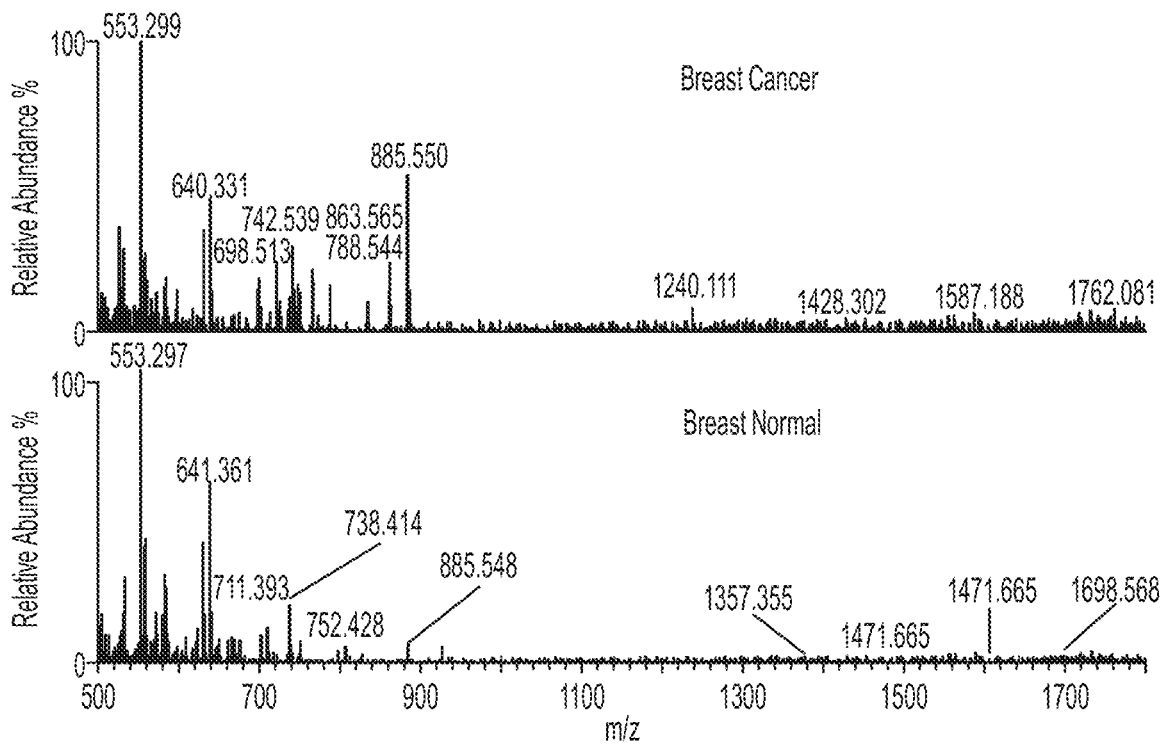
FIG. 5A-E: Comparison of mass spectra in cancer versus normal tissue for a variety of different cancer types: breast cancer (A); kidney cancer (B); a cancerous lymph node (C) ovarian cancer (D) and thyroid cancer (E).
Figure 5B:
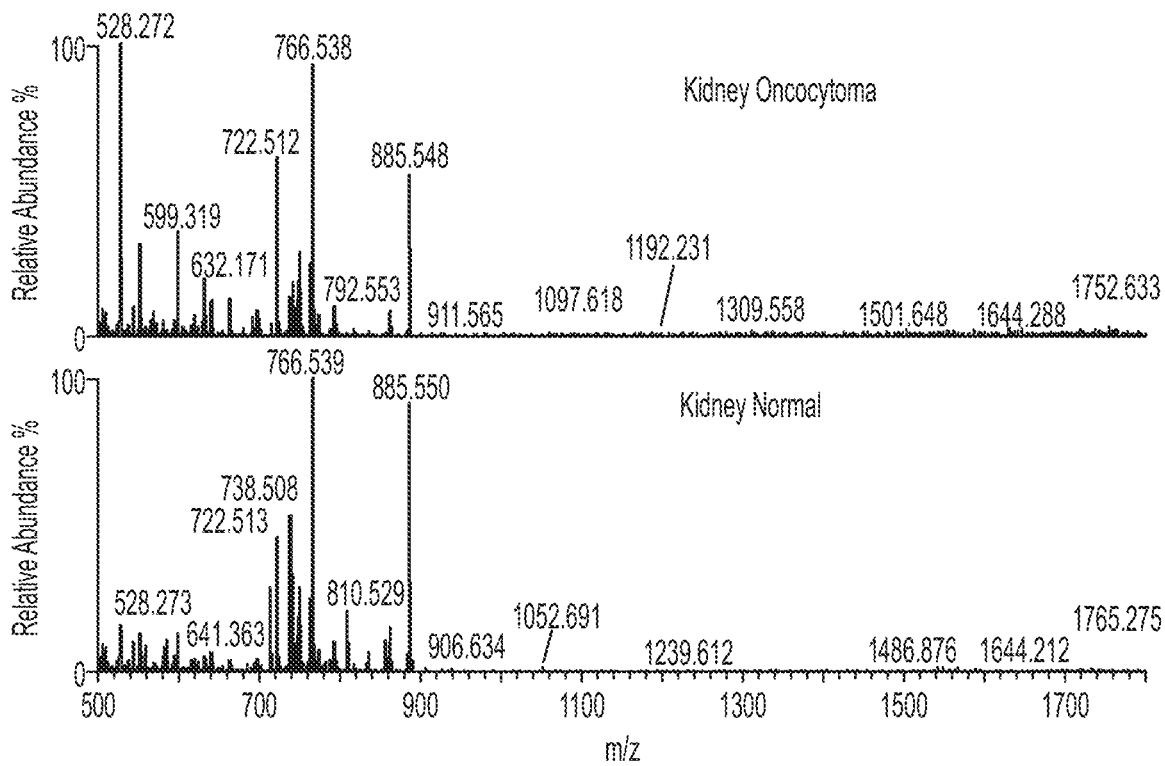
Figure 5C:
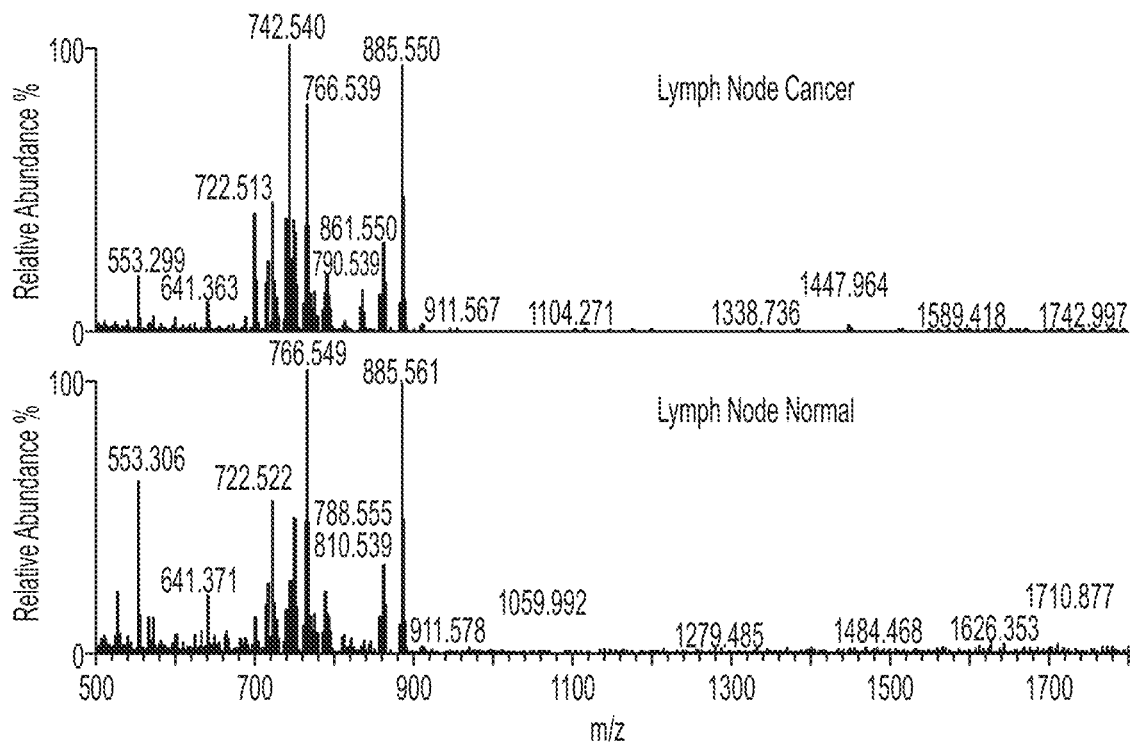
Figure 5D:
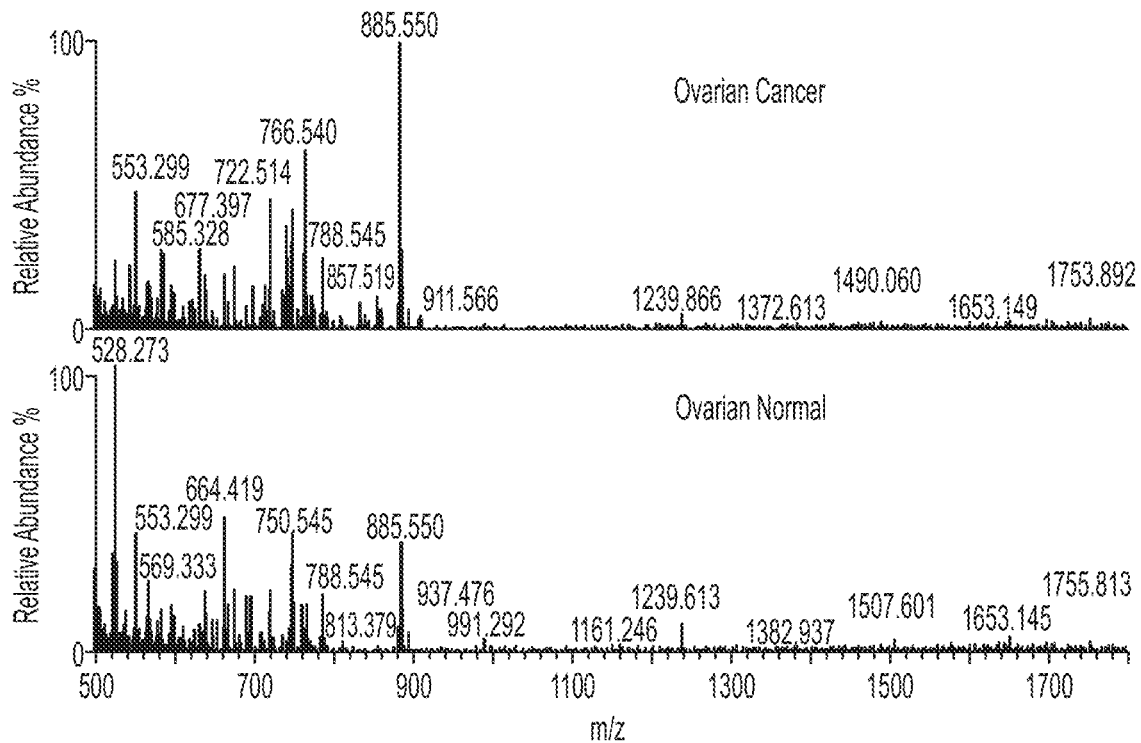
Figure 5E:
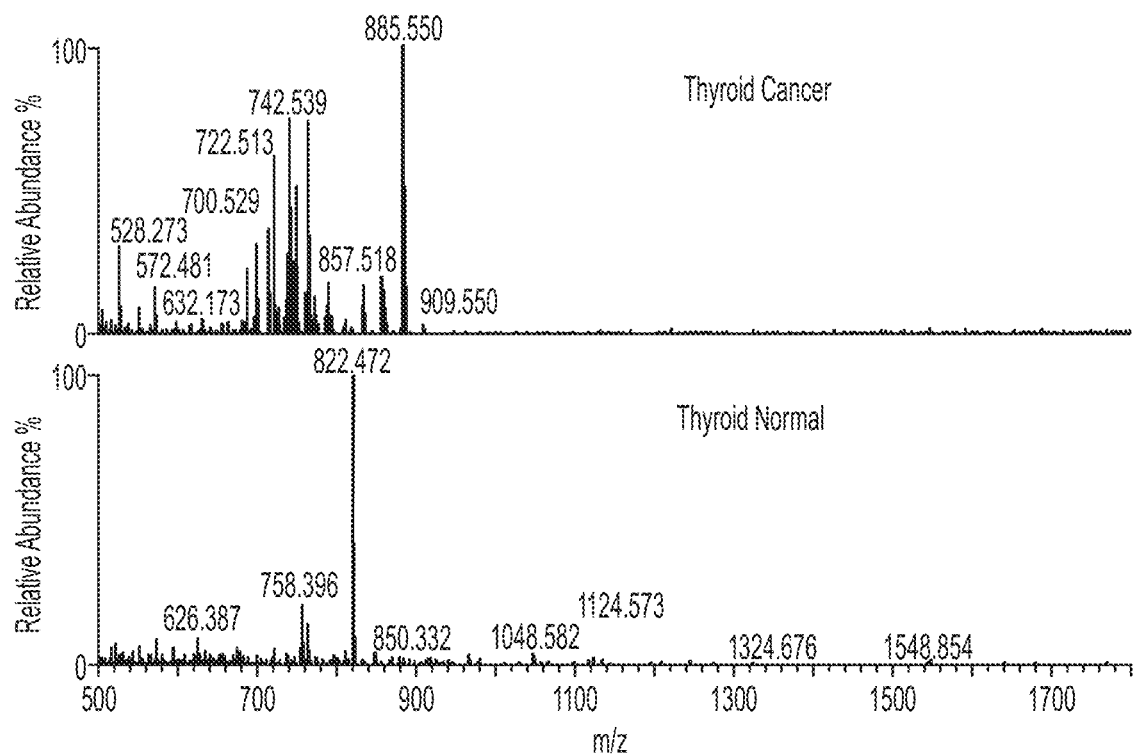

Molecular Analysis of Fresh Tissue Samples. The MasSpec Pen device was designed to operate on fresh tissue samples independently of morphology. To test the device for fresh tissue analysis, fresh mouse brain tissue was used in the beginning. No significant differences were observed in the spectra obtained from mouse brain tissue sections or fresh brain tissues. FIGS. 4A-4B show nearly identical mass spectrometric pattern from mouse brain fresh tissue and tissue sections, which illustrates that the extraction process from MasSpec Pen works similarly for different sample preparation steps. Then, two types of fresh human specimens were further analyzed, thyroid gland and lymph node. The spectra from normal and cancerous thyroid fresh tissue samples were shown in FIG. 8.

Figure 10A:
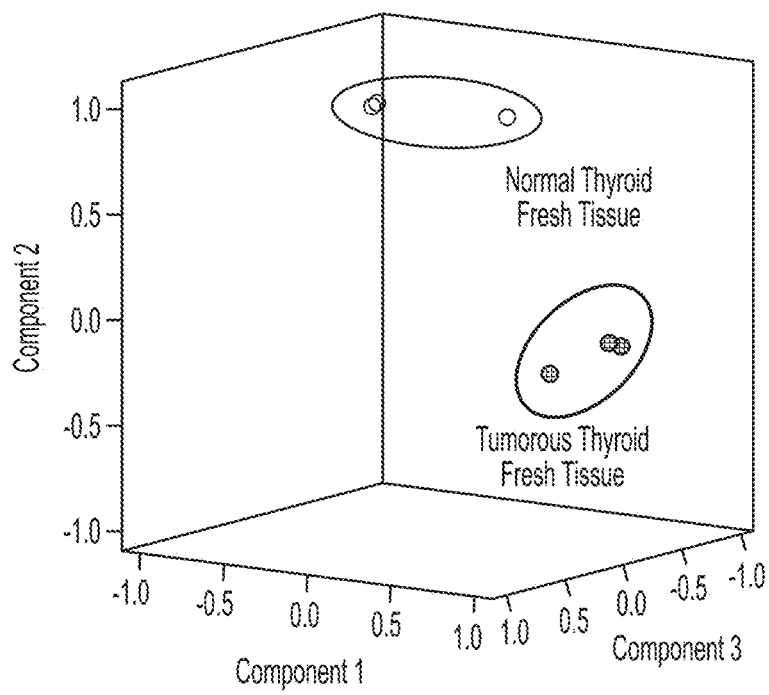
FIGS. 10A-10B: Principal component analysis results for human fresh tissues. A) Discrimination of normal and tumorous thyroid. B) Discrimination of normal and tumorous lymph nodes.
Figure 10B:
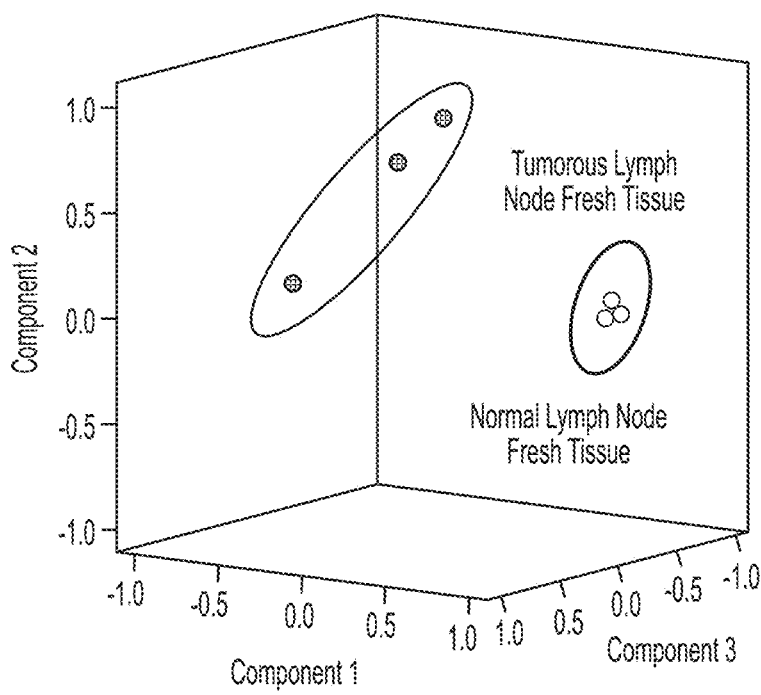

It should be noted that all the frozen specimens that were obtained from tissue banks, had been well preserved under −80° C. in freezer and were thawed at room temperature before use. The data collected from fresh human specimens were also processed by PCA. PCA of the spectra recorded shows a clear distinction between the normal and tumorous samples (FIGS. 10A-10B). Therefore, it is established that MasSpec Pen could be employed to differentiate fresh normal and diseased samples. It should be noted that no damage to the tissue was observed due to the sampling process.

TABLE 1

Data obtained for the identification of selected negative ion mode molecular ions from mouse brain tissue.

| Proposed Identification | | Proposed formula | Measured m/z | Theoretical m/z | Mass error (ppm) | Main Fragment ions upon MS/MS[a] |
|---|---|---|---|---|---|---|
| Thymosin β-4 | | $C_{212}H_{350}N_{56}O_{78}S_1$ | 991.091 (−5) | 991.090 (−5) | <1 (−5) | NA |
| | | | 1239.113 (−4) | 1239.114 (−4) | <1 (−4) | |
| | | | 1652.484 (−3) | 1652.488 (−3) | 2.4 (−3) | |
| ST | t42:1 | $C_{48}H_{92}NO_{12}S$ | 906.634 | 906.635 | −1.1 | NA |
| PI | 38:4 | $C_{47}H_{82}O_{13}P$ | 885.550 | 885.550 | <1 | 152.995, 241.011, 283.264, 303.233, 419.257, 581.309 |
| PS | 40:6 | $C_{46}H_{77}NO_{10}P$ | 834.529 | 834.529 | <1 | 152.994, 283.264, 327.233, 419.256, 437.267, 747.497 |
| PE | 40:6 | $C_{45}H_{77}NO_8P$ | 790.539 | 790.539 | <1 | 283.243, 283.264, 327.232, 480.309 |
| | 38:4 | $C_{43}H_{77}NO_8P$ | 766.539 | 766.539 | 0 | 259.243, 283.263, 303.232, 480.309 |
| | P-38:6 | $C_{43}H_{73}NO_7P$ | 746.513 | 746.513 | <1 | 283.243, 327.232, 436.282 |
| | O-36:3 | $C_{41}H_{77}NO_7P$ | 726.545 | 726.544 | 1.4 | 140.010, 152.994, 281.248, 444.288, 462.299 |
| | P-36:4 | $C_{41}H_{73}NO_7P$ | 722.513 | 722.513 | <1 | 152.994, 259.243, 303.233, 418.273, 436.283 |
| Cer | 36:1 | $C_{36}H_{71}NO_3Cl$ | 600.513 | 600.513 | <1 | NA |
| FA | 22:6 | $C_{22}H_{31}O_2$ | 327.233 | 327.233 | <1 | 229.195, 283.243, 309.174 |
| | 20:4 | $C_{20}H_{31}O_2$ | 303.233 | 303.233 | <1 | 205.195, 259.243, 284.991 |
| | 18:0 | $C_{18}H_{35}O_2$ | 283.264 | 283.264 | <1 | 265.130 |
| | 16:0 | $C_{16}H_{31}O_2$ | 255.233 | 255.233 | <1 | 237.043 |
| N-Acetylaspartic acid | | $C_6H_8NO_5$ | 174.040 | 174.041 | −5.7 | 58.028, 88.039, 130.049 |
| hexose | | $C_6H_{12}O_6Cl$ | 215.033 | 215.034 | −4.7 | NA |
| glutamate | | $C_5H_8NO_4$ | 146.045 | 146.046 | −6.8 | 102.054, 128.034 |
| Glutamine | | $C_5H_9N_2O_3$ | 145.061 | 145.062 | −6.9 | 127.050, 128.034 |

[a]NA (not available) means that only high mass accuracy was used for tentative ion identification.

TABLE 2

Data obtained for the identification of selected negative ion mode molecular ions from human thyroid tissue.

| | Proposed Identification | | Proposed formula | Measured m/z | Theoretical m/z | Mass error (ppm) | Main Fragment ions upon MS/MS[a] |
|---|---|---|---|---|---|---|---|
| PI | 40:5 | | $C_{49}H_{84}O_{13}P$ | 911.566 | 911.566 | <1 | NA |
| | 38:4 | | $C_{47}H_{82}O_{13}P$ | 885.550 | 885.550 | <1 | 152.994, 223.006, 241.011, 283.264, 303.233, 419.256, 581.310 |
| | 36:4 | | $C_{45}H_{78}O_{13}P$ | 857.518 | 857.518 | <1 | 152.994, 241.011, 279.233, 415.226, 577.278 |
| | 34:1 | | $C_{45}H_{80}O_{13}P$ | 835.534 | 835.534 | <1 | 152.994, 241.011, 255.232, 391.226, 553.277 |
| PE | 38:4 | | $C_{43}H_{77}NO_8P$ | 766.539 | 766.539 | <1 | 140.010, 152.995, 259.243, 283.264, 303.233, 480.309 |
| | 36:2 | | $C_{41}H_{77}NO_8P$ | 742.539 | 742.540 | −1.3 | 140.010, 152.994, 281.248 |
| | P-36:4 | | $C_{41}H_{73}NO_7P$ | 722.513 | 722.513 | <1 | 140.010, 196.037, 259.243, 303.233, 418.270, 436.283 |
| CL | 74:7 | | $C_{83}H_{146}O_{17}P_2$ | 738.502 | 738.502 | <1 | NA |
| | 72:8 | | $C_{81}H_{140}O_{17}P_2$ | 723.479 | 723.479 | <1 | NA |
| Cer | 34:1 | | $C_{34}H_{67}NO_3Cl$ | 572.481 | 572.482 | −1.7 | NA |
| FA | 20:4 | | $C_{20}H_{31}O_2$ | 303.233 | 303.233 | <1 | 205.195, 259.243, 284.992 |
| | 18:0 | | $C_{18}H_{35}O_2$ | 283.265 | 283.264 | 3.5 | 265.130 |
| | 18:1 | | $C_{18}H_{33}O_2$ | 281.250 | 281.249 | 3.6 | NA |
| | 18:2 | | $C_{18}H_{31}O_2$ | 279.234 | 279.233 | 3.6 | 261.222 |
| | 16:0 | | $C_{18}H_{31}O_2$ | 255.233 | 255.233 | <1 | NA |
| Ascorbic acid | | | $C_6H_7O_6$ | 175.024 | 175.025 | −5.7 | 87.007, 115.002 |
| Glutamine | | | $C_5H_9N_2O_3$ | 145.050 | 145.062 | −8.3 | NA |
| I- | | | | 126.904 | 126.905 | −7.9 | NA |

[a] NA (not available) means that only high mass accuracy was used for tentative ion identification.

TABLE 3

Data obtained for the identification of selected negative ion mode molecular ions from human ovarian tissue.

| Proposed Identification | | Proposed formula | Measured m/z | Theoretical m/z | Mass error (ppm) | Main Fragment ions upon MS/MS[a] |
|---|---|---|---|---|---|---|
| PI | 40:4 | $C_{49}H_{86}O_{13}P$ | 913.581 | 913.581 | <1 | 223.000, 241.011, 283.264, 331.264, 419.257, 581.309 |
| | 38:4 | $C_{47}H_{82}O_{13}P$ | 885.549 | 885.550 | −1.1 | 152.994, 223.000, 241.011, 283.264, |

TABLE 3-continued

Data obtained for the identification of selected negative ion mode molecular ions from human ovarian tissue.

| Proposed Identification | | Proposed formula | Measured m/z | Theoretical m/z | Mass error (ppm) | Main Fragment ions upon MS/MS[a] |
|---|---|---|---|---|---|---|
| | 36:1 | $C_{45}H_{84}O_{13}P$ | 863.565 | 863.566 | −1.2 | 303.233, 419.256, 439.225, 581.309 |
| | 34:1 | $C_{43}H_{80}O_{13}P$ | 835.534 | 835.534 | <1 | 152.995, 241.011, 281.248, 283.264, 419.256 |
| PS | 38:3 | $C_{44}H_{79}NO_{10}P$ | 812.544 | 812.545 | −1.2 | 152.994, 223.000, 241.011, 255.233, 281.248, 391.225, 553.278 |
| | 36:1 | $C_{42}H_{79}NO_{10}P$ | 788.545 | 788.545 | <1 | 152.994, 283.264, 305.248, 419.256, 437.266, 725.514 |
| PE | 38:4 | $C_{43}H_{80}O_{13}P$ | 766.539 | 766.539 | <1 | 281.248, 283.264, 417.242, 419.256, 437.268, 701.512 |
| | O-38:5 | $C_{43}H_{77}NO_{7}P$ | 750.544 | 750.544 | <1 | 259.243, 283.264, 303.233, 480.309 |
| | P-35:4 | $C_{41}H_{73}NO_{7}P$ | 722.512 | 722.513 | −1.4 | 259.243, 303.233, 446.303, 464.313 |
| FA | 16:0 | $C_{16}H_{31}O_{2}$ | 255.232 | 255.233 | −3.9 | 259.243, 303.233, 418.273, 436.283 |
| Ascorbic acid | | $C_{6}H_{7}O_{6}$ | 175.024 | 175.024 | <1 | NA 87.007, 115.002 |

[a]NA (not available) means that only high mass accuracy was used for tentative ion identification.

TABLE 4

Data obtained for the identification of selected negative ion mode molecular ions from human lung tissue.

| Proposed Identification | | Proposed formula | Measured m/z | Theoretical m/z | Mass error (ppm) | Main Fragment ions upon MS/MS[a] |
|---|---|---|---|---|---|---|
| PI | 40:4 | $C_{49}H_{86}O_{13}P$ | 913.580 | 913.581 | −1.1 | 152.994, 223.000, 241.010, 283.264, 331.264, 419.256, 581.311 |
| | 38:4 | $C_{47}H_{82}O_{13}P$ | 885.550 | 885.550 | <1 | 152.994, 223.000, 241.011, 283.264, 303.233, 419.256, 581.311 |

TABLE 4-continued

Data obtained for the identification of selected negative ion mode molecular ions from human lung tissue.

| Proposed Identification | | Proposed formula | Measured m/z | Theoretical m/z | Mass error (ppm) | Main Fragment ions upon MS/MS[a] |
|---|---|---|---|---|---|---|
| | 36:1 | $C_{45}H_{84}O_{13}P$ | 863.565 | 863.566 | −1.2 | 152.994, 241.011, 281.248, 283.264, 419.256, 581.311 |
| | 36:2 | $C_{45}H_{82}O_{13}P$ | 861.548 | 861.549 | −1.2 | 152.994, 223.000, 241.011, 281.256, 417.241 |
| PG | 36:2 | $C_{42}H_{78}O_{10}P$ | 773.542 | 773.534 | 10 | 152.994, 281.256, 417.241, 491.278, 509.288 |
| | 34:1 | $C_{40}H_{76}O_{10}P$ | 747.514 | 747.517 | −4.0 | 152.994, 255.233, 281.256, 391.226, 417.241, 491.277 |
| PE | 38:4 | $C_{43}H_{77}NO_8P$ | 766.535 | 766.539 | −5.2 | 140.010, 283.256, 303.233, 480.309 |
| | 36:1 | $C_{41}H_{79}NO_8P$ | 744.552 | 744.555 | −4.0 | 140.011, 281.256, 283.264, 480.307 |
| | P-38:4 | $C_{43}H_{77}NO_7P$ | 750.534 | 750.544 | −13 | 259.243, 303.233, 464.314 |
| | P-36:4 | $C_{41}H_{73}NO_7P$ | 722.511 | 722.513 | −2.8 | 259.243, 303.233, 418.273, 436.283 |
| | O-34:2 | $C_{39}H_{75}NO_7P$ | 700.527 | 700.529 | −2.9 | NA |
| Cer | 34:1 | $C_{34}H_{67}NO_3Cl$ | 572.479 | 572.482 | −5.2 | NA |
| FA | 18:1 | $C_{18}H_{33}O_2$ | 281.249 | 281.249 | <1 | NA |
| Ascorbic Acid | | $C_6H_7O_6$ | 175.023 | 175.024 | −5.7 | 115.002 |

[a]NA (not available) means that only high mass accuracy was used for tentative ion identification.

TABLE 5

Data obtained for the identification of selected negative ion mode molecular ions from human breast tissue.

| Proposed Identification | | Proposed formula | Measured m/z | Theoretical m/z | Mass error (ppm) | Main Fragment ions upon MS/MS[a] |
|---|---|---|---|---|---|---|
| PI | 38:4 | $C_{47}H_{82}O_{13}P$ | 885.550 | 885.550 | <1 | 152.994, 223.000, 241.011, 283.264, 303.233, 419.257, 581.310, 599.319 |
| | 36:1 | $C_{45}H_{84}O_{13}P$ | 863.565 | 863.566 | −1.2 | 152.994, 223.000, 241.011, 281.248, 283.264, 419.256, 581.309 |
| PG | 36:2 | $C_{42}H_{78}O_{10}P$ | 773.542 | 773.534 | 10 | 152.994, 281.248, 417.240, 491.276 |
| FA | 20:4 | $C_{20}H_{31}O_2$ | 303.233 | 303.233 | <1 | 205.195, 259.243, 284.991 |
| | 18:1 | $C_{18}H_{33}O_2$ | 281.249 | 281.249 | <1 | NA |

[a]NA (not available) means that only high mass accuracy was used for tentative ion identification.

TABLE 6

Patient demographics of the 253 human tissue samples used in this study.

| Patient | Diagnosis | Median age, Years | Age range, Years | Number of patients by gender (male, female) | Number of patients by race (White, Black, Asian, Unknown) |
|---|---|---|---|---|---|
| Breast | Normal | 47 | 24-76 | (0, 29) | (21, 7, 1, 0) |
|  | Cancer | 58 | 41-75 | (2, 14) | (10, 2, 4, 0) |
| Lung | Normal | 57 | 12-82 | (33, 14) | (35, 12, 0, 0) |
|  | Cancer | 66 | 22-84 | (25, 23) | (35, 7, 0, 6) |
| Ovary | Normal | 50 | 31-80 | (0, 29) | (22, 7, 0, 0) |
|  | Cancer | 62 | 30-83 | (0, 28) | (25, 2, 0, 1) |
| Thyroid | Normal | 40 | 18-80 | (10, 17) | (18, 7, 0, 2) |
|  | Tumor | 49 | 16-81 | (12, 17) | (21, 4, 0, 4) |

Materials and Methods.

Mass Spectrometer. Q Exactive Hybrid Quadrupole-Orbitrap mass spectrometer (Thermo Scientific, San Jose, Calif.) was used. Full-scan was carried out at the range of m/z 120-1800, and the other mass spectrometric parameters were listed as follows: resolving power 140 000, micro scan 2, maximum injection time 300 ms, capillary temperature 350° C. and S-lens RF level 100.

Biological Tissues. Wild-type mouse brains were purchased from Bioreclamation IVT. 62 frozen human tissue specimens including breast, thyroid, lymph node, ovarian, and kidney were obtained from Cooperative Human Tissue Network and Baylor College Tissue Bank. Samples were stored in a −80° C. freezer. Tissue slides were sectioned at 16 μm using a CryoStar™ NX50 cryostat. Frozen tissue specimen were thawed under room temperature before use.

Statistical Analysis. IBM SPSS Statistics 22.0 (IBM Corporation, Armonk, N.Y., USA) was used to perform principal component analysis (PCA) to reveal patterns in the data. The analysis was performed directly using the raw data. The 10 peaks of the top relative intensities in the m/z range of 700-900 were used for PCA. Typically, the first three components, which all encompassed more than 85% of the total variance, are used in the present results.

EXAMPLE 3

System Automation for Handheld and Laparoscopic Use

Because all the materials (PDMS and PTFE) and solvent (only water) used in the MasSpec Pen design are biologically compatible, the system has a high potential to be used in surgery in handheld way for real-time analysis. More than that, due to the small dimension of the device, it can even be integrated to a robotic surgical system, such as the Da Vinci surgical system through an accessory port or one of its robotic arms. Several regions of the human body cavity can be quickly sampled during surgery, and analyzed by using a database of molecular signatures and machine learning algorithms. Therefore, the diagnosing results may be provided in real time for each sampled region. This system can be broadly used in a wide variety of oncological and other surgical interventions (such as endometriosis) for which real-time characterization and diagnosis of tissues are needed.

EXAMPLE 4

Predictive Analysis of Tissue Samples

The MasSpec Pen design was used to analyze tissue samples from patients with breast cancer, lung cancer, ovarian cancer, or thyroid cancer along with normal tissue samples. Before these samples were analyzed, the samples were processed by rounding the mass to charge ratio (m/z) to the nearest 0.01 and normalizing the total ion chromatogram (TIC). All background m/z peaks and those peaks which appeared in less than 10% of the patient samples were also removed. The full mass range was used in the analysis. The trained classifier was a lasso logistic regression model. For tissue samples in which the presence of cancer was being analyzed, the overall performance results for all classifiers is shown in Table 7. The overall results has an accuracy of 96.3%, sensitivity of 96.4%, and specificity of 96.2%.

TABLE 7

Tissue Sample Prediction Relative to True Determination of All Normal vs All Cancer*

|  |  | Predicted | |
|---|---|---|---|
|  |  | Normal | Cancer |
| True | Normal | 127 | 5 |
|  | Cancer | 4 | 106 |

*not including Benign Thyroid

For the tissue samples in which the presence of lung cancer was being analyzed, Table 8 shows the mass to charge values (m/z) used in the differentiation of the tissue samples along with the associated coefficient for that particular value.

TABLE 8

Lung Cancer Mass to Charge Values (m/z) and Coefficients for Normal Lung vs Lung Cancer

| m/z | Coefficient |
|---|---|
| 175.02 | 32.51042 |
| 187.01 | 492.94937 |
| 201.04 | 324.19856 |
| 215.03 | −134.54101 |
| 313.16 | −711.31964 |
| 330.98 | 31.73486 |
| 332.90 | −49.54229 |
| 357.10 | −903.32504 |
| 409.23 | 218.36836 |
| 615.17 | −418.02900 |
| 722.51 | 42.39442 |
| 744.55 | 780.14488 |
| 747.52 | −248.52283 |
| 748.52 | −494.98929 |
| 771.52 | 6.80739 |
| 773.53 | −292.30917 |
| 863.57 | −722.21921 |
| 885.55 | 703.46083 |
| 886.55 | 8.82125 |

Table 9 shows the analysis rate and the classification of each sample with the true (histological) determination in rows and the predicted value in the columns. Of the cancer tissue samples, the samples were identified with an accuracy of 96.8%, a sensitivity of 97.9%, specificity of 95.7% and AUC of 0.97.

TABLE 9

Tissue Sample Prediction Relative to True Determination for Lung Cancer

| | | Predicted | | Prop. |
|---|---|---|---|---|
| | | Normal | Cancer | correct |
| True | Normal | 45 | 2 | 0.957 |
| | Cancer | 1 | 47 | 0.979 |

Similar analysis was performed for normal lung vs adenocarcinoma samples as shown in Table 10 and Table 11. The samples were identified with 92.2% accuracy, 88.2% sensitivity, 93.6% specificity, and AUC of 0.98.

TABLE 10

Lung Cancer Mass to Charge Values (m/z) and Coefficients for Normal Lung vs Adenocarcinoma

| m/z | Coefficient |
|---|---|
| 175.02 | 78.79492 |
| 201.04 | 113.95819 |
| 747.52 | −134.59620 |
| 773.53 | −17.30482 |
| 885.55 | 205.16262 |

TABLE 11

Tissue Sample Prediction Relative to True Determination for Lung Squamous Cell Carcinoma

| | | Predicted | | Prop. |
|---|---|---|---|---|
| | | Normal | Cancer | Correct |
| True | Normal | 44 | 3 | 0.936 |
| | Cancer | 2 | 15 | 0.882 |

Similar analysis was performed for normal lung vs squamous samples as shown in Table 12 and Table 13. The samples were identified with 93.8% accuracy, 88.2% sensitivity, 95.7% specificity, and AUC of 0.93.

TABLE 12

Lung Cancer Mass to Charge Values (m/z) and Coefficients for Normal Lung vs Squamous Cell Lung Cancer

| m/z | Coefficient |
|---|---|
| 201.04 | 203.209288 |
| 306.08 | 2.171805 |
| 747.52 | −83.325218 |
| 773.53 | −101.591552 |
| 861.55 | −22.995934 |
| 885.55 | 248.475559 |

TABLE 13

Tissue Sample Prediction Relative to True Determination for Lung Cancer

| | | Predicted | | Prop. |
|---|---|---|---|---|
| | | Normal | Cancer | Correct |
| True | Normal | 45 | 2 | 0.957 |
| | Cancer | 2 | 15 | 0.882 |

Similar, to the analysis carried out for lung cancer described above, a similar analysis was carried out with ovarian, thyroid, and breast cancer and showing the respective m/z peaks and coefficients for each set of samples. Ovarian cancer samples were detected with 94.7% accuracy, 100% sensitivity, 89.7% specificity, and AUC of 0.98. The thyroid cancer samples were detected with 94.7% accuracy, 90.9% sensitivity, 96.3% specificity, and AUC of 0.93. Finally, breast cancer samples were detected with 95.6% accuracy, 87.5% sensitivity, 100% specificity, and AUC of 1.00.

TABLE 14

Ovarian Cancer Mass to Charge Values (m/z) and Coefficients

| m/z | Coefficient |
|---|---|
| 124.01 | −0.39418349 |
| 175.02 | −0.44099907 |
| 175.03 | −0.65091248 |
| 283.27 | −0.19534503 |
| 313.16 | 0.13896620 |
| 341.27 | −0.01845538 |

TABLE 15

Tissue Sample Prediction Relative to True Determination for Ovarian Cancer

| | | Predicted | | Prop. |
|---|---|---|---|---|
| | | Normal | Cancer | Correct |
| | Normal | 26 | 3 | 0.897 |
| | Cancer | 0 | 28 | 1.000 |

TABLE 16

Thyroid Cancer Mass to Charge Values (m/z) and Coefficients for Normal Thyroid vs Benign Tumor

| m/z | Coefficient |
|---|---|
| 175.02 | 0.050122579 |
| 191.02 | −0.009462112 |
| 191.05 | −0.354060964 |
| 283.27 | −0.471995496 |
| 341.27 | −0.151684619 |
| 615.17 | −0.208451792 |
| 822.47 | −1.009896669 |
| 822.48 | −1.045185471 |

TABLE 17

Tissue Sample Prediction Relative to True Determination for Normal Thyroid vs Benign Tumor

| | | Predicted | | Prop. |
|---|---|---|---|---|
| | | Normal | Cancer | Correct |
| True | Normal | 26 | 1 | 0.963 |
| | Cancer | 1 | 10 | 0.909 |

TABLE 18

Thyroid Cancer Mass to Charge Values (m/z) and Coefficients for Normal Thyroid vs Malignant Tumor

| m/z | Coefficient |
| --- | --- |
| 175.02 | −0.13520642 |
| 283.27 | −0.41455282 |
| 341.27 | −0.16730814 |
| 353.16 | −0.06014487 |
| 432.20 | −0.31647335 |
| 433.21 | −0.07291166 |
| 615.17 | −0.61749889 |
| 822.47 | −0.53746679 |
| 822.48 | −1.04230818 |

TABLE 19

Tissue Sample Prediction Relative to True Determination for Normal Thyroid vs Benign Tumor

| | | Predicted | | Prop. |
| --- | --- | --- | --- | --- |
| | | Normal | Cancer | Correct |
| True | Normal | 26 | 1 | 0.963 |
| | Cancer | 1 | 10 | 0.909 |

TABLE 20

Thyroid Cancer Mass to Charge Values (m/z) and Coefficients for Normal Breast vs Breast Cancer

| m/z | Coefficient |
| --- | --- |
| 187.04 | 476.70006 |
| 268.80 | −190.32304 |
| 279.92 | 79.49933 |
| 283.27 | −31.45926 |
| 341.27 | −11.77054 |
| 345.16 | −154.78978 |
| 381.21 | −68.13689 |
| 687.51 | −39.13906 |
| 742.54 | 1771.27018 |
| 766.54 | 1663.80192 |

TABLE 21

Tissue Sample Prediction Relative to True Determination for Normal Breast vs Breast Cancer

| | | Predicted | | Prop. |
| --- | --- | --- | --- | --- |
| | | Normal | Cancer | Correct |
| True | Normal | 29 | 0 | 1.000 |
| | Cancer | 2 | 14 | 0.875 |

EXAMPLE 5

Spatial Resolution of the MasSpec Pen System

The spatial resolution of the MasSpec Pen system was tested and determined that higher spatial resolution could be determined using a specific spot. Testing was carried out using white vs. grey matter in a mouse brain. Shown in FIGS. 11A-11E show the portion of the brain tested with the particular size of the spot. In particular, Sample Spot 1 shows the spot was primarily comprised of gray matter

EXAMPLE 6

Non-destructive Molecular Analysis of Tissue Samples

The MasSpec Pen was designed to operate directly on tissue specimens independently of tissue stiffness and morphology. The performance of the MasSpec Pen was tested to analyze soft tissue samples (0.1-5 g) from different organs including mouse brain and human breast, thyroid, lung and ovary tissues. Tissue analyses were performed in ambient conditions through a simple one-step experiment, following the same automated operational steps described previously. The MasSpec Pen tip was gently contacted to the surface of the tissue sample for a period of 3 s while extraction took place. The mass spectra obtained for a region of grey matter from the mouse brain was reproducible (RSD=4.6%, n=10) and highly similar to the mouse brain tissue section mass spectra (cosine similarity of 0.93) (FIG. 4), thus indicating that the extraction process at the tissue surface efficiently occurs independently on the tissue shape and rigidity. Similarly, MasSpec Pen analyses of human tissue samples provided rich molecular information, especially of tissues composed of epithelial and cancerous cells. Non-cancerous tissue specimens that were mostly composed of soft connective tissue such as stroma provided less abundant mass spectral profiles. In particular, many of the normal breast cancer tissue samples analyzed presented fat content, which is immiscible with water and thus yielded less abundant total ion counts in the mass spectra when compared to breast cancer tissues or normal breast cancer glands.

Figure 15A:
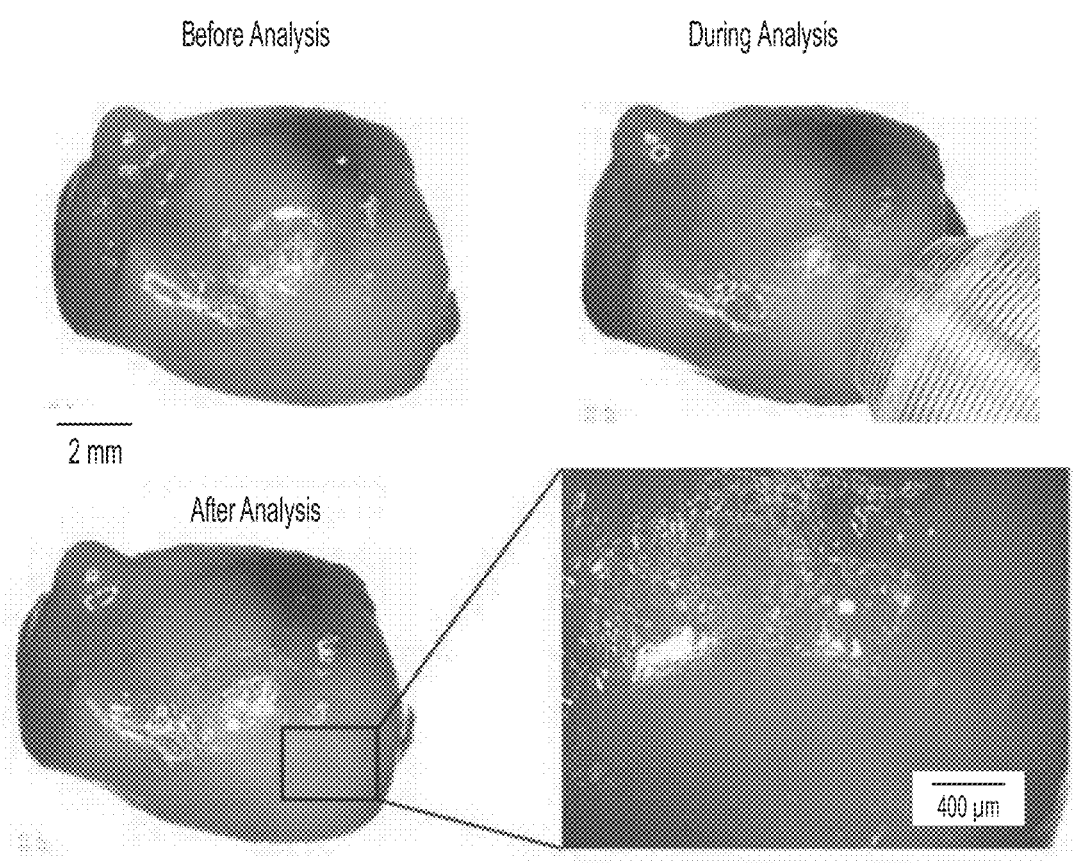
FIGS. 15A-15B: The MasSpec Pen allows gentle and non-destructive molecular analysis of tissue samples. A) Optical images show a lung adenocancinoma tissue sample before, during and after MasSpec Pen analysis. A magnification of the tissue specimen shows no macroscopic damage to the tissue region analyzed by the MasSpec Pen. B) The negative ion mode mass spectrum obtained for the tissue region analyzed is shown including identification of the most abundant molecular ions.
Figure 15B:
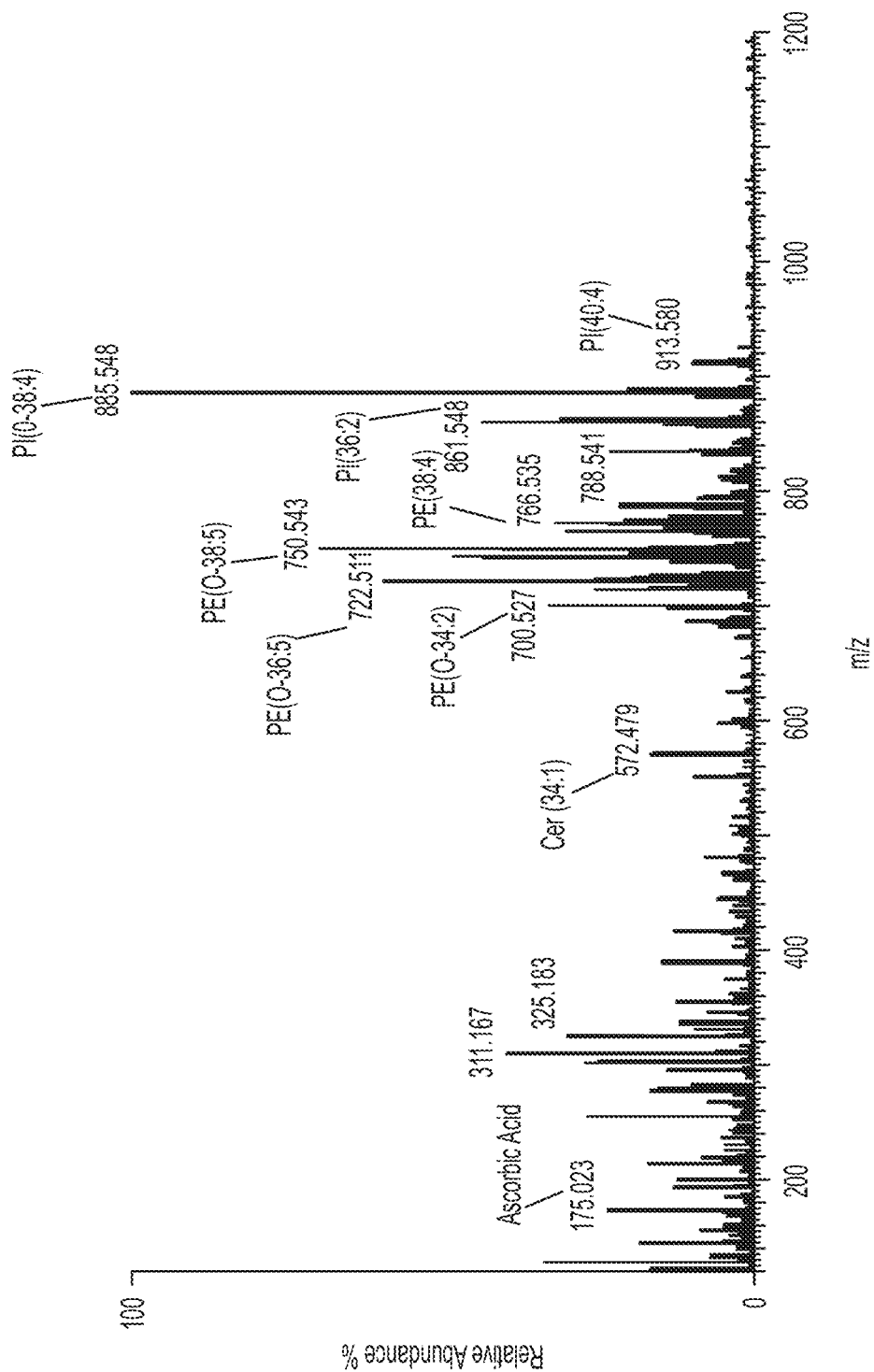

Visual and microscopic inspection of all the tissue samples after MasSpec Pen analysis revealed no detectable damage to the tissue sample morphology in the region probed. FIG. 15 shows optical images obtained from a lung tissue sample prior, during and after the MasSpec Pen analysis. No observable damage to the tissue was seen at the region analyzed, while rich mass spectra profiles were obtained (FIG. 15). Note that the automated and time-controlled operational steps of the MasSpec Pen prevents tissue damage as the tissue is only exposed to the small water droplet and not to the vacuum used to transport the droplet from the reservoir to the mass spectrometer. Thus, these results provide evidence that the MasSpec Pen is a non-destructive approach to obtain rich molecular information from tissue samples.

EXAMPLE 7

Molecular Diagnosis and Statistical Prediction of Cancer in Human Tissues

Figure 11:
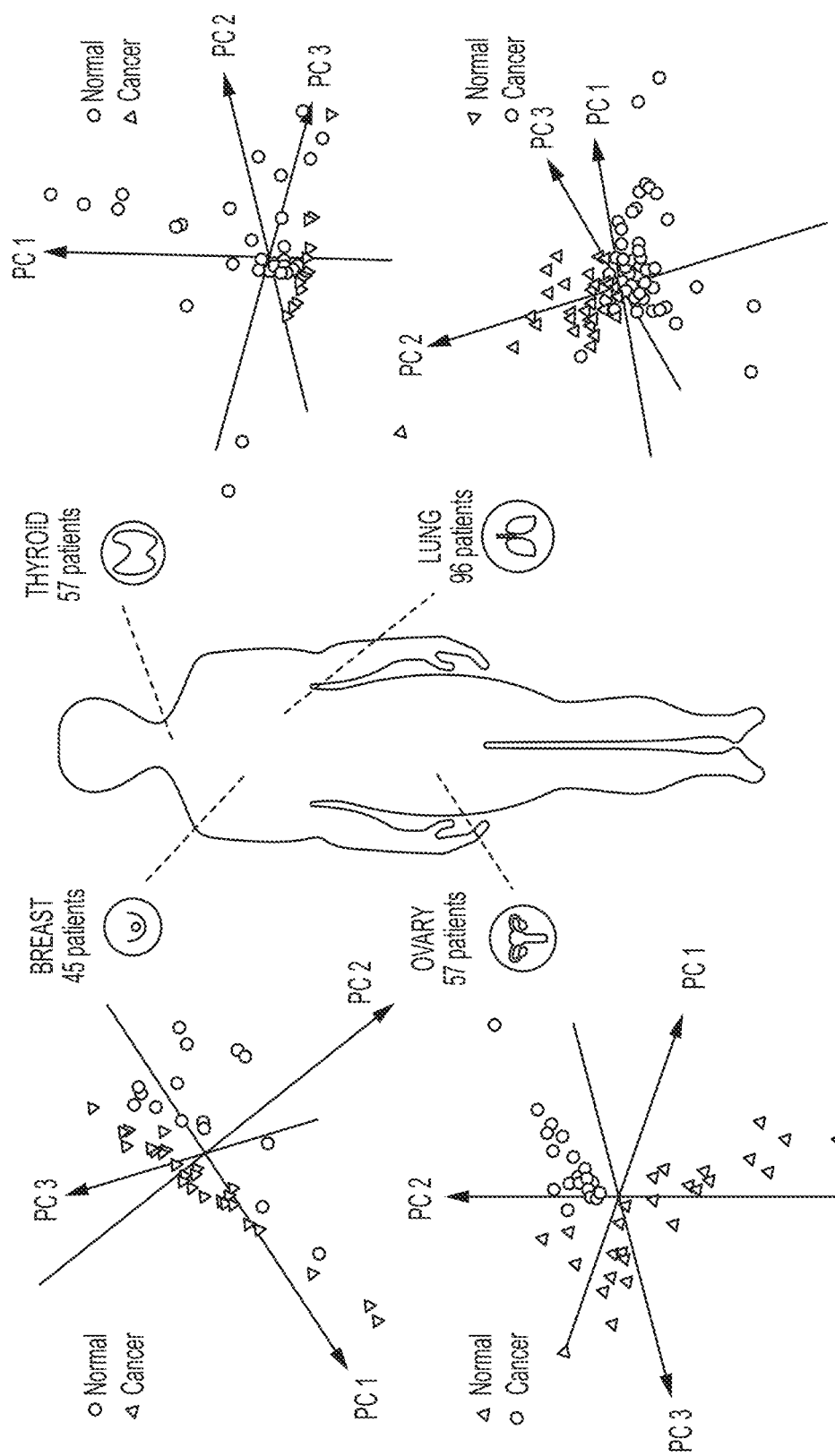
FIG. 11: The molecular information obtained from tissue samples using the MasSpec Pen is diagnostic of human cancer. A total of 253 patient tissue samples were analyzed including breast, thyroid, ovary and lung cancer and normal tissue samples. 3D PCA (PC1, PC2 and PC3) plots shows separation between cancer and normal mass spectra obtained.
Figure 12A:
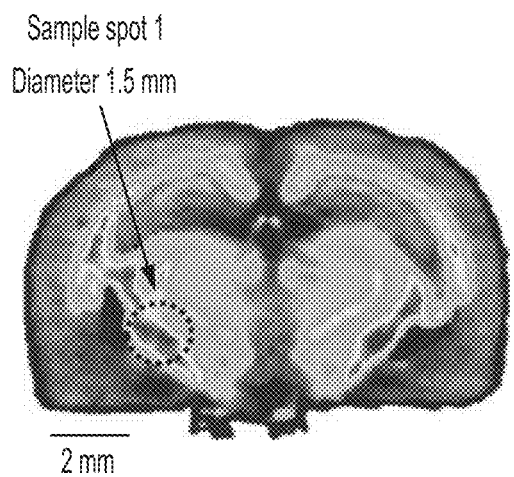
FIGS. 12A-12E: Mapping of the Sample Spot 1 (FIG. 12A), Sample Spot 2 (FIG. 12B), Sample Spot 3 (FIG. 12C), Sample Spot 4 (FIG. 12D), and Sample Spot 5 (FIG. 12E).
Figure 12B:
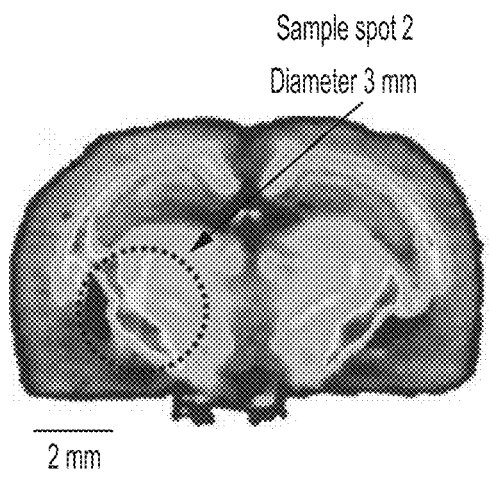
Figure 12C:
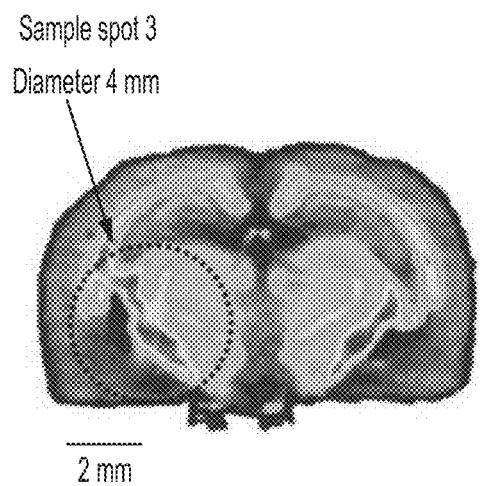
Figure 12D:
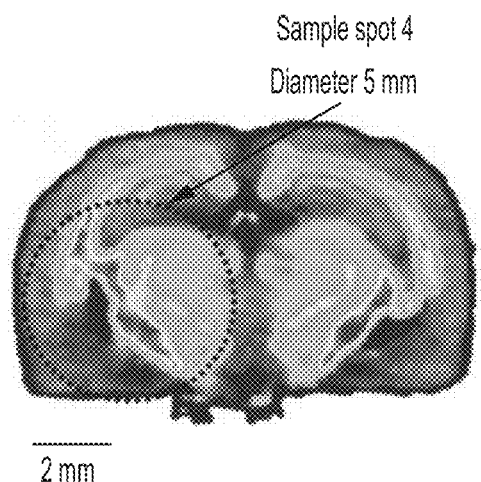
Figure 12E:
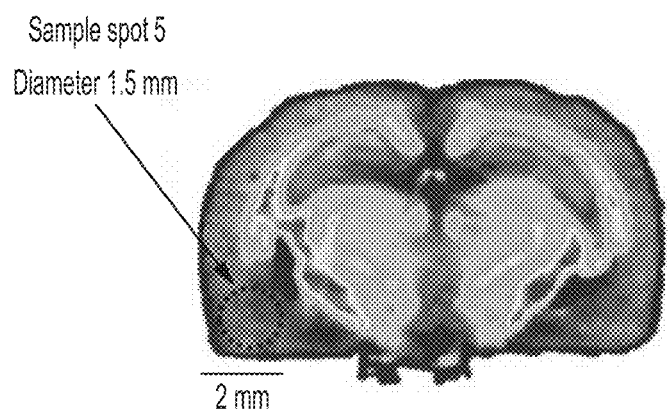
Figure 13A:
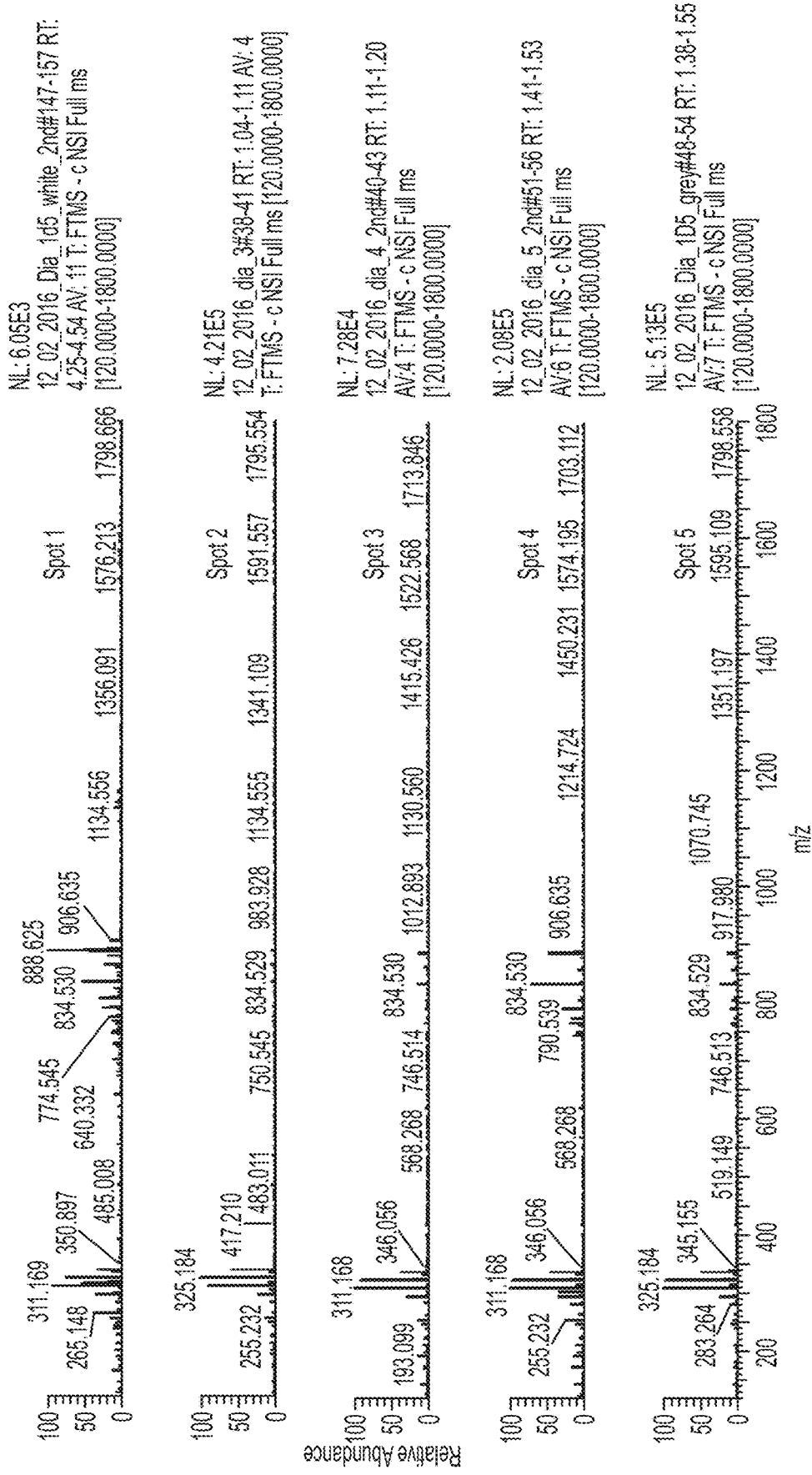
FIGS. 13A-13E: Mass Spectrum of Sample Spots 1-5 at full mass range (FIG. 13A), 500-1800 mass range (FIG. 13B), 500-1000 mass range (FIG. 13C), 785 to 809 mass range (FIG. 13D), and 870 to 920 mass range (FIG. 13E).
Figure 13B:
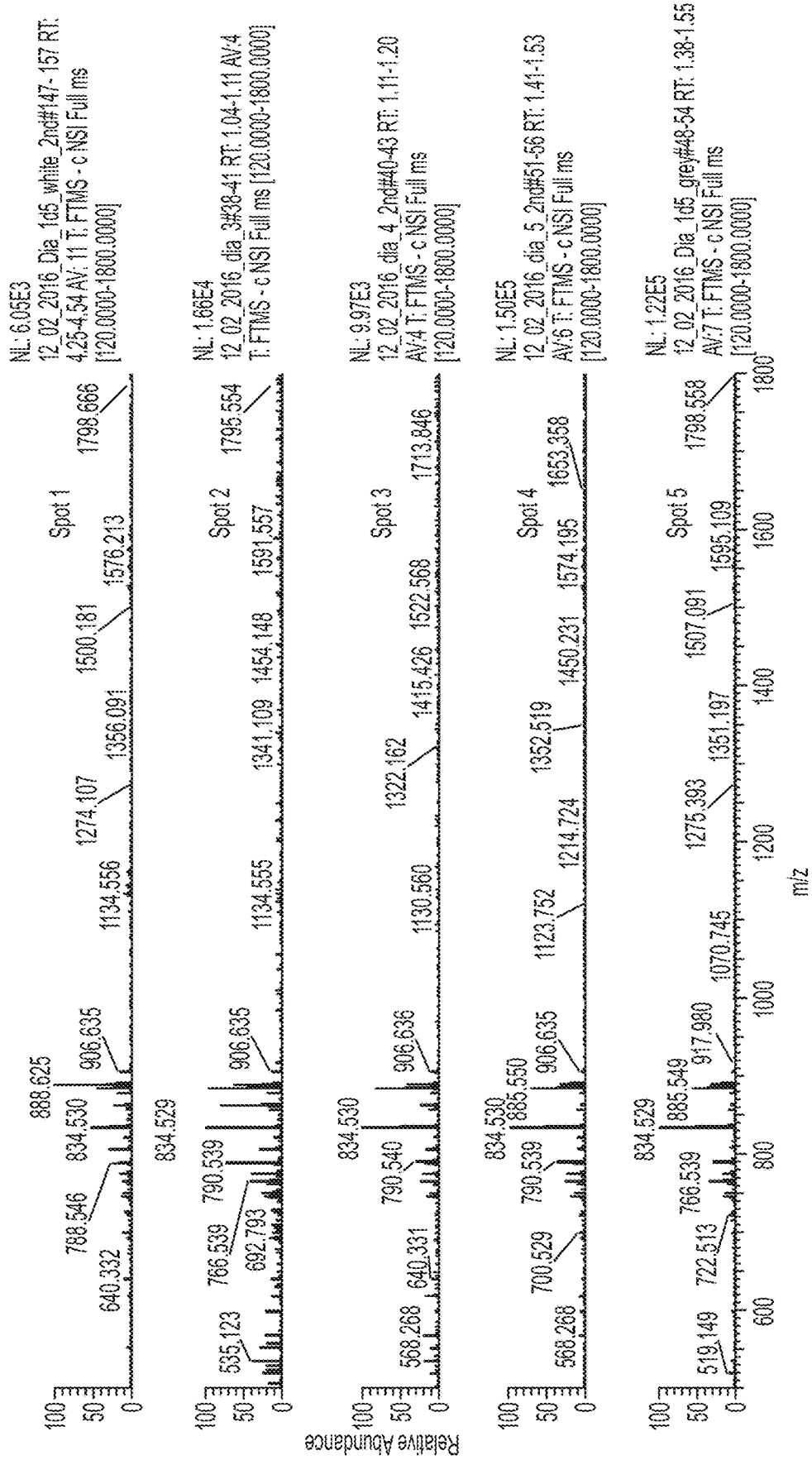
Figure 13C:
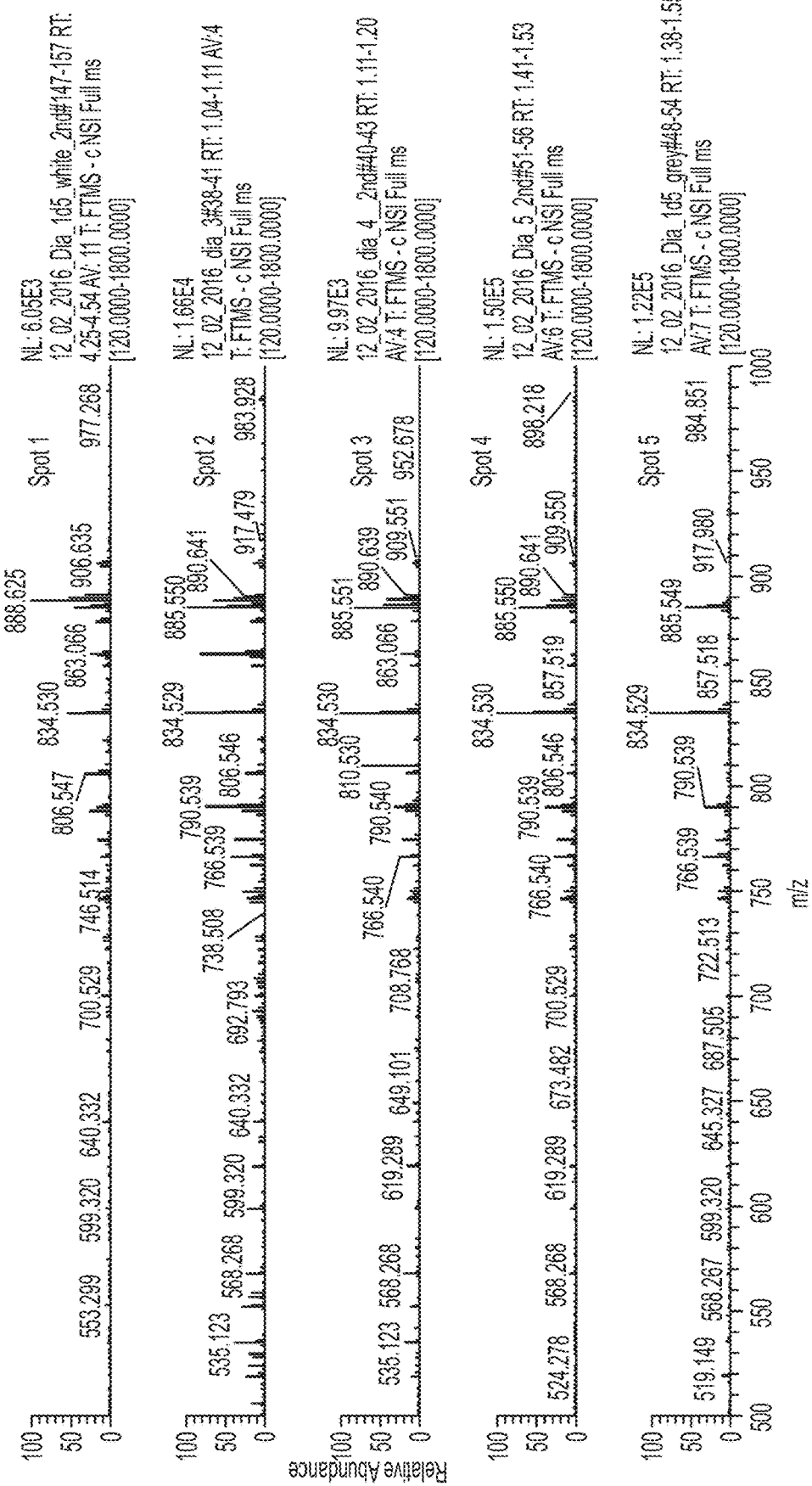
Figure 13D:
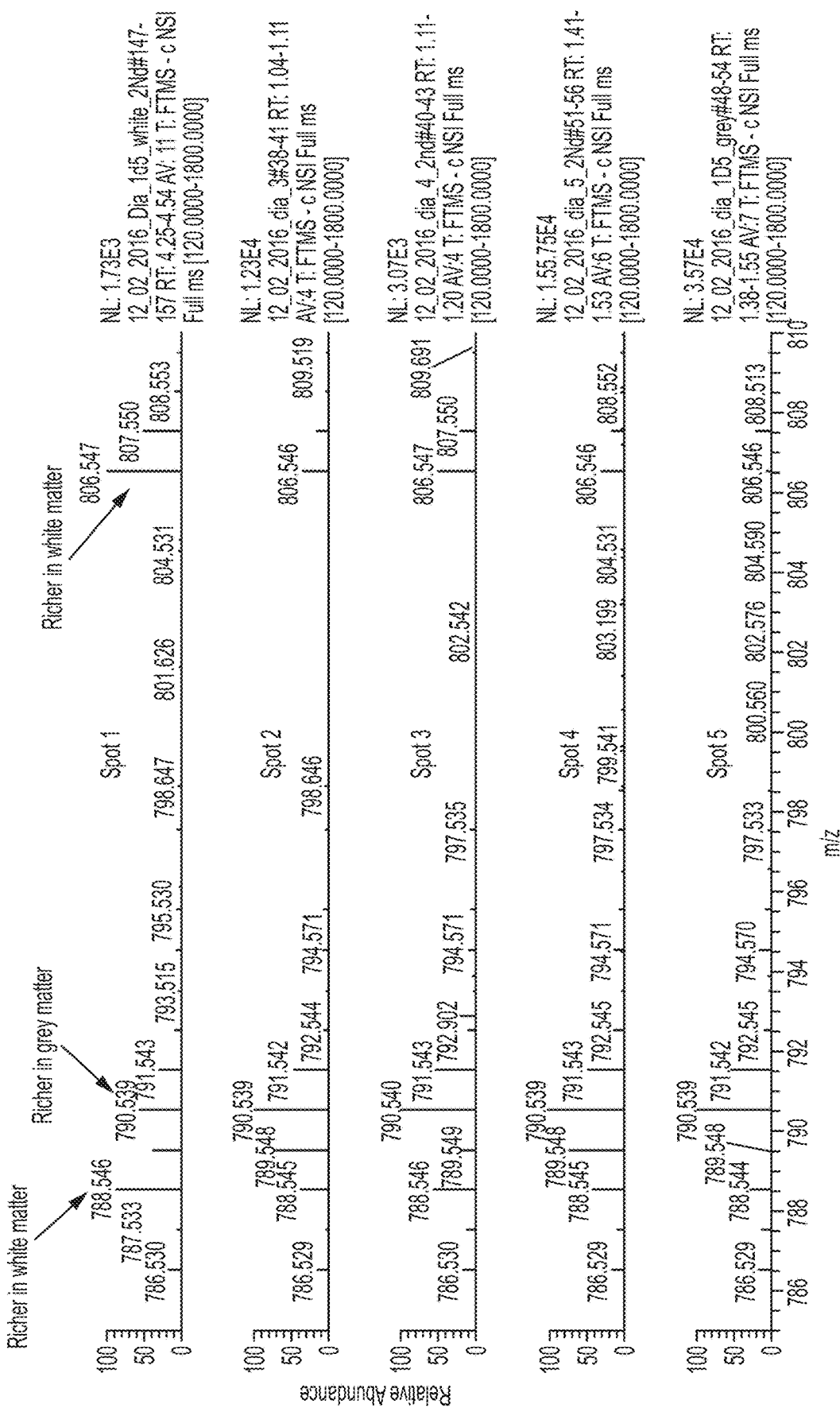
Figure 13E:

It was next evaluated if the molecular information obtained from human tissue samples using the MasSpec Pen was diagnostic and predictive of disease state. A total of 253 human tissue specimens using the MasSpec Pen, including 95 lung samples (47 normal and 48 cancer samples including 17 adenocarcinoma, 17 squamous cell carcinoma, and 14 cancer samples of other histologic subtypes), 57 ovary samples (29 normal and 28 HGSC), 57 thyroid samples (27 normal, 11 follicular thyroid adenoma and 18 papillary thyroid carcinoma), and 45 breast samples (29 normal and 16 ductal carcinoma) (FIG. 11). Patient demographic information is provided in Table 6. After MasSpec Pen analysis, the region analyzed was demarcated and registered through a series of optical images. Then, parallel pieces of the samples were frozen, sectioned at the demarcated region, H&E stained and evaluated by histopathology to derive a diagnosis. Only samples with a predominant cell composition and clear diagnosis were used to build molecular databases. The histologically validated mass spectra obtained for the cancerous samples presented molecular species identified as several lipids and metabolites previously described as potential disease markers using ambient ionization MS techniques. For lung cancer tissue, characteristic molecular markers such as m/z 863.565, identified as PI (36:1), m/z 773.542, identified as PG (36:2), m/z 747.514, identified as PG (34:1), and fatty acids as m/z 281.249, identified as FA (18:1), were observed (FIG. 15 and Table 4). For normal lung, m/z 885.550, identified as PI (38:4), and m/z 744.552, identified as PE (36:1) were observed. The mass spectra obtained for breast cancer tissue presented cer histologic subtypes, 93.8% and 92.2% accuracy was achieved for squamous cell carcinoma and adenocarcinoma, respectively. Thyroid tumor samples investigated included benign follicular thyroid adenoma (FTA) and malignant papillary thyroid carcinoma (PTC) samples. A classifier for each was built yielding 94.7% accuracy for FTA and 97.8% accuracy for PTC. Overall, 96.4% sensitivity, 96.2% specificity and 96.3% accuracy was achieved for all the four types of cancer investigated. These results demonstrate that the molecular information obtained from human tissue samples by the MasSpec Pen is highly predictive of cancer. Further, the results indicate that the statistical classifiers built on the molecular data acquired using the MasSpec Pen are robust and may be used in an automated approach for rapid clinical diagnosis of tissue samples.

TABLE 22

Description of the samples and results obtained using the MasSpec Pen. Pathological diagnosis, number of patient samples, and the Lasso prediction sensitivity, specificity, accuracy, and area under the curve obtained using a leave-one-out cross validation approach are shown.

| Organ | Pathologic Evaluation | | Number of Patients | Lasso Prediction | | | |
|---|---|---|---|---|---|---|---|
| | Diagnosis | Histologic Type | | Sensitivity | Specificity | Accuracy | AUC |
| Breast | Normal | | 29 | 87.5% | 100.0% | 95.6% | 1.00 |
| | Cancer | Ductal Carcinoma | 16 | | | | |
| Lung[a] | Normal | | 47 | 98.0% | 95.7% | 96.9% | 0.97 |
| | Cancer | Adenocarcinoma | 17 | 88.2% | 93.6% | 92.2% | 0.98 |
| | | Squamous Cell | 17 | 88.2% | 95.7% | 93.8% | 0.93 |
| | | Other | 14 | — | — | — | — |
| Ovary | Normal | | 29 | 100.0% | 89.7% | 94.7% | 0.98 |
| | Cancer | High Grade Serous | 28 | | | | |
| Thyroid[b] | Normal | | 27 | — | — | — | — |
| | Tumor | Papillary Carcinoma | 18 | 94.4% | 100.0% | 97.8% | 0.99 |
| | | Follicular Adenoma | 11 | 90.9% | 96.3% | 94.7% | 0.93 |

[a]Lasso prediction results for lung cancer are shown for normal versus all cancer tissues (first row), followed by normal versus lung adernocarcinoma (middle row) and normal versus squamous cell carcinoma (last row).
[b]Lasso prediction results for thyroid cancer are shown for normal versus malignant papillary carcinoma, and normal versus benign follicular adenoma.

diagnostic lipid markers previously described by DESI-MSI (29, 30), including m/z 885.550, identified as PI (38:4), m/z 863.565, identified as PI (36:1), m/z 773.542, identified as PG (36:2), and several FA such as m/z 303.233, identified as FA (20:4), and m/z 281.249, identified as FA (18:1) (Table 5). PCA performed on the data obtained for all the 253 human tissue samples analyzed showed separation between cancer and normal tissues for each organ (FIG. 11).

To evaluate if the MasSpec Pen molecular signatures are predictive of cancer and normal tissues, the Lasso method was applied to build classification models using the histologically validated mass spectral database. The performance of the model was evaluated through a leave-one-patient-out cross-validation approach, and measured by sensitivity and specificity for cancer, as well as accuracy and AUC (Table 22). For breast cancer (n=45), 87.5% sensitivity, 100% specificity (AUC=1.0), an overall accuracy of 95.6% was achieved, which is comparable to the results reported using DESI-MSI (98.2% accuracy, n=126) (Guenther et al., *Cancer Research*, 75, 2015)), the iKnife (95.5% accuracy, n=10) (Balog et al., *Science Translational Medicine*, 5, 2013), and MALDI imaging of lipids and proteins (94.1% accuracy, n=68) (31). For HGSC (n=57), 100% sensitivity, 89.7% specificity, and 94.7% accuracy was achieved (AUC=0.98), which is also similar to classification results obtained by DESI-MSI (97.1% accuracy, n=31) (Sans et al., *Cancer Research*, 2017). For lung cancer (n=956), 98.097.9% sensitivity, 95.7% specificity, and 96.89% accuracy was achieved (AUC=0.97). When predicting based on lung can-

EXAMPLE 8

Figure 19:
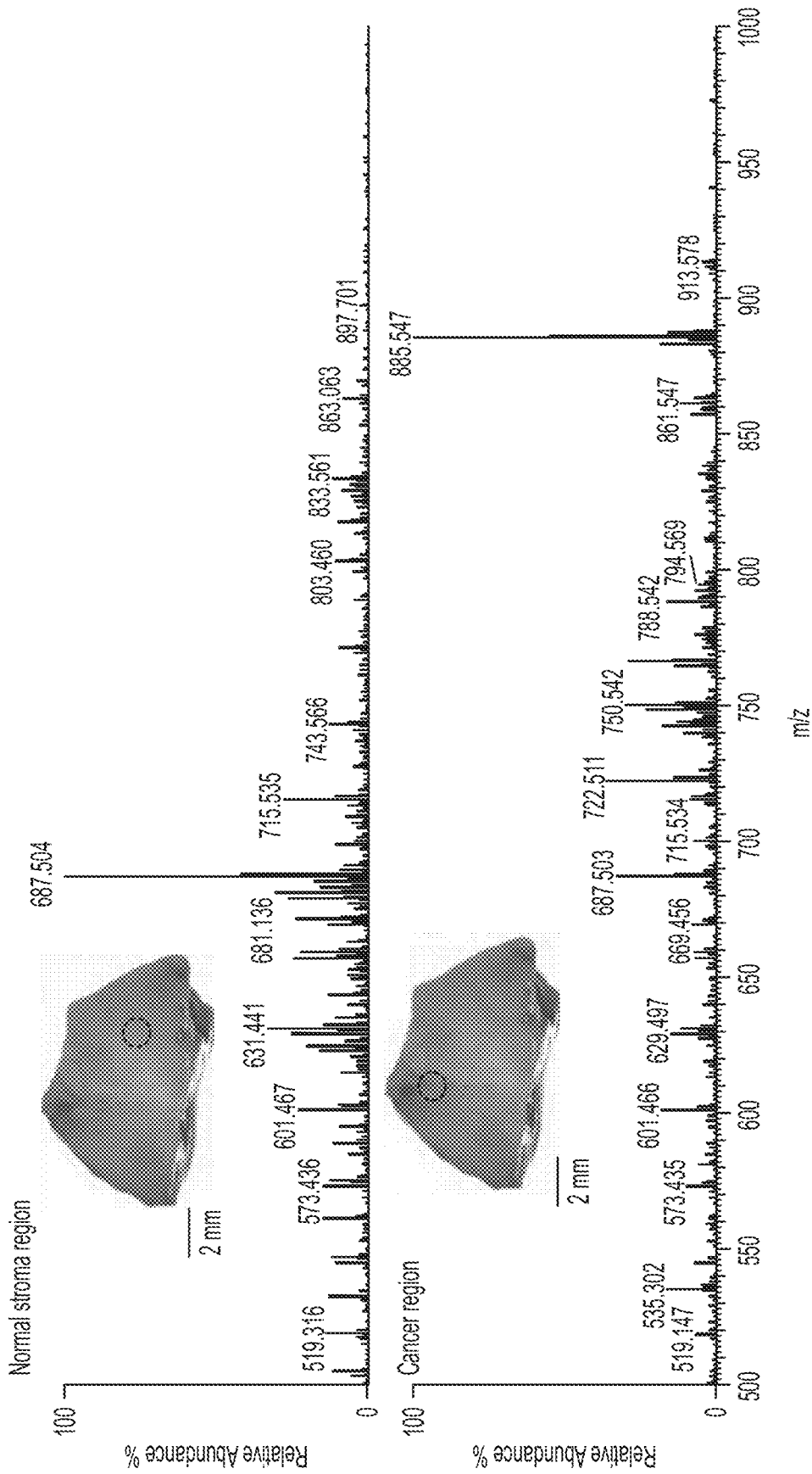
FIG. 19: Representative negative ion mode MasSpec Pen mass spectra obtained from a HGSC tissue sample containing regions of normal and cancer tissues.

Intra-sample Analysis of Histologic Distinct and Cancer Margin Tissue Regions The ability of the MasSpec Pen to identify histologically distinct regions was evaluated in a single human tissue sample that contained regions of HGSC adjacent to normal ovarian stroma tissue. Five consecutive spots in the tissue sample were analyzed using a MasSpec Pen with a 1.5 mm diameter, as demarcated in the optical image shown in FIG. 14A. A tissue section of the sample including the regions analyzed by the MasSpec Pen was subjected to H&E staining and evaluated by histopathology. Spots 1 and 2 were diagnosed by expert pathologists as normal stroma, while regions 4 and 5 were diagnosed as HGSC. Spot 3 was in the margin between the cancer and normal stroma tissue regions, presenting ~50% tumor tissue and ~50% normal stroma tissue. FIG. 14B shows the mass spectra obtained for spots 1, 3 and 5. The spectra obtained for spot 5, HGSC, presented characteristic lipid markers detected in the HGSC tissues analyzed ex vivo to build our statistical classifier (Table 3). The mass spectra obtained for spot 1, diagnosed as normal ovarian stroma tissue, presented less abundant molecules ions as also observed for stroma tissues analyzed ex vivo. Spot 3 presented molecular profiles characteristic of HGSC with lower total abundance due to the contribution of normal stroma tissue present within the region analyzed. The mass spectra obtained for the 5 spots were then evaluated by our ovarian cancer molecular classifier as an independent validation set. Remarkably, this classified correctly predicted spots 1 and 2 as normal, and 3, 4 and 5 as cancer (FIG. 14C). Similar results were obtained for a different tissue sample with histologically distinct regions (FIG. 19). These results show that the molecular information obtained by the MasSpec Pen can be used to detect cancer in marginal regions with mixed composition of normal and cancer cells.

EXAMPLE 9

In Vivo Analysis of a Murine Model of Human Breast Cancer During Surgery

Figure 16A:
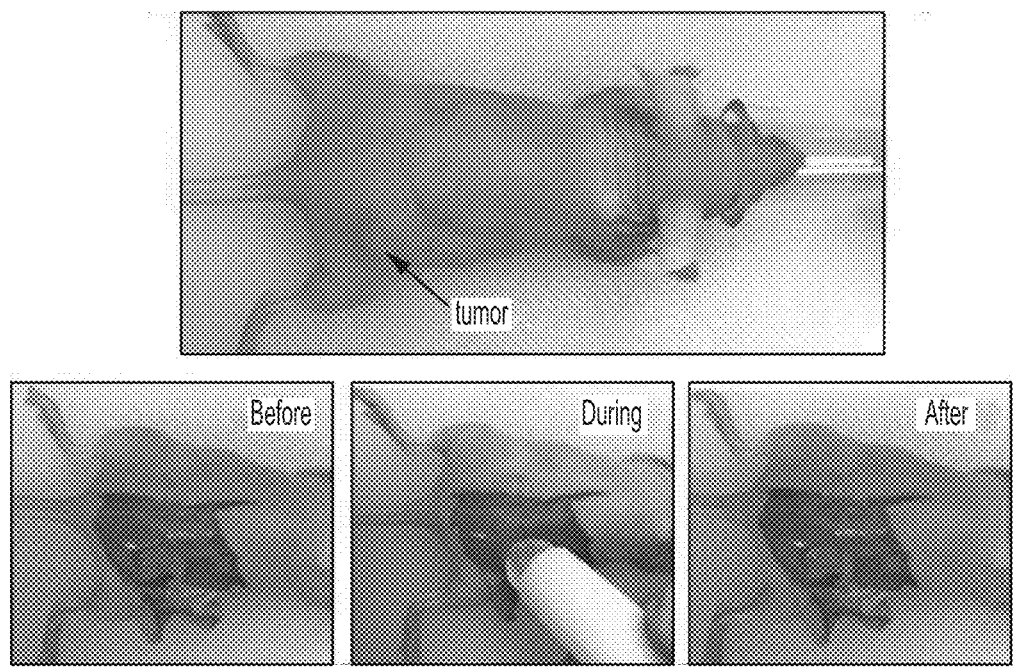
FIGS. 16A-16B: In vivo analysis of tumor and normal tissues during surgery on a murine animal model. A) Experiments were performed on mice under anesthesia. Optical images show the animal and in vivo before, during, and after MasSpec Pen analysis. B) Representative negative ion mode mass spectra show distinct molecular profiles from normal and tumor tissues.
Figure 16B:
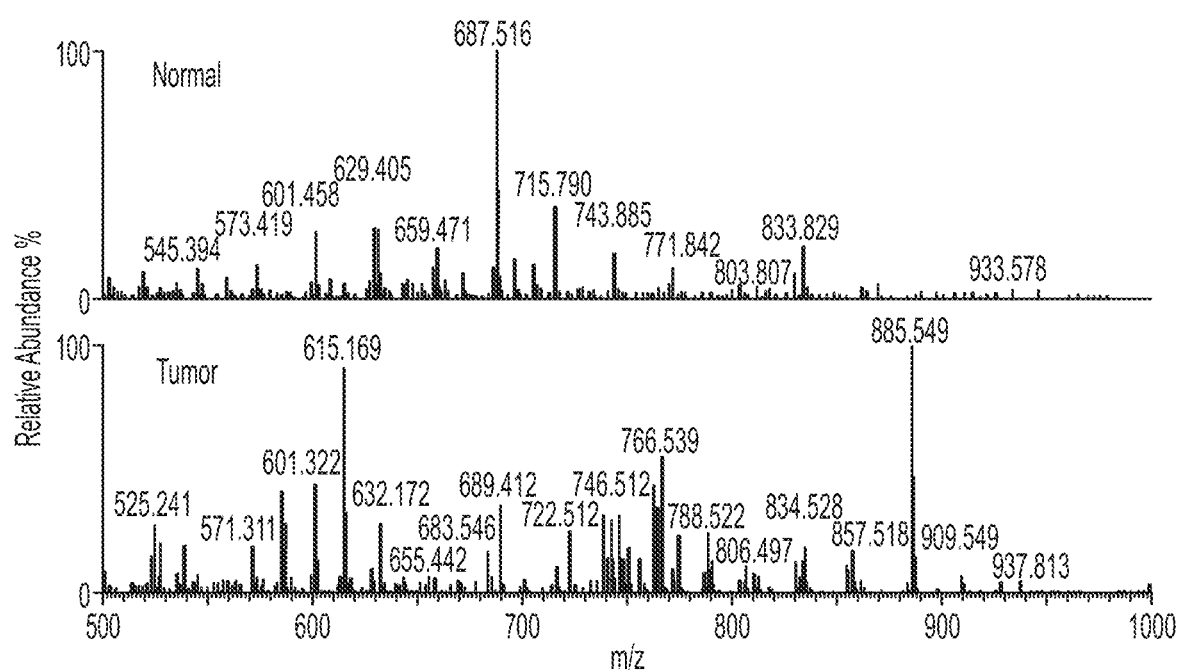
Figure 20:
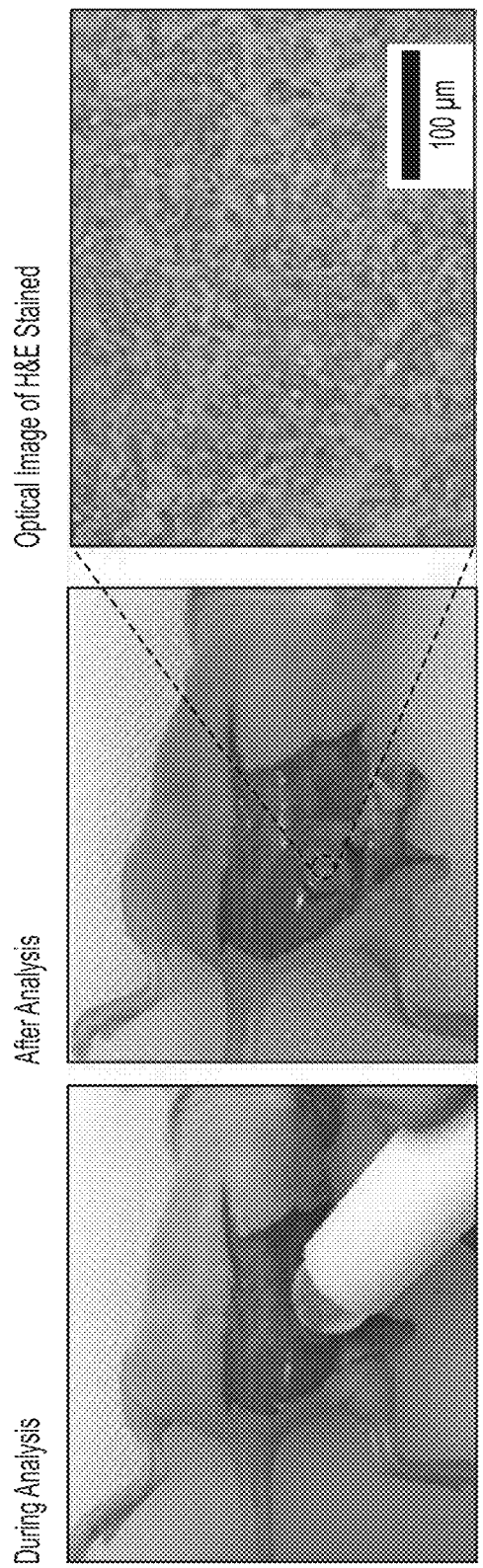
FIG. 20: Optical image of the in vivo analysis after and the H&E stained tissue section obtained from the same region after MasSpec Pen analysis.
Figure 21:
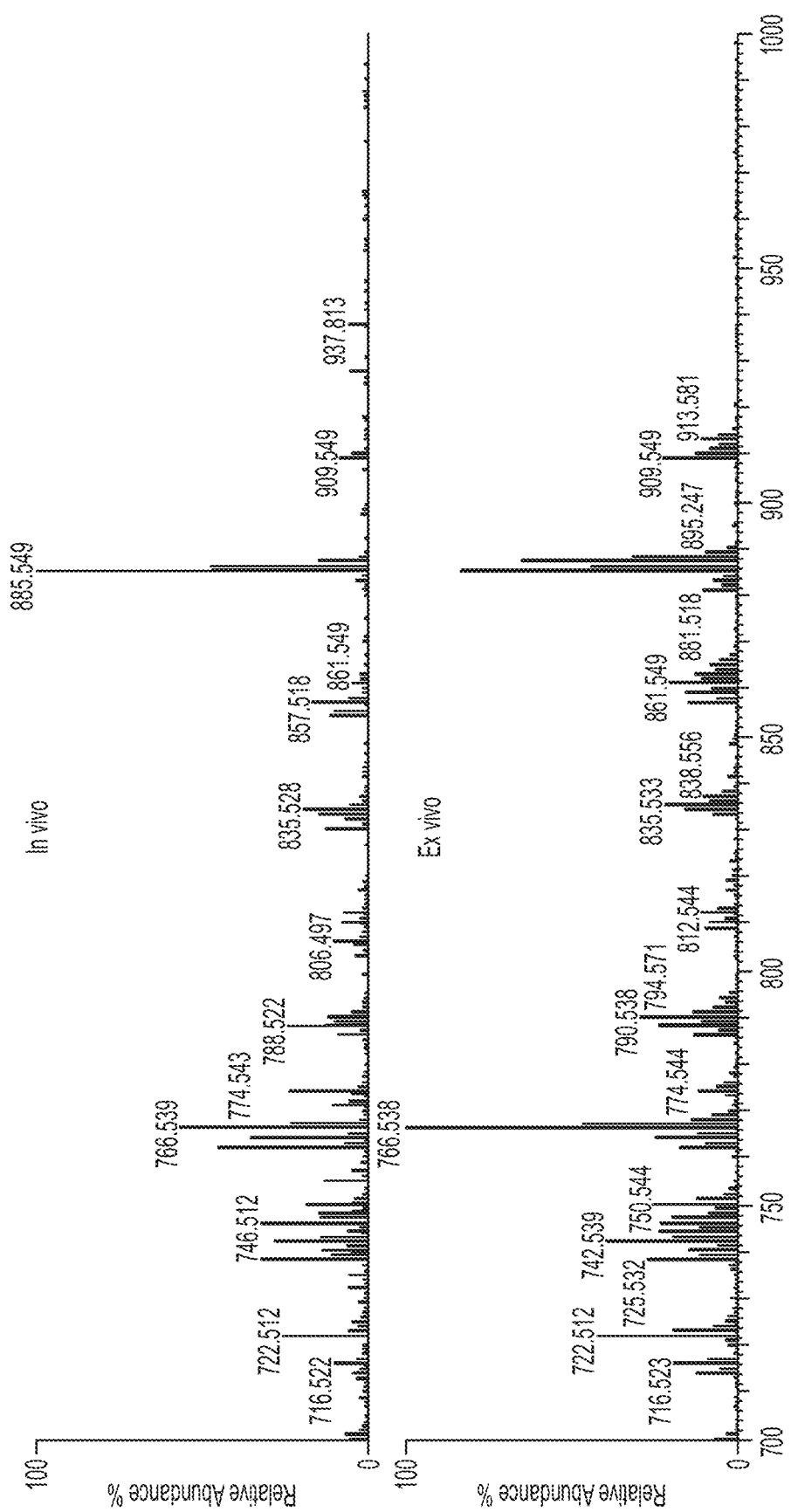
FIG. 21: Comparison between the MasSpec Pen negative ion mode mass spectra obtained in vivo and ex vivo of the same tumor sample from mouse model.

The MasSpec Pen was designed with biocompatible materials to ensure full compatibility as an in vivo molecular diagnostic tool. The MasSpec Pen was tested for in vivo tissue analysis using a murine model of human breast cancer. BT474 HER2+ breast cancer cells were implanted subcutaneously in nude athymic mice (n=3). The tumors were grown to an average of 250 mm$^3$ over a period of 4 weeks. All surgical and MasSpec Pen analysis procedures were performed under anesthesia. A surgical blade was used to open a flap of skin surrounding the tumor, and then the skin flap was sharply dissected from the surface of the tumor. The exposed tumor was then analyzed using the MasSpec Pen following the same automated experimental steps described previously. FIG. 16A shows an optical image of the animal under anesthesia prior to initiation of surgery, before analysis (and after surgical removal of the skin), during the MasSpec Pen analysis, and after the analysis. Several tissue regions were analyzed for each animal investigated, including multiple positions of the top of the tumor, the core of the tumor after partial tumor resection, as well as adjacent normal soft connective tissue. The mass spectra obtained for the tumor regions presented many molecular species observed in human breast tissue, with a clearly distinctive profile from what was obtained for adjacent normal soft connective tissue regions (FIG. 16B). Using optical microscopy, no observable macroscopic or microscopic damage to the tissue regions analyzed were detected due to MasSpec Pen analyses, as evidenced by the optical images obtained of H&E stained tissue sections (FIG. 20). Further, no apparent effects to the health of the animals were observed due to the MasSpec Pen analysis during surgery. After in vivo analysis, freshly excised tumor specimens were also analyzed ex vivo, yielding mass spectra with common lipid species to those observed in the in vivo analysis despite variations in relative abundances, which are likely due to the re-analysis process of the same tissue region (FIG. 21). These results suggest that the MasSpec Pen is suitable for in vivo molecular evaluation and cancer diagnosis.

EXAMPLE 10

Materials and Methods

Study Design: The objective of this study was to evaluate the potential of a new mass spectrometry-based probe to non-destructively analyze and diagnose cancer in human tissue samples. In this study, the molecular profiles of human tissue samples obtained from 282 patients including normal and cancer breast, lung, thyroid, and ovary tissues were investigated. All patient samples were obtained from the Cooperative Human Tissue Network (CHTN), Asterand Biosciences (Detroit, Mich.), the MD Anderson Tissue Bank, and the Baylor College of Medicine Tissue Bank, under approved Institutional Review Board (IRB) protocol. The mass spectra obtained using the MasSpec Pen in tissue samples were normalized, background subtracted and analyzed using a statistical technique to build classification models. Expert, board-certified pathologists (J.L, W.Y, and N.C) evaluated H&E stained tissue sections obtained from the tissue samples analyzed. The pathologists were blind to any information about the acquisition from mass spectrometry analysis. Samples were excluded from statistical analysis if they were determined by the pathologist to have substantial heterogeneity in cell composition, which included 28 samples. The in vivo animal model experiments were conducted under approved Institutional Animal Care and Use Committee (IACUC) protocol.

Design and Engineering of the MasSpec Pen: A 3D printer (Model uPrint SE plus) was used to print the key component—PDMS (Dow Corning, Midland, Mich., USA) probe tip. The pen tips were fabricated by casting an elastomer from a negative mold and then dissolving the mold away. The negative molds were designed using SolidWorks computer aided design (CAD) software and then fused deposition modeled with the 3D printer using ABS plastic (Stratasys, Eden Prairie, Minn., USA) and soluble support material. The parts were then washed to remove support material, using a support cleaning apparatus (SCA-1200HT, SCA) and solvent (EcoWorks) at 70° C. for 24 hrs or until support material was fully dissolved. For the casting, a mixture of PDMS elastomer base and curing agent (Sylgard 184, Dow Corning) were prepared in a weight ratio of 10:1, respectively. The mixture was poured into the 3-D printed molds, cured in an oven (10GCE-LT, Quincy Lab) at 74° C. for 1 h, and then placed in a closed container with acetone (Fisher Scientific, Waltham, Mass., USA) to dissolve. The final washing step had the tips sonicated in acetone to remove any remaining ABS. PTFE tubing (ID 1/32 inch, OD 1/16 inch, Cole-Parmer, Vernon Hills, Ill., USA) was directly inserted into the probe tip for experiments.

Data Acquisition: All experiments were performed on a Q Exactive hybrid Quadrupole-Orbitrap mass spectrometer (Thermo Fisher Scientific, San Jose, Calif.). Full-scan was carried out at the range of m/z 120-1800, using resolving power 140,000, capillary temperature of 350° C. and S-lens RF level of 100. Wild-type mouse brain were purchased from BioreclamationIVT (Westbury, N.Y.). A total of 282 human tissue specimens including breast, thyroid, ovary, and lung were obtained frozen and stored in a −80° C. freezer until analysis, when they were thawed in room temperature. The tissues were placed in a surface and analyzed by the MasSpec Pen using the experimental steps described. After experiments, the tissue regions analyzed were annotated, frozen, and 16 μm tissue sections prepared using a CryoStar™ NX50 cryostat. Additional tissue sections at different regions of the tissue piece were obtained for MS analysis. Tissue sections were kept frozen until analysis, when they were in room temperature and analyzed by the MasSpec Pen. Tissue sections were then H&E stained and evaluated by histopathology. The pathologic diagnosis was used as the reference for our molecular database.

In Vivo Experiments: In vivo experiments were performed during surgical resection of tumors using murine animal models while the mice were under anesthesia (2% isoflurane, 98% O2). BT474 HER2+ cells were grown in improved minimal essential medium (IMEM, Invitrogen, Carlsbad, Calif.) supplemented with 10% FBS, 1% L-glutamine, and 1% insulin, to 80-90% confluency in 5% $O_2$ and 37° C. Cells were counted via hemocytometer and trypan blue dye exclusion. Nude athymic female mice (N=3) were subcutaneously implanted with a 0.72 mg, 60-day release, 17β-estradiol pellet (Innovative Research of America, Sarasota, Fla.) in the nape of the neck. Approximately 24 hours later, BT474 breast cancer cells ($10^7$) in serum-free IMEM media with 20% growth factor-reduced Matrigel were injected subcutaneously into the right flank of the mouse (total injection of 100 μL). Tumors were monitored weekly for growth until they reached 0.7-1.0 cm in diameter (average of 250 mm$^3$). At that time point, all surgical procedures were performed while the mice were under anesthesia (2% isoflurane, 98% $O_2$). A surgical blade was used to open a flap of skin, leaving an estimated 1-2 cm of space around the tumors, and then the skin flap was dissected from the surface of the tumor. The skin was flapped to expose the tumor and adjacent normal tissues, which were analyzed in several regions using the MasSpec Pen. Pieces of the tumor were then resected using a scalpel and analyzed ex vivo. Tumor tissue regions analyzed by the MasSpec pen were annotated, flash frozen, sectioned, and subjected to H&E staining for diagnosis.

Statistical Analysis: Averages of three mass spectra obtained during each 10 seconds MasSpec Pen analysis were used to build molecular databases. The Xcalibur raw data was converted to Microsoft Excel spreadsheet format. The full mass range of the spectra were partitioned into bins by rounding m/z values to the nearest hundredth. All mass spectra were first normalized according to total ion count (TIC) or to the absolute intensity of m/z 885.55, to account for slight fluctuations in signal intensities that may occur between experiments. Then, background peaks as well as peaks not appearing in at least 10% of the samples analyzed were excluded to reduce random noise.

For each tissue section (breast or thyroid), four representative mass spectra for each tissue section analyzed were imported to metaboanalyst (http://www.metaboanalyst.ca/) for principal component analysis (PCA) using the website built-in function. Score plots and loading plots were generated through the website for each tissue type. For each soft tissue sample type (breast, thyroid, lung, and ovary), the data was imported to R programming language. PCA was performed by centering the pre-processed data to mean zero and computing principal components using the prcomp function in R. The first three principal components were visualized with the rgl and pca3d packages for R. For tissue classification, the Lasso method was applied using the glmnet package in the CRAN R language library. Models generated using the Lasso are simpler to interpret than other regularization methods, as it yields "sparse" models, that is, models that involve only a subset of the features. A mathematical weight for each statistically informative feature is calculated by the Lasso depending on the importance that the mass spectral feature has in characterizing a certain class (cancer versus normal, or a cancer subtype versus normal). Classification was performed using a leave-one-out cross-validation approach to assess the predictive accuracy within the training set. Performance of trained classifiers was measured by sensitivity, specificity, accuracy, and AUC.

* * *

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method for assessing tissue samples in a living subject comprising:
   (a) applying a fixed or discrete volume of a solvent to a tissue site in the living subject, using a probe that is structurally separate from, and in fluid contact with the tissue site and wherein the fixed or discrete volume of the solvent is not applied as a desorption electrospray ionization (DESI)-spray;
   (b) collecting the applied solvent with the probe to obtain a liquid sample; and
   (c) subjecting the liquid sample to mass spectrometry analysis.

2. The method of claim 1, wherein the fixed or discrete volume of a solvent is applied as a droplet.

3. The method of claim 1, wherein the fixed or discrete volume of a solvent is applied using a mechanical pump to move the solvent through a solvent conduit.

4. The method of claim 1, wherein collecting the applied solvent comprises applying a negative pressure to pull the liquid sample into a collection conduit and/or applying a gas pressure to push the liquid sample into a collection conduit.

5. The method of claim 4, wherein the solvent is applied through a solvent conduit that is separate from the collection conduit.

6. The method of claim 5, wherein the gas pressure is applied through a gas conduit that is separate from the solvent conduit and the collection conduit.

7. The method of claim 1, wherein the fixed or discrete volume of solvent is between 0.1 and 100 microliters.

8. The method of claim 1, wherein the applied solvent is collected between 0.1 and 30 seconds after the applying step.

9. The method of claim 1, wherein the tissue site is an internal tissue site in the living subject.

10. The method of claim 1, further comprising collecting a plurality of liquid samples from a plurality of tissue sites.

11. The method of claim 10, wherein the probe is washed between collecting respective liquid samples from the plurality of tissue sites.

12. The method of claim 10, wherein the probe is disposable and is changed between collecting respective liquid samples from the plurality of tissue sites.

13. The method of claim 10, wherein the probe comprises a collection tip, and the method further comprises:
   ejecting the collection tip from the probe after the respective liquid samples are collected.

14. The method of claim 10, wherein the plurality of tissue sites surrounds a section of tissue that has been surgically resected.

15. The method of claim 1, further comprising:
   (d) characterizing the liquid sample based on the mass spectrometry analysis.

16. The method of claim 15, wherein characterizing the liquid sample comprises determining a tissue type of the tissue site.

17. The method of claim 16, wherein determining the tissue type comprises identifying a diseased tissue.

18. The method of claim 17, wherein the diseased tissue comprise cancer cells.

19. The method of claim 17, wherein the diseased tissue comprise lung, breast, ovarian or thyroid cancer cells.

20. The method of claim 1, wherein the probe comprises:
a reservoir, a first conduit, a second conduit and a third conduit, wherein:
the reservoir is in fluid communication with the first conduit, the second conduit and the third conduit;
the first conduit is in fluid communication with a chamber comprising the solvent;
the second conduit is in fluid communication with a gas supply; and
the third conduit is in fluid communication with a mass spectrometer.

21. The method of claim 1, wherein the solvent is sterile.

22. The method of claim 1, wherein the solvent is water.

23. The method of claim 1, wherein the probe is in contact with the tissue site when the fixed or discrete volume of the solvent is applied to the tissue site.

24. The method of claim 1, wherein the probe is flushed after the obtaining the liquid sample.

25. The method of claim 1, wherein the reservoir has a volume between 1 and 500 microliters.

26. A method for obtaining a mass spectrometry profile for a tissue site in a living subject comprising:
(a) using a probe that is structurally separate from, and in fluid contact with, the tissue site to apply a discrete volume of a solvent to the tissue site in the living subject and wherein the discrete volume of the solvent is not applied as a desorption electrospray ionization (DESI)-spray;
(b) using the probe to collect the applied solvent to obtain a liquid sample; and
(c) subjecting the liquid sample to mass spectrometry analysis.

* * * * *